(12) United States Patent
Cheng et al.

(10) Patent No.: US 10,336,684 B2
(45) Date of Patent: Jul. 2, 2019

(54) PHENYL-(AZA)CYCLOALKYL CARBOXYLIC ACID GPR120 MODULATORS

(71) Applicant: BRISTOL-MYERS SQUIBB COMPANY, Princeton, NJ (US)

(72) Inventors: Peter T. W. Cheng, Princeton, NJ (US); David S. Yoon, Yardley, PA (US)

(73) Assignee: Bristol=Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/033,645

(22) Filed: Jul. 12, 2018

(65) Prior Publication Data

US 2018/0319737 A1  Nov. 8, 2018

Related U.S. Application Data

(63) Continuation of application No. 15/509,237, filed as application No. PCT/US2015/048784 on Sep. 8, 2015, now abandoned.

(60) Provisional application No. 62/047,707, filed on Sep. 9, 2014.

(51) Int. Cl.

| | | |
|---|---|---|
| C07C 229/42 | (2006.01) | |
| C07C 59/72 | (2006.01) | |
| C07D 205/04 | (2006.01) | |
| C07C 62/34 | (2006.01) | |
| C07C 59/68 | (2006.01) | |
| C07C 59/64 | (2006.01) | |
| C07D 213/65 | (2006.01) | |
| C07D 211/46 | (2006.01) | |
| C07D 211/42 | (2006.01) | |
| C07D 211/14 | (2006.01) | |
| C07D 207/12 | (2006.01) | |
| C07D 223/08 | (2006.01) | |
| A61K 31/192 | (2006.01) | |
| A61K 31/196 | (2006.01) | |
| A61K 31/397 | (2006.01) | |
| A61K 31/402 | (2006.01) | |
| A61K 31/44 | (2006.01) | |
| A61K 31/451 | (2006.01) | |
| A61K 31/55 | (2006.01) | |

(52) U.S. Cl.
CPC .......... *C07C 229/42* (2013.01); *A61K 31/192* (2013.01); *A61K 31/196* (2013.01); *A61K 31/397* (2013.01); *A61K 31/402* (2013.01); *A61K 31/44* (2013.01); *A61K 31/451* (2013.01); *A61K 31/55* (2013.01); *C07C 59/64* (2013.01); *C07C 59/68* (2013.01); *C07C 59/72* (2013.01); *C07C 62/34* (2013.01); *C07D 205/04* (2013.01); *C07D 207/12* (2013.01); *C07D 211/14* (2013.01); *C07D 211/42* (2013.01); *C07D 211/46* (2013.01); *C07D 213/65* (2013.01); *C07D 223/08* (2013.01); *C07C 2601/02* (2017.05); *C07C 2601/08* (2017.05); *C07C 2601/18* (2017.05)

(58) Field of Classification Search
CPC ....... C07C 229/42; C07C 59/72; C07C 62/34; C07C 59/68; C07D 205/04; C07D 211/46; C07D 211/42; C07D 211/14; C07D 207/12; C07D 223/08
See application file for complete search history.

(56) References Cited

U.S. PATENT DOCUMENTS

| | | | |
|---|---|---|---|
| 3,733,416 A | 5/1973 | Diamond et al. | |
| 3,864,384 A | 2/1975 | Diamond et al. | |
| 4,281,065 A | 7/1981 | Lin et al. | |
| 5,716,944 A | 2/1998 | Sohda et al. | |
| 5,994,356 A | 11/1999 | Pieper et al. | |
| 6,008,220 A * | 12/1999 | Hupe ................... | C07D 211/34 514/252.03 |
| 6,011,155 A | 1/2000 | Villhauer | |
| 8,962,660 B2 | 2/2015 | Zhang et al. | |
| 9,518,000 B2 | 12/2016 | Shi et al. | |
| 9,598,390 B2 | 3/2017 | Shi et al. | |

(Continued)

FOREIGN PATENT DOCUMENTS

| | | |
|---|---|---|
| EP | 2 289 868 A1 | 3/2011 |
| FR | 2 238 485 A1 | 2/1975 |
| JP | 06122636 | 5/1994 |

(Continued)

OTHER PUBLICATIONS

Abdel-Atty, Mona M. et al., "Design, synthesis, 3D pharmacophore, QSAR, and docking studies of carboxylic acid derivatives as Histone Deacetylase inhibitors and cytotoxic agents", Bioorganic Chemistry, vol. 57, pp. 65-82 (2014).

(Continued)

*Primary Examiner* — Matthew P Coughlin
(74) *Attorney, Agent, or Firm* — Jing G. Sun

(57) ABSTRACT

The present invention provides compounds of Formula (I):

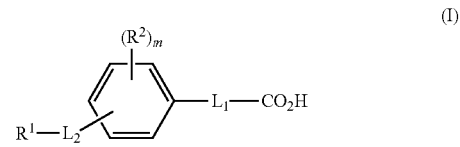

or a stereoisomer, or a pharmaceutically acceptable salt thereof, wherein all of the variables are as defined herein. These compounds are GPR120 G protein-coupled receptor modulators which may be used as medicaments.

16 Claims, No Drawings

(56) References Cited

U.S. PATENT DOCUMENTS

| | | |
|---|---|---|
| 9,938,222 B2 | 4/2018 | Shi et al. |
| 2017/0247311 A1 | 3/2017 | Shi et al. |

FOREIGN PATENT DOCUMENTS

| | | |
|---|---|---|
| WO | WO2008/005964 A2 | 1/2008 |
| WO | WO2008/021928 A2 | 2/2008 |
| WO | WO2011/051165 A1 | 5/2011 |
| WO | WO2012/124744 A1 | 9/2012 |
| WO | WO2014/151247 A1 | 9/2014 |
| WO | WO2014/159794 A2 | 10/2014 |
| WO | WO2014/159802 A1 | 10/2014 |
| WO | WO2016/040222 A1 | 3/2016 |
| WO | WO2016/040223 A1 | 3/2016 |

OTHER PUBLICATIONS

Arbeeny, C. et al., "The Metabolic Syndrome: From Pathophysiology to Novel Treatment Strategies", Current Med. Chem—Imm. Endoc. & Metab. Agents, vol. 1, pp. 1024 (2001).

Barlind, J., et al., "Identification and design of a novel series of MGAT2 inhibitors", Bioorganic & Medicinal Chemistry Letters, vol. 23, pp. 2721-2726 (2013).

Bullock, F.J., "Antiprotozoal Quinones. I. Synthesis of 2-Hydroxy-3-alkyl-1,4-naphthoquinones as Potential Coccidiostats", J. Medicinal Chemistry, vol. 11(3),pp. 419-424 (1968).

Cagniant, Paul et al., "Cleavage and migration of the cyclopentyl radical during cyclization reactions of phenylcyclopentane derivatives", Compt. Rend. vol. 224, pp. 473-474 (1947).

Ford, Earl et al., "Prevalence of the Metabolic Syndrome Among Us Adults", JAMA, vol. 287(3), pp. 356-359 (2002).

Halder, S. et al., "The therapeutic potential of GPR120: a patent review", Expert Opinion on Therapeutic Patents, vol. 23(12), pp. 1581-1590 (2013).

Ichimura, A. et al., "Dysfunction of lipid sensor GPR120 leads to obesity in both mouse and human", Nature, vol. 483, pp. 350-354 (2012).

Im, Dong-Soon, "Omega-3 fatty acids in anti-inflammation (pro-resolution) and GPCRs", Progress in Lipid Research, vol. 51, pp. 232-237 (2012).

Kahn, S. et al., "Effects of pioglitazone and vildagliptin on coagulation cascade in diabetes mellitus-targeting thrombogenesis", Expert Opinion on Therapeutic Targets, Vo. 17(6), pp. 627-639 (2013).

Legros, R. et al., "New derivatives of benzocycloheptenes", Comptes Rendus Hebdomadaires pp. 2733-2735 (1961).

Miyauchi, S., "Distribution and regulation of protein expression of the free fatty acid receptor GPR120", Naunyn-Schmied Arch Pharmacol, vol. 379, pp. 427-434 (2009).

Oh, Da Young, et al., "GPR120 is an Omega-3 Fatty Acid Receptor Mediating Potent Anti-inflammatory and Insulin-Sensitizing Effects", Cell, vol. 142, pp. 687-698 (2010).

Rovnyak, G. et al., "Synthesis and Antiinflammatory Activities of (α-Cyclopropyl-p-tolyl)acetic Acid and Related Compounds", vol. 16(5), pp. 487-490 (1973).

Verma, M. et al., Inhibiting wild-type and C299S mutant AKR1B10: a homologue of aldose reductase upregulated in cancers, European J. Pharmacology, vol. 584, pp. 213-221 (2008).

CAS Registry No. 1267419-70-4 (Mar. 9, 2011).
CAS Registry No. 1481490-58-7 (Nov. 26, 2013).
CAS Registry No. 1509701-14-7 (Jan. 2, 2014).
CAS Registry No. 1512286-98-4 (Jan. 6, 2014).
CAS Registry No. 1506649-07-5 ( Dec. 30, 2013).

* cited by examiner

PHENYL-(AZA)CYCLOALKYL CARBOXYLIC ACID GPR120 MODULATORS

CROSS-REFERENCE TO RELATED APPLICATIONS

This application is a continuation of U.S. patent application Ser. No. 15/509,237, filed Mar. 7, 2017, which is a 371 of International Application No. PCT/US2015/048784, filed on Sep. 8, 2015, which claims priority to U.S. Provisional Application Ser. No. 62/047,707, filed Sep. 9, 2014; the entire content of which is incorporated herein reference.

FIELD OF THE INVENTION

The present invention provides novel phenylcycloalkyl and phenyl-azacycloalkyl carboxylic acid compounds, and their analogues thereof, which are GPR120 G protein-coupled receptor modulators, compositions containing them, and methods of using them, for example, for the treatment of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Polyunsaturated fatty acids (PUFAs) such as omega-3 fatty acids are known to improve sensitivity to insulin. Insulin sensitivity can be improved by exerting anti-inflammatory effects in monocytes and/or macrophages and/or by enhancing glucose uptake in adipose and muscle. GPR120 is a membrane-bound receptor responsive to PUFAs which is preferentially expressed in adipose tissue and monocytes/macrophages. To decrease the medical burden of type 2 diabetes through enhanced glycemic control, GPR120 modulator compounds hold the promise of exerting a sensitizing effect to insulin as well as potential combination with a broad range of anti-diabetic drugs.

The present invention relates to novel phenylcycloalkyl and phenyl-azacycloalkyl carboxylic acid compounds which have the ability to modulate GPR120. Such compounds are therefore potentially useful for the treatment or prophylaxis of diabetes and related conditions.

SUMMARY OF THE INVENTION

The present invention provides phenylcycloalkyl and phenyl-azacycloalkyl carboxylic acid compounds, and their analogues thereof, which are useful as GPR120 modulators, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of multiple diseases or disorders associated with GPR120, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment of multiple diseases or disorders associated with GPR120.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

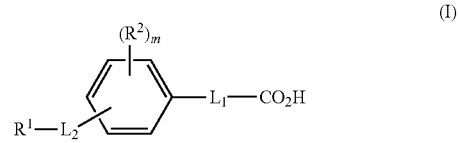

or a stereoisomer, a tautomer, a pharmaceutically acceptable salt, a polymorph, or a solvate thereof, wherein:

$L_1$ is independently a hydrocarbon linker substituted with 0-2 $R^a$, a hydrocarbon-heteroatom linker substituted with 0-2 $R^a$, or $-(O)_{0-1}-(CH_2)_{1-3}-(C_{3-4}$ cycloalkyl substituted with 0-2 $R^a)-(CH_2)_{0-2}-$; wherein said hydrocarbon linker has one to six carbon atoms and may be straight or branched, saturated or unsaturated; and said hydrocarbon-heteroatom linker has one to four carbon atoms and one group selected from O, CO, S, NH, CONH, and NHCO;

$L_2$ is independently selected from: a bond, O, S, $CH_2$, and $C(=O)$;

$R^1$ is independently selected from: $C_{3-8}$ cycloalkyl, $C_{5-8}$ cycloalkenyl, and 4- to 8-membered azacycloalkyl; wherein each moiety is substituted with 0-1 $R^3$ and 0-3 $R^4$;

$R^2$, at each occurrence, is independently selected from: halogen, $C_{1-6}$ alkyl, $C_{1-4}$ alkoxy, $C_{1-4}$ alkylthio, $C_{1-4}$ haloalkyl, $C_{1-6}$ haloalkoxy, and $C_{1-4}$ haloalkylthio;

$R^3$ is independently selected from: $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio and $-(X_1)_{0-1}-(CH_2)_{0-2}-R^5$;

X is independently selected from: O, S and NH;

$R^4$, at each occurrence, is independently selected from: halogen, and $C_{1-4}$ alkyl;

$R^5$ is independently selected from: $C_{3-6}$ carbocycle and a 5- to 6-membered heterocycle comprising carbon atoms and 1-4 heteroatoms selected from N, $NR^b$, O, and S; wherein said carbocycle and heterocycle are substituted with 0-3 $R^c$;

$R^a$, at each occurrence, is independently selected from: halogen, OH, $C_{1-4}$ alkyl, $C_{1-4}$ haloalkyl, and $C_{1-4}$ alkoxy;

$R^b$, at each occurrence, is independently selected from: H, $C_{1-4}$ alkyl, and $-(CH_2)_{0-2}$-phenyl;

$R^c$, at each occurrence, is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $CO_2(C_{1-4}$ alkyl), and COPh; and m is independently 0, 1, or 2.

In a second aspect, the present invention includes a compound of Formula (II):

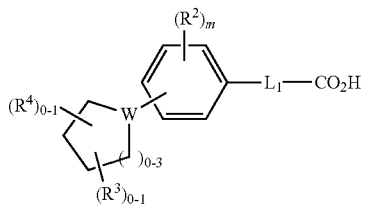

(II)

or a stereoisomer, a tautomer, a pharmaceutically acceptable salt, a polymorph, or a solvate thereof, within the scope of the first aspect.

In a third aspect, the present disclosure includes a compound of Formula (I) or (II), or a stereoisomer, a tautomer, a pharmaceutically acceptable salt, a polymorph, or a solvate thereof, within the scope of the first or second aspect, wherein:

$L_1$ is independently a hydrocarbon linker substituted with 0-1 $R^a$,
a hydrocarbon-heteroatom linker substituted with 0-1 $R^a$, or —$(O)_{0-1}$—$(CH_2)_{1-3}$—($C_{3-4}$ cycloalkyl substituted with 0-1 $R^a$)—$(CH_2)_{0-1}$—; wherein said hydrocarbon linker has one to six carbon atoms and may be straight or branched, saturated or unsaturated; and said hydrocarbon-heteroatom linker has one to four carbon atoms and O;

W is independently selected from: CH and N;

$R^2$, at each occurrence, is independently selected from: halogen, $C_{1-4}$ alkyl, and $C_{1-4}$ alkoxy;

$R^3$ is independently selected from: $C_{1-4}$ alkoxy, $C_{1-4}$ haloalkoxy, Bn, and —$(O)_{0-1}$—$R^5$;

$R^4$, at each occurrence, is independently selected from: halogen, and $C_{1-4}$ alkyl;

$R^5$ is independently selected from: $C_{3-6}$ cycloalkyl, phenyl, tetrahydropyranyl, oxadiazolyl, thiazolyl, pyridyl, and pyridazinyl; wherein each moiety is substituted with 0-2 $R^c$;

$R^a$, at each occurrence, is independently selected from: halogen, OH, $C_{1-4}$ alkyl, and $C_{1-4}$ alkoxy;

$R^c$, at each occurrence, is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $CO_2(C_{1-4}$ alkyl), and COPh; and m is independently 0, 1, or 2.

In a fourth aspect, the present invention includes a compound of Formula (III):

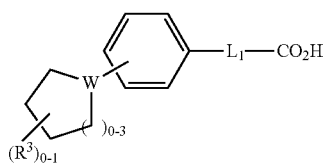

(III)

or a stereoisomer, a tautomer, a pharmaceutically acceptable salt, a polymorph, or a solvate thereof, within the scope of any of the above aspects.

In a fifth aspect, the present invention includes a compound of Formula (I), (II) or (III), or a stereoisomer, a tautomer, a pharmaceutically acceptable salt, a polymorph, or a solvate thereof, within the scope of any of the above aspects, wherein:

$L_1$ is independently a hydrocarbon linker substituted with 0-1 OH, a hydrocarbon-heteroatom linker or —$(O)_{0-1}$—$(CH_2)_{1-3}$-(cyclopropyl)-$(CH_2)_{0-1}$—; wherein said hydrocarbon linker has one to five carbon atoms and may be straight or branched, saturated or unsaturated; and said hydrocarbon-heteroatom linker has one to five carbon atoms and may be straight or branched, and has one to three carbon atoms and O.

In a sixth aspect, the present invention includes a compound of Formula (I), (II) or (III), or a stereoisomer, a tautomer, a pharmaceutically acceptable salt, a polymorph, or a solvate thereof, within the scope of any of the above aspects, wherein:

$L_1$ is independently selected from: $(CH_2)_{3-4}$, $(CH_2)_{2-3}OCH_2$,

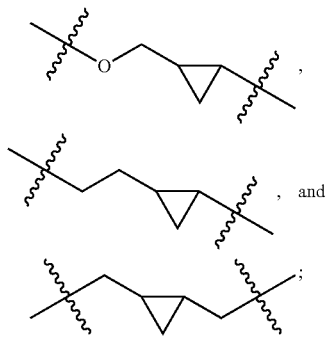

, and

;

$R^3$ is independently selected from: Bn, and —$(O)_{0-1}$—$R^5$;

$R^5$ is independently selected from: phenyl and pyridyl; wherein each moiety is substituted with 0-2 $R^c$; and $R^c$, at each occurrence, is independently selected from: halogen, CN, $C_{1-4}$ alkyl, $C_{1-4}$ alkoxy, $C_{1-4}$ haloalkyl, $C_{1-4}$ haloalkoxy, and $CO_2(C_{1-4}$ alkyl).

In another aspect, the present invention includes a compound of Formula (I), (II) or (III), or a stereoisomer, a tautomer, a pharmaceutically acceptable salt, a polymorph, or a solvate thereof, within the scope of any of the above aspects, wherein:

W is CH.

In another aspect, the present invention includes a compound of Formula (I), (II) or (III), or a stereoisomer, a tautomer, a pharmaceutically acceptable salt, a polymorph, or a solvate thereof, within the scope of any of the above aspects, wherein:

$L_2$ is a bond.

In a seventh aspect, the present invention provides a compound selected from the exemplified Examples 1 to 28 and 31 to 63 within the scope of the first aspect, or a stereoisomer, a tautomer, a pharmaceutically acceptable salt, a polymorph, or a solvate thereof.

In another aspect, the present invention provides a compound selected from any subset list of compounds within the scope of any of the above aspects.

In another embodiment, the compounds of the present invention have hGPR120 $EC_{50}$ values ≤10 µM.

In another embodiment, the compounds of the present invention have hGPR120 $EC_{50}$ values ≤5 µM.

In another embodiment, the compounds of the present invention have hGPR120 $EC_{50}$ values ≤1 µM.

In another embodiment, the compounds of the present invention have hGPR120 $EC_{50}$ values ≤0.5 µM.

II. Other Embodiments of the Invention

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, a polymorph, or a solvate thereof.

In another embodiment, the present invention provides a process for making a compound of the present invention or a stereoisomer, a tautomer, a pharmaceutically acceptable salt, a polymorph, or a solvate thereof.

In another embodiment, the present invention provides an intermediate for making a compound of the present invention or a stereoisomer, a tautomer, a pharmaceutically acceptable salt, a polymorph, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-pancreatitis agents, lipid lowering agents, anorectic agents and appetite suppressants.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin and alogliptin), a sodium-glucose transporter-2 (SGLT2) inhibitor (for example a member selected from dapagliflozin, canagliflozin, empagliflozin and remagliflozin), a GPR40/FFAR1 (Free fatty acid receptor 1) agonist (for example, TAK-875), and/or an MGAT2 (monoacylglycerol transferase 2) inhibitor (for example, compounds from WO 2012/124744, or compound (S)-10 from *Bioorg. Med. Chem. Lett.* (2013), doi: http://dx.doi.org/10.1016/j.bmcl.2013.02.084).

In a preferred embodiment, the present invention provides pharmaceutical composition, wherein the additional therapeutic agents are, for example, a dipeptidyl peptidase-IV inhibitor, a sodium-glucose transporter-2 inhibitor and an 11b-HSD-1 inhibitor.

In another embodiment, the present invention provides a method for the treatment of multiple diseases or disorders associated with GPR120, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the GPR120 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis.

In another embodiment, the present invention provides a method for the treatment of diabetes, hyperglycemia, gestational diabetes, obesity, dyslipidemia and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with GPR120.

In another embodiment, the present invention also provides the use of a compound of the present invention for the manufacture of a medicament for the treatment of multiple diseases or disorders associated with GPR120.

In another embodiment, the present invention provides a method for the treatment of multiple diseases or disorders associated with GPR120, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, linagliptin, vildagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with GPR120.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR120 receptor modulator of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin, alogliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, peliglitazar, tesaglitazar and aleglitazar), glucokinase activators (for example, PF-04937319 and AMG-151), GPR119 receptor modulators (for example, MBX-2952, PSN821, and APD597), sodium-glucose transporter-2 (SGLT2) inhibitors (for example, dapagliflozin, canagliflozin, empagliflozin and remagliflozin), GPR40 receptor agonists (e.g., TAK-875), amylin analogs such as pramlintide, and/or insulin.

The GPR120 receptor modulator of the present invention may also be optionally employed in combination with agents for treating complication of diabetes. These agents include PKC inhibitors and/or AGE inhibitors.

The GPR120 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 inhibitors and the like. The GPR120 receptor modulator of the present invention may also be employed in combination with an agonist of the glucagon-like peptide-1 receptor (GLP-1 R), such as exenatide, liraglutide, GLP-1(1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazolyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazolyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium (Ca$^{2+}$) ammonium (R$_n$NH$_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984);
f) Rautio, J. et al., *Nature Rev. Drug Discovery*, 7: 255-270 (2008); and
g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the esterper se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK, Second Edition (reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography and mass spectrometry, "HPLC" for high pressure liquid chromatography, "[M-H]" for parent mass minus a proton, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
AgOTf silver triflate
$CDCl_3$ deutero-chloroform
$CHCl_3$ chloroform
cDNA complimentary DNA
DEAD Diethyl azodicarboxylate
DIAD Diisopropyl azodicarboxylate
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or MeCN or ACN acetonitrile
$Cs_2CO_3$ cesium carbonate
HCl hydrochloric acid
$H_2SO_4$ sulfuric acid
$K_2CO_3$ potassium carbonate
KCN potassium cyanide
mCPBA or m-CPBA meta-chloroperbenzoic acid
Pd/C palladium on carbon
$PhSO_2Cl$ benzenesulfonyl chloride i-Pr$_2$Net Diisopropylethylamine
(Ph$_3$P)$_4$Pd Tetrakis(triphenylphosphine)Palladium
Ph$_3$P triphenylphosphine
PS polystyrene
SiO$_2$ silica oxide/silica gel
SnCl$_2$ tin(II) chloride
TEA triethylamine
TFA trifluoroacetic acid
TFAA trifluoroacetic anhydride
THF tetrahydrofuran
TMSCHN$_2$ Trimethylsilyldiazomethane
KOAc potassium acetate
Grubbs II (1,3-bis(2,4,6-trimethylphenyl)-2 imidazolidinyl-idene)dichloro(phenylmethylene) (tricyclohexylphosphine)ruthenium
MgSO$_4$ magnesium sulfate
MsCl methanesulfonyl chloride
MsOH or MSA methylsulfonic acid
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following Schemes and working Examples, as well as relevant published literature procedures that are used by one skilled in the art. Exemplary reagents and procedures for these reactions appear hereinafter and in the working Examples. Protection and de-protection in the processes below may be carried out by procedures generally known in the art (see, for example, Wuts, P. G. M. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*, Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

Scheme 1 describes the synthesis of aryloxycycloalkylphenylpentanoic acids 9 and 10. Phenylpentanoic acid is iodinated (HIO$_4$/I$_2$) followed by esterification to give the 4-iodophenylpentanoic acid ester 1. Palladium-catalyzed borylation (e.g., *J. Org. Chem.*, 60:7508 (1995)) of 1 with a bis-boronate ester 2 provided the corresponding phenyl boronate ester 3. Rhodium-catalyzed 1,4-conjugate addition (e.g., *Tetrahedron*, 68:1606 (2012)) of boronate 3 to an appropriate cyclo-2-alkenone 4 (n=1-3) provided the corresponding 3-aryl-substituted alkanones 5. Reduction (e.g., NaBH$_4$) of alkanones 5 provided the corresponding alcohols 6 as a mixture of isomers (S alcohol stereochemistry arbitrarily drawn in Scheme 1). Alcohols 6 are then reacted with substituted phenols 7 in a Mitsunobu reaction (*Chem. Rev.*, 109:2551 (2009)) with inversion of the alcohol stereochemistry to provide the corresponding aryl ether esters, which are deprotected to provide the desired aryloxy-cycloalkylphenylpentanoic acids 9. Alternatively, alcohols 6 undergo a copper-catalyzed coupling reaction with substituted aryl trifluoroborates 8 (e.g., *Org. Lett.*, 5:1381 (2003)) with retention of the alcohol stereochemistry, followed by ester deprotection to provide the desired aryloxy-cycloalkyl-phenylpentanoic acids 10.

Scheme 1

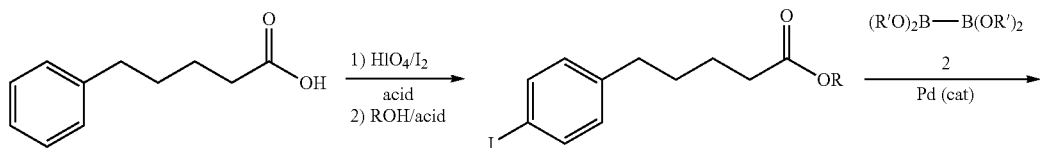

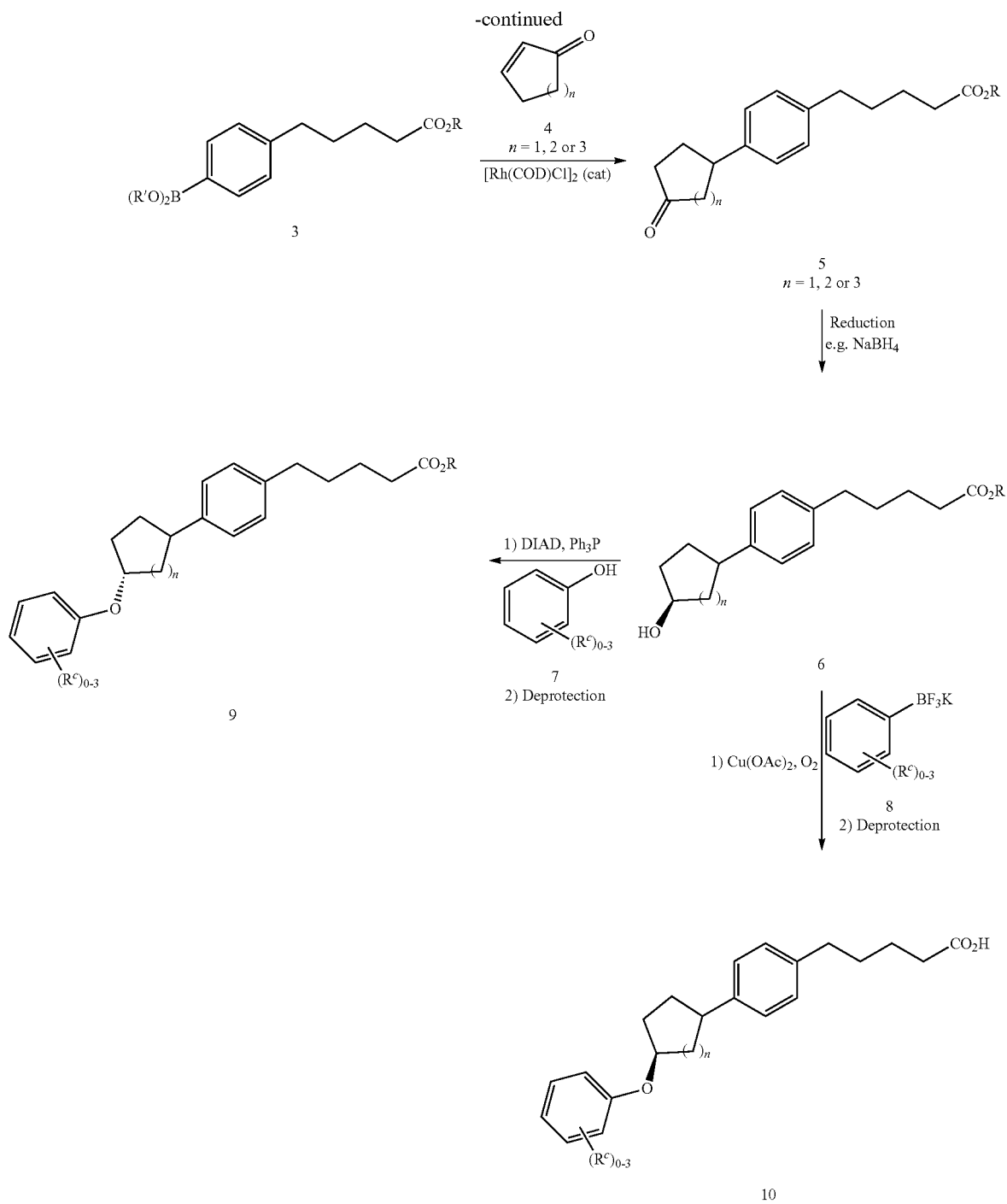

Scheme 2 describes the synthesis of aryloxy-cycloalkyl-phenyl-3-oxypentanoic acids 15 and 16. 4-Bromo-phenylethanol is alkylated with an appropriate α-bromoacetate ester 11 to provide oxyacetic acid ester 12. Palladium-catalyzed borylation (e.g., *J. Org. Chem.*, 60:7508 (1995)) of 12 with an appropriate bis-boronate ester 2 provided the corresponding phenyl boronate ester 13. Rhodium-catalyzed 1,4-conjugate addition (e.g., *Tetrahedron*, 68:1606 (2012)) of boronate 13 to an appropriate cyclo-2-alkenone 4 (n=1-3) followed by reduction (e.g., NaBH$_4$) provided the corresponding 3-aryl-substituted cycloalkanols 14 as a mixture of isomers (S alcohol stereochemistry arbitrarily drawn in Scheme 2). Alcohols 14 are then reacted with substituted phenols 7 in a Mitsunobu reaction (*Chem. Rev.*, 109:2551 (2009)) with inversion of the alcohol stereochemistry to provide the corresponding aryl ethers, which are deprotected to provide the desired aryloxy-cycloalkyl-phenyl-3-oxy-pentanoic acids 15. Alternatively, alcohols 14 undergo a copper-catalyzed coupling reaction with substituted aryl trifluoroborates 8 (e.g., *Org. Lett.*, 5:1381 (2003)) to give the corresponding aryl ethers (with retention of the alcohol stereochemistry) followed by ester deprotection to provide the desired aryloxy-cycloalkyl-phenyl-3-oxy-pentanoic acids 16.

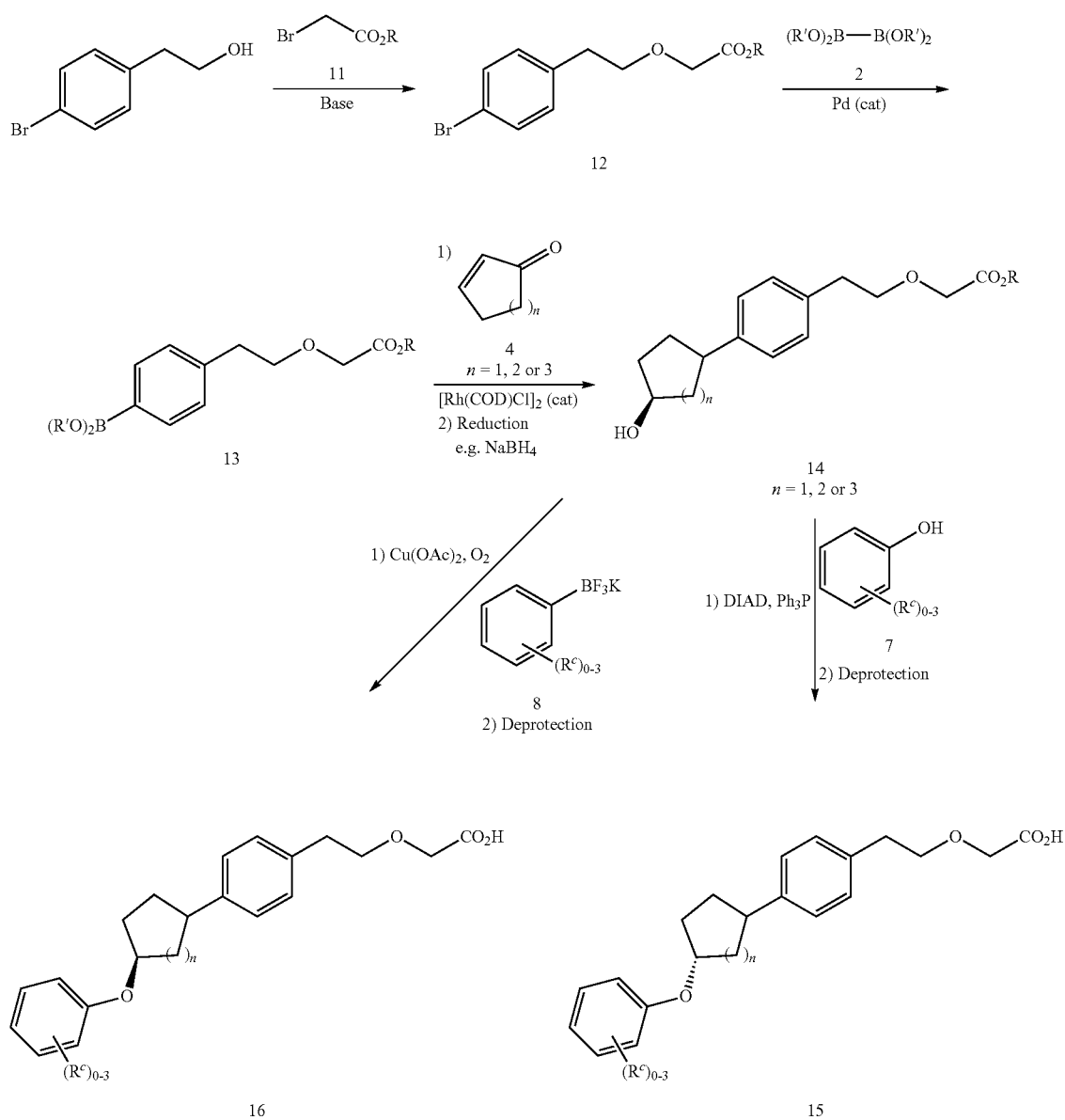

Scheme 3 describes the synthesis of (1R, 2R)-2-cyclopropane carboxylic acids 25 and 26. 4-Bromo-benzyl bromide is coupled with allyl magnesium chloride (e.g., WO 2008/001134, p. 73) to give the phenyl butene 17. Sharpless asymmetric dihydroxylation (e.g., *Organic Reactions*, 66:109-625 (2005)) using AD-mix-α (DHQ)$_2$PHAL as ligand) provides preferentially the (S) diol 18. Preferential reaction of diol 18 with p-toluenesulfonyl chloride (1 equivalent) at the primary alcohol provides the monotosylate 19, which undergoes intramolecular SN$_2$ displacement to give the (S)-epoxide 20 upon treatment with an appropriate base. Reaction of the (S)-epoxide 20 with an appropriate phosphonate ester 21 under basic conditions (e.g., *Org. Process Res. Dev.*, 6:618 (2002) and *Org. Biomol. Chem.*, 10:6987 (2012)) provides the (1R, 2R)-2-(4-bromophenethyl) cyclopropane carboxylic acid ester 22. Palladium-catalyzed borylation (e.g., *J. Org. Chem.*, 60:7508 (1995)) of bromide 22 with a bis-boronate ester 2 provided the corresponding phenyl boronate ester 23. Rhodium-catalyzed 1,4-conjugate addition (e.g., *Tetrahedron*, 68:1606 (2012)) of boronate 23 to an appropriate cyclo-2-alkenone 4 (n=1-3) followed by reduction (e.g., NaBH$_4$) provided the corresponding 3-aryl-substituted cycloalkanols 24 as a mixture of isomers (S alcohol stereochemistry arbitrarily drawn in Scheme 3). Alcohols 24 are then reacted with substituted phenols 7 in a Mitsunobu reaction (*Chem. Rev.*, 109:2551 (2009)) with inversion of the alcohol stereochemistry to provide the corresponding aryl ethers, which are deprotected to provide the desired (1R, 2R)-2-cyclopropane carboxylic acids 25. Alternatively, alcohols 24 undergo a copper-catalyzed coupling reaction with substituted aryl trifluoroborates 8 (e.g., *Org. Lett.*, 5:1381 (2003)) to give the corresponding aryl ethers (with retention of the alcohol stereochemistry) followed by ester deprotection to provide the desired (1R, 2R)-2-cyclopropane carboxylic acids 26.

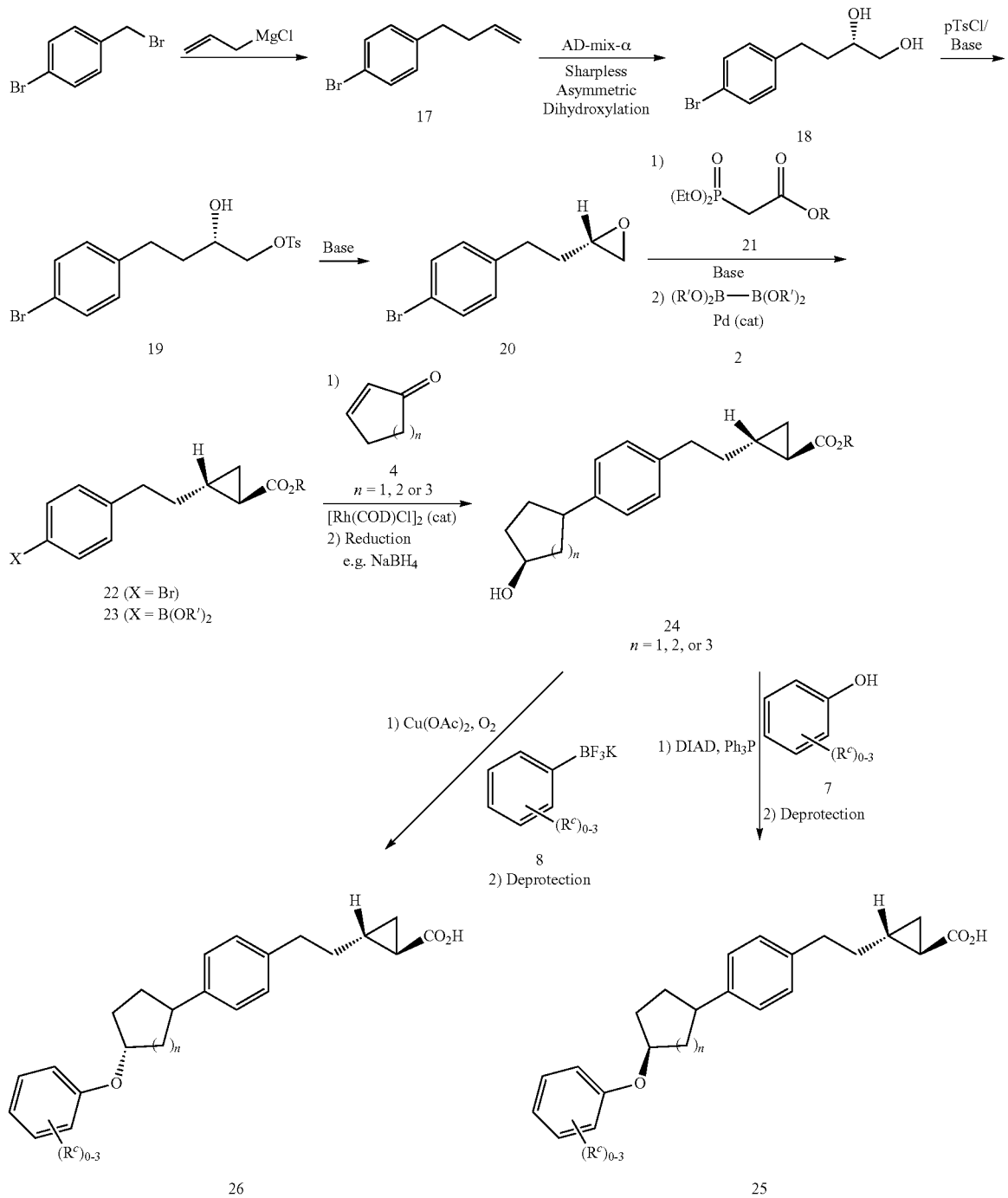

Scheme 4 shows the synthesis of the corresponding isomeric (1S, 2S)-2-cyclopropane carboxylic acids 31 and 32. Sharpless asymmetric dihydroxylation (e.g., *Organic Reactions*, 66:109-625 (2005)) of phenyl butene 17 using AD-mix-β [(DHQD)$_2$PHAL as ligand] provides preferentially the (R) diol 27. Preferential monotosylation of diol 18 with p-toluenesulfonyl chloride (1 equivalent) at the primary alcohol provides the mono-tosylate, which undergoes base-mediated intramolecular SN$_2$ displacement to give the (R)-epoxide 28. Reaction of the (R)-epoxide 28 with a phos- phonate ester 21 under basic conditions (e.g., *Org. Process Res. Dev.*, 6:618 (2002) and *Org. Biomol. Chem.*, 10:6987 (2012)) provides the (1S, 2S)-2-(4-bromophenethyl) cyclopropane carboxylic acid ester, which is converted to corresponding phenyl boronate 29 (e.g., *J. Org. Chem.*, 60:7508 (1995)). Rhodium-catalyzed 1,4-conjugate addition (e.g., *Tetrahedron*, 68:1606 (2012)) of boronate 29 to an appropriate cyclo-2-alkenone 4 (n=1-3) followed by reduction (e.g., NaBH$_4$) provided the corresponding 3-aryl-substituted cycloalkanols 30 as a mixture of isomers (S alcohol stereochemistry arbitrarily drawn in Scheme 4). Alcohols 30 are then reacted with substituted phenols 7 in a Mitsunobu reaction (*Chem. Rev.*, 109:2551 (2009)) with inversion of the alcohol stereochemistry to provide the corresponding aryl ethers, which are deprotected to provide the desired (1S, 2S)-2-cyclopropane carboxylic acids 31. Alternatively, alcohols 30 undergo a copper-catalyzed coupling reaction with substituted aryl trifluoroborates 8 (e.g., *Org. Lett.*, 5:1381 (2003)) to give the corresponding aryl ethers (with retention of the alcohol stereochemistry) followed by ester deprotection to provide the desired (1S, 2S)-2-cyclopropane carboxylic acids 32.

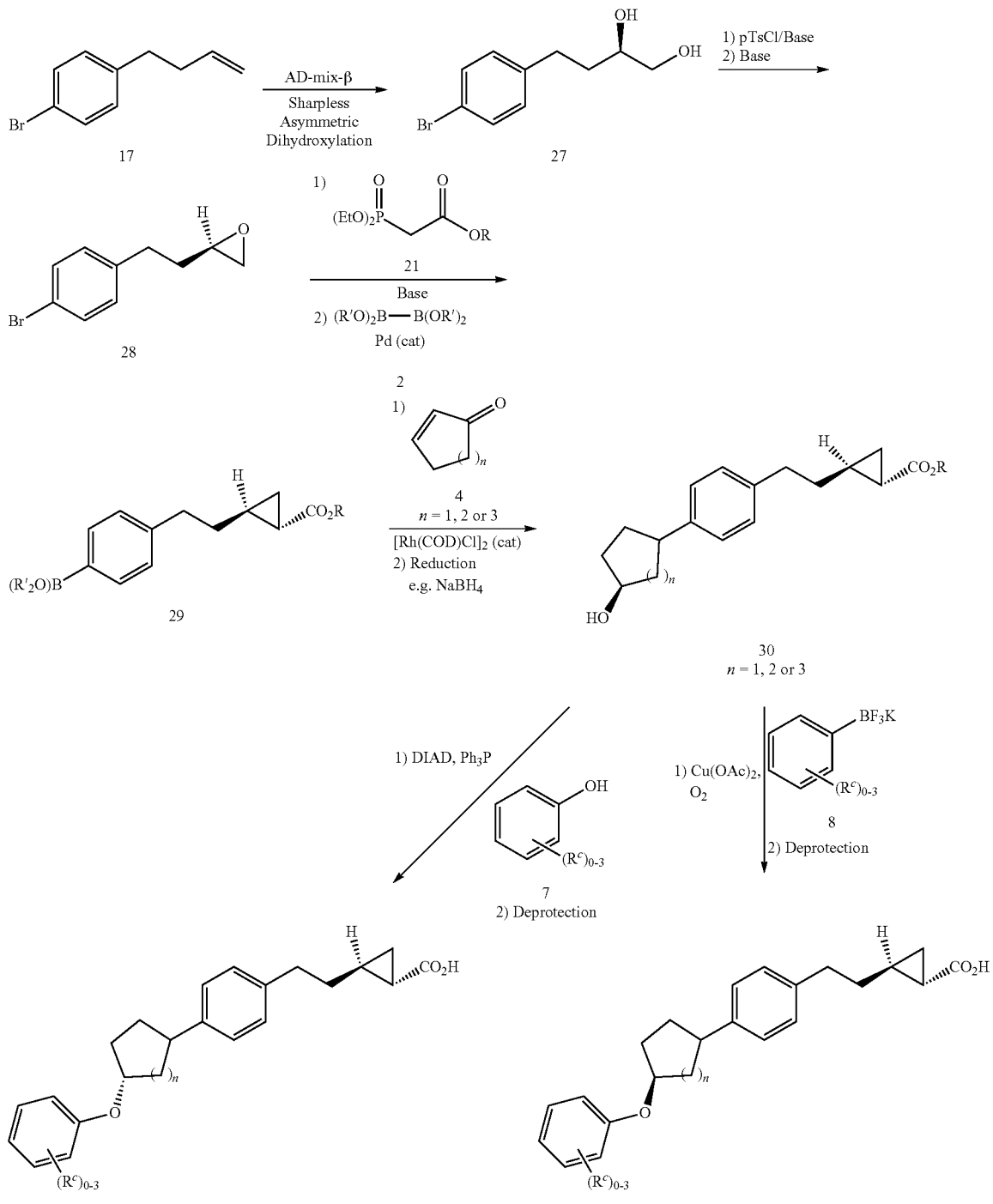

Scheme 4

Scheme 5 shows the synthesis of phenoxy(1S, 2S)-2-cyclopropane carboxylic acids 35, 36 and phenoxy(1R, 2R)-2-cyclopropane carboxylic acids 38 and 39. Reaction of 4-bromo-phenol with (S)-epichlorohydrin furnishes the (R)-epoxide 33. Reaction of (R)-epoxide 33 with a phosphonate ester 21 under basic conditions (e.g., Org. Process Res. Dev., 6:618 (2002) and Org. Biomol. Chem., 10:6987 (2012)) provides the phenoxy (1S, 2S)-2-cyclopropane carboxylic acid ester, which is converted to corresponding phenyl boronate 34 via Pd-mediated borylation (e.g., J. Org. Chem., 60:7508 (1995)). Phenyl boronate 34 is carried through the identical synthetic sequence as for the conversion of phenyl boronate 29 to isomeric aryl ether cyclopropyl acids 31 and 32 in Scheme 4 to provide the desired corresponding phenoxy (1S, 2S)-2-cyclopropane carboxylic acid isomers 35 and 36.

In an analogous manner, base-mediated reaction of 4-bromo-phenol with (R)-epichlorohydrin furnishes the corresponding (S)-epoxide 37. The (S)-epoxide 7 is then carried through the same synthetic sequence as used for the conversion of 33 to (1S, 2S)-2-cyclopropane carboxylic acids 35 and 36 to provide the desired phenoxy (1R, 2R)-2-cyclopropane carboxylic acid isomers 38 and 39.

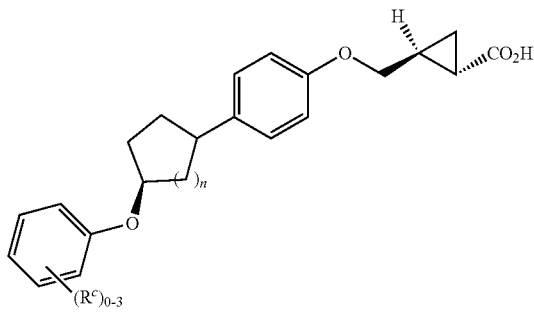

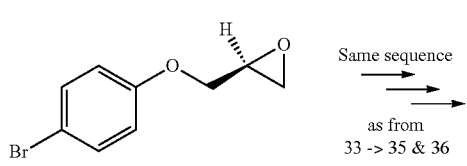

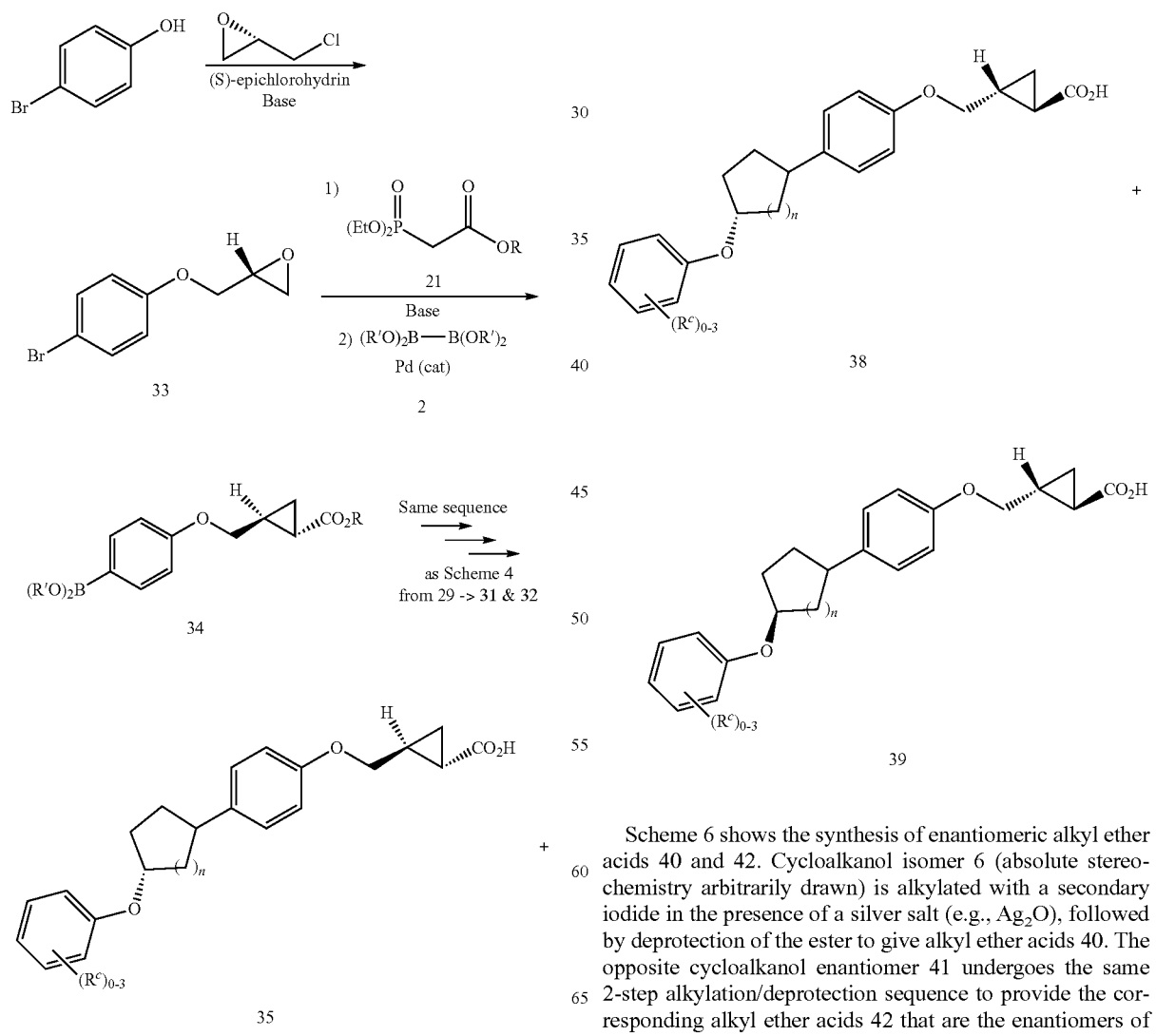

Scheme 6 shows the synthesis of enantiomeric alkyl ether acids 40 and 42. Cycloalkanol isomer 6 (absolute stereochemistry arbitrarily drawn) is alkylated with a secondary iodide in the presence of a silver salt (e.g., $Ag_2O$), followed by deprotection of the ester to give alkyl ether acids 40. The opposite cycloalkanol enantiomer 41 undergoes the same 2-step alkylation/deprotection sequence to provide the corresponding alkyl ether acids 42 that are the enantiomers of acids 40.

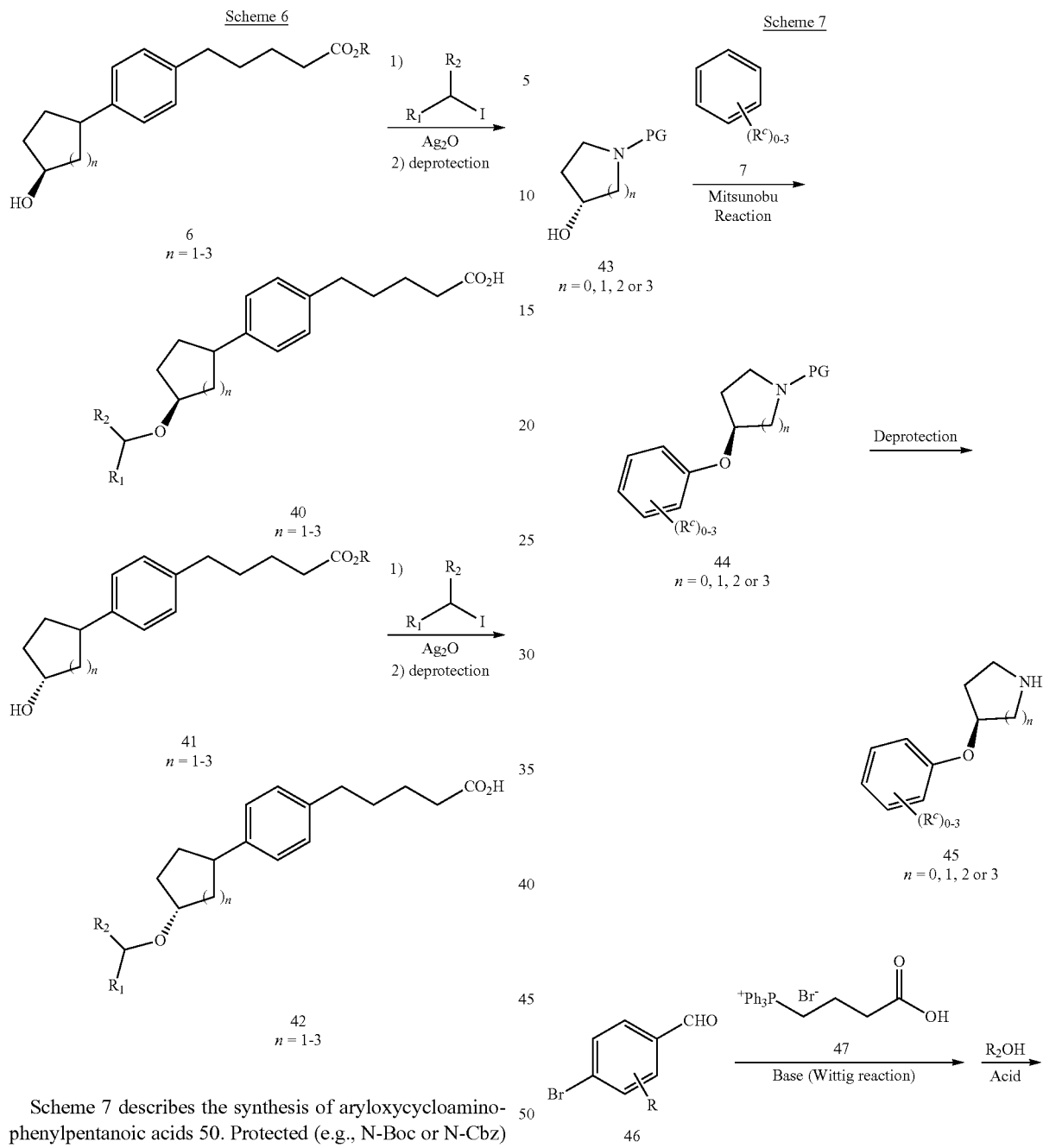

Scheme 7 describes the synthesis of aryloxycycloaminophenylpentanoic acids 50. Protected (e.g., N-Boc or N-Cbz) cycloalkylamine alcohols 43 (R configuration arbitrarily shown) undergo a Mitsunobu reaction (*Chem. Rev.*, 109: 2551 (2009)) with inversion of stereochemistry to give the corresponding aryl ethers 44, which are deprotected under acidic or hydrogenation conditions to give the aryl ether-cycloalkylamines 45. Aryl aldehydes 46 are reacted with an appropriate phosphonium salt 47 under Wittig conditions followed by protection of the carboxylic acid to furnish the aryl bromide ester 48. Aryl bromide 48 is reacted with cycloalkylamine 45 under Buchwald-Hartwig cross-coupling conditions (*Adv. Synth. Catalysis*, 346:1599 (2004)) to furnish the corresponding N-aryl cycloalkylamine 49, which then undergoes ester deprotection followed by alkene hydrogenation to provide the N-aryl cycloalkylamine acids 50.

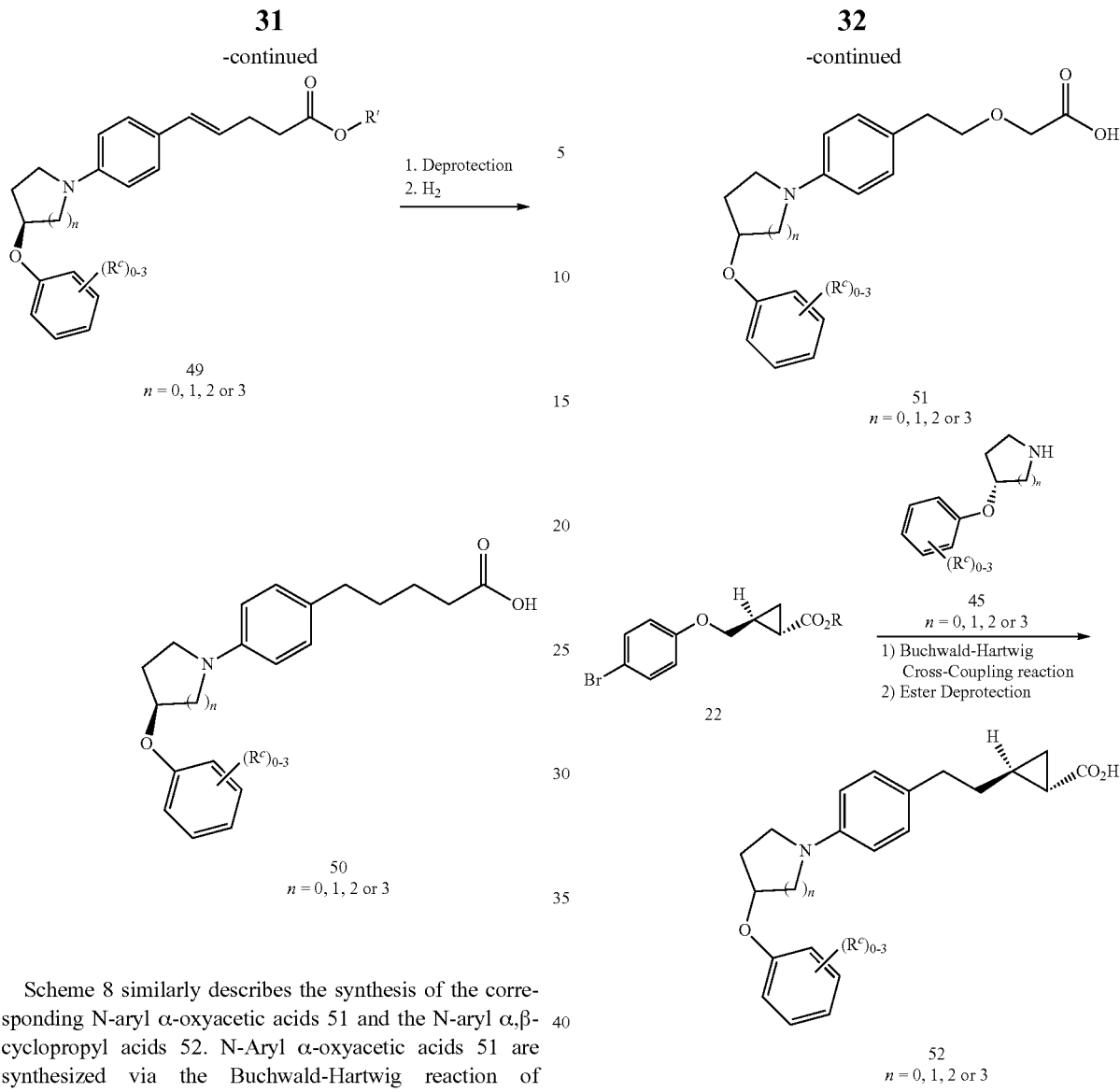

Scheme 8 similarly describes the synthesis of the corresponding N-aryl α-oxyacetic acids 51 and the N-aryl α,β-cyclopropyl acids 52. N-Aryl α-oxyacetic acids 51 are synthesized via the Buchwald-Hartwig reaction of cycloalkylamines 45 with the bromophenyl oxyacetic acid ester 12 followed by ester deprotection. Similarly, N-aryl α,β-cyclopropyl acids 52 are synthesized via the Buchwald-Hartwig reaction of cycloalkylamines 45 with bromo-phenyl α,β-cyclopropyl acid esters 22 followed by ester deprotection.

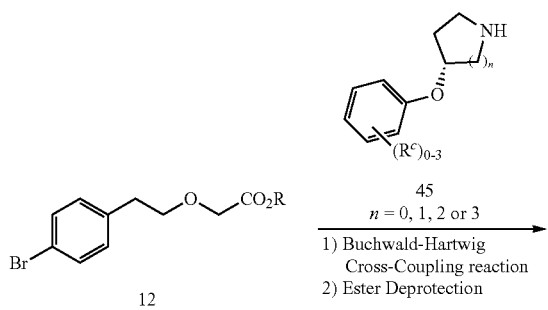

Scheme 9 describes the synthesis of 3-aryloxy azepanes 56 (cycloalkyl amines 45, where n=3). 1-Chloropent-4-en-2-ol is reacted with allyl amine and subsequent selective protection of the secondary amine (e.g., as N-Boc) provided the protected diene amino-alcohol 53. Olefin metathesis (*Tetrahedron*, 60:7117 (2004)) of diene 53 using e.g., Grubbs II catalyst furnishes the cycloalkenyl amine 54. Hydrogenation of the alkene provides the 3-hydroxyazepane 55, which undergoes a Mitsunobu reaction (*Chem. Rev.*, 109:2551 (2009)) with alcohol inversion followed by amine deprotection to furnish the desired 3-aryloxy azepanes 56.

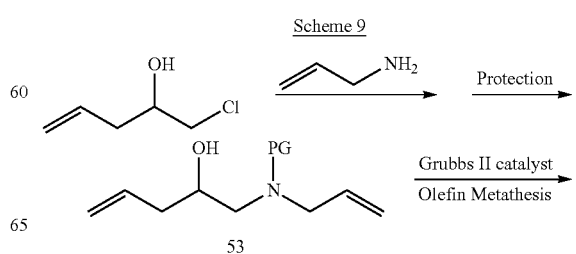

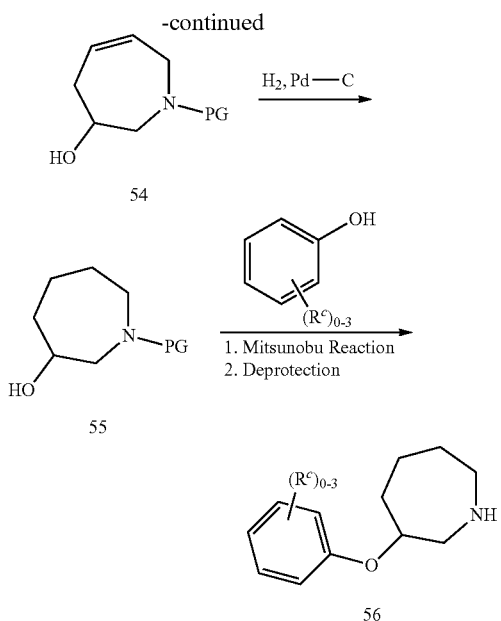

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for 1 cell secondary failure are not completely understood. Acquired pancreatic islet damage or exhaustion and/or genetic factors causing susceptibility to islet secretory insufficiency have been hypothesized.

Recently, five GPCRs (FFAR1 (GPR40), FFAR2 (GPR43), FFAR3 (GPR41), GPR84, and GPR120) were reported to recognize free fatty acids FFAR1, recognizes medium-long chainfatty acids like palmitic acid and linoleic acid FFAR2 and FFAR3 recognize short-chain fatty acids like acetate and butyrate whereas GPR84 recognizes medium-chain fatty acid like lauric acid. GPR120 recognizes long-chain fatty acids, especially EPA and DHA (Im, *Progress in Lipid Research,* 51:232-237(2012)). GPR120 has been detected in macrophages, dendritic cells, adipocytes, clara cells in bronchiole epithelium, and enteroendocrine L cells in colon (Miyauchi et al., *Naunyn-Schmiedebergs Arch Pharmacol.,* 379:427-434 (2009)). The anti-inflammatory mechanism of omega-3 fatty acids using GPR120 knock-out mice was investigated (Oh et al., *Cell,* 142:687-698 (2010)). They suggested GPR120 activation by DHA interacts with TAB1 via b-arrestin-2, and that this interaction interrupts TAK1 activation by LPS or TNF-alpha, suppressing inflammatory responses via NF-κB and JNK in macrophages and dendritic cells (Oh et al., *Cell,* 142:687-698 (2010)). Furthermore, GPR120 activation was shown to enhance insulin-induced glucose uptake in adipose tissues through Gq/11 proteins and PI 3-kinase.

Similarly, GPR120-deficient mice fed a high-fat diet develop obesity, glucose intolerance and fatty liver with decreased adipocyte differentiation and lipogenesis and enhanced hepatic lipogenesis (Ichimura et al., *Nature,* 483 (7389):350-354 (2012). Insulin resistance in such mice was shown to be associated with reduced insulin signalling and enhanced inflammation in adipose tissue. In humans, GPR120 expression in adipose tissue was shown to be significantly higher in obese individuals than in lean controls. GPR120 gene sequencing in obese subjects revealed a deleterious non-synonymous mutation (p.R270H) that inhibits GPR120 signalling activity. Furthermore, the p.R270H variant was associated with increased risk of obesity in European populations.

Given the increase in the worldwide patient population afflicted by type 2 diabetes, there is a need for novel therapies which are effective with minimal adverse events. To decrease medical burden of type 2 diabetes through enhanced glycemic control, GPR120 modulator compounds of the present invention are being investigated here for their ability to increase glucose tolerance as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR120 modulator. Exemplary subjects include human beings of any age with risk factors for metabolic disease. Common risk factors include, but are not limited to, age, sex, weight, family history, or signs of insulin resistance such as acanthosis *nigricans,* hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR120 and/or to prevent or treat the disorders listed herein. When applied to a combination, the term refers to combined amounts of the active ingredients that result in the preventive or therapeutic effect, whether administered in combination, serially, or simultaneously.

GPR120 activity was monitored by measuring phosphorylation of ERK (pERK), since G protein receptors are known to activate the ERK signaling cascade either directly and/or through recruitment of arrestin that serves as a scaffold for downstream signaling events. Molecules that activated GPR120 with sufficient potency and efficacy in the pERK assay that also possessed desirable pharmacokinetic properties were evaluated in mice for glucose lowering by monitoring disposition of an oral glucose load by an oral glucose tolerance test (oGTT).

GPR120 pERK AlphaScreen SureFire Assay

The human and mouse GPR120-mediated intracellular phosphorylated ERK assays were established using CHOA12 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029), 500 μg/mL GENETICIN® (Life Technologies Cat. #10131-027) and 250 μg/mL Zeocin (Invitrogen Cat. #R250-01). Cells were cryo preserved at a concentration of $2\times10^7$ cells/mL, in 90% Charcoal/Dextran FBS and 10% DMSO, and frozen in liquid nitrogen at a low passage number.

For the pERK assay, $2\times10^7$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.6\times10^6$ cells/mL. Cells were plated into 384-well clear bottom tissue culture plates (BD Cat. #353962) at 50 μL/well, for a density of 30,000 cells/well using a MULTI-DROP® and incubated for 16-18 hours (overnight) at 37° C. with 5% $CO_2$. The next day, cells were serum starved in 30 μL of F-12 media without any serum or antibiotics for 2 hours at 37° C.

Test compounds were 3-fold, 11-point serially diluted in DMSO in a REMP assay plate (Matrix Cat. #4307) by Tecan and 5 μL was transferred into an ECHO source plate (Labcyte Cat. #LC-0200). Cells were then stimulated with 50 nL of compound dilutions using ECHO liquid handler for 7 minutes at 37° C. Compounds ranged from final assay concentrations of 33.33 μM to 0.56 nM.

The media was then dumped and cells lysed with 20 μL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 μL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 μL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample−average blank)/(average total−average blank) where sample is the luminescence activity in the presence of test compound, blank is equal to the luminescence activity in the presence of DMSO control and the total is signal induced by 50 μM linolenic acid as reference compound. Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The human and mouse GPR120-mediated intracellular phosphorylated ERK assays were also established using CHO-K1 cells stably transfected with the short form of human or mouse GPR120 receptor. Cells were cultured in growth medium consisting of F-12 media (Invitrogen Cat. #11765) with 5% Charcoal/Dextran FBS (Invitrogen Cat. #12676-029) and 500 μg/mL GENETICIN® (Life Technologies Cat. #10131-027). Cells were cryo preserved at a concentration of $3\times10^6$ cells/mL, in 70% F-12, 20% Charcoal/Dextran FBS and 10% DMSO, and frozen in liquid nitrogen at a low passage number.

For the pERK assay, $3\times10^6$ cells/mL cryopreserved human and mouse cells were thawed rapidly in a 37° C. water bath and added to a T-225 flask containing 50 mL growth medium. The flasks were placed in a tissue culture incubator overnight (37° C., 5% $CO_2$). The next day, cells were harvested with trypsin (Gibco Cat. #25300-054), resuspended in serum-containing growth medium and counted using a Cellometer and volume adjusted to a concentration of $0.5\times10^6$ cells/mL. Cells were plated into 384-well clear bottom tissue culture plates (BD Cat. #353962) at 50 μL/well, for a density of 25,000 cells/well using a MULTI-DROP® and incubated for 16-18 hours (overnight) at 37° C. with 5% $CO_2$. The next day, cells were washed once with 50 μL of PBS without $Ca^{++}/Mg^{++}$ (Gibco Cat. #14190-036) and serum starved in 25 µL of F-12 media without any serum or antibiotics for 2 hours at 37° C.

Test compounds were 3-fold, 11-point serially diluted in DMSO in a REMP assay plate (Matrix Cat. #4307) by Tecan and 5 µL was transferred into an ECHO source plate (Labcyte Cat. #LC-0200). Cells were then stimulated with 40 nL of compound dilutions using ECHO liquid handler for 7 minutes at 37° C. Compounds ranged from final assay concentrations of 32 µM to 0.54 nM.

The media was then dumped and cells lysed with 20 µL of 1× Lysis buffer from the AlphaScreen SureFire Phospho-ERK 1/2 Kit (Perkin Elmer Cat. #6760617M). The lysis buffer was diluted 5-fold with water before use. The plate was agitated on a shaker for 10 minutes after which 2 µL was transferred into a 384-well white proxiplate (Perkin Elmer Cat. #6008289). The SureFire assay reagent mix was prepared by mixing 60 parts Reaction Buffer, 10 parts Activation Buffer, 1 part Donor Beads, 1 part Acceptor Beads (Perkin Elmer Cat. #TGRES10K). 3.5 µL/well of this reagent mix was manually added to the proxiplate with a multichannel pipettor. Plates were spun down at 1000 rpm for 2 minutes, followed by light-protected incubation at room temperature for 2 hours. The plates were read on the Alpha-technology compatible Envision multilabel plate reader using AlphaScreen protocol according to manufacturer's specifications. The agonist effect of compounds was expressed as 100×(average sample−average blank)/(average total−average blank) where sample is the luminescence activity in the presence of test compound, blank is equal to the luminescence activity in the presence of DMSO control and the total is signal induced by 50 µM linolenic acid as reference compound.

Activation data for the test compound over a range of concentrations was plotted as percentage activation of the test compound (100%=maximum response). After correcting for background, $EC_{50}$ values were determined. The $EC_{50}$ is defined as the concentration of test compound which produces 50% of the maximal response and was quantified using the 4 parameter logistic equation to fit the data.

The exemplified Examples disclosed below were tested in the GPR120 in vitro assays described above and were found having GPR120 agonist activity. Table 1 below lists the $EC_{50}$ values measured in the human GPR120 pERK assay for the following Examples.

| Example No. | $EC_{50}$ (µM) |
| --- | --- |
| 1 | 0.48 |
| 2 | 2.36 |
| 3 | 1.16 |
| 4 | 0.32 |
| 5 | 1.03 |
| 6 | 0.18 |
| 7 | 0.92 |
| 8 | 1.45 |
| 9 | 0.65 |
| 10 | 0.53 |
| 11 | 0.60 |
| 12 | 0.31 |
| 13 | 1.03 |
| 14 | 0.63 |
| 15 | 1.99 |
| 16 | 0.75 |
| 17 | 0.27 |
| 18 | 1.38 |
| 19 | 2.13 |
| 20 | 0.42 |
| 21 | 2.42 |
| 22 | 0.78 |
| 23 | 0.50 |
| 24 | 0.93 |
| 25 | 0.54 |
| 26 | 0.57 |
| 27 | 4.13 |
| 28 | 4.98 |
| 31 | 3.55 |
| 32 | 3.03 |
| 34 | 0.30 |
| 35 | 1.61 |
| 36 | 0.31 |
| 37 | 4.24 |
| 38 | 0.72 |
| 39 | 3.24 |
| 40 | 3.75 |
| 41 | 1.94 |
| 42 | >32 |
| 43 | >16 |
| 44 | 0.53 |
| 45 | 2.02 |
| 46 | 3.12 |
| 47 | 3.77 |
| 48 | 3.22 |
| 49 | 1.31 |
| 50 | 0.41 |
| 51 | 1.90 |
| 52 | 1.54 |
| 53 | 3.61 |
| 54 | 1.34 |
| 55 | 6.26 |
| 56 | 4.84 |
| 57 | 2.26 |
| 58 | 4.09 |
| 59 | 5.27 |
| 60 | 0.22 |
| 61 | 3.38 |
| 62 | 10.3 |
| 63 | 4.32 |

In Vivo GPR120 Assays

1) Acute Oral Glucose Tolerance Test

C57BL/6 mice were housed individually and fed a standard rodent chow diet. At approximately 11 weeks age, after a 5 h fast, these mice were orally treated with vehicle or test compounds 60 min before a glucose challenge (2 g/kg). Blood glucose levels were determined from tail bleeds taken at −60, 0, 15, 30, 60 and 120 min after the glucose challenge. The blood glucose excursion profile from t=0-120 min was used to calculate an area under the curve (AUC) for compound treatment. This AUC for compound treatment is compared to vehicle treatment.

2) Acute Intraperitoneal Insulin Tolerance Test

C57BL/6 mice were housed individually and fed a standard rodent chow diet. At approximately 11 weeks age, after 5 h fast, these mice were orally treated with vehicle or test compounds 30 min before an insulin challenge (0.1 U/kg). Blood glucose levels were determined from tail bleeds taken at −30, 0, 15, 30, 60, 90 and 120 min after insulin injection. The blood glucose excursion profile from t=0-120 min was used to calculate a negative area under the curve (AUC) for compound treatment. This AUC for compound treatment is compared to vehicle treatment.

The compounds of the present invention possess activity as modulators of GPR120, and, therefore, may be used in the treatment of diseases associated with GPR120 activity. Via modulation of GPR120, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, lipid disorders, lipodystrophy, liver diseases such as NASH (Non-Alcoholic SteatoHepatitis), NAFLD (Non-Alcoholic Fatty Liver Disease) and liver cirrhosis, and treatment of side-effects related to diabetes.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR120 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatitis agents, lipid lowering agents, anorectic agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR120 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR120 receptor modulators, or other antidiabetic agents. These agents include, but are not limited to, dipeptidyl peptidase IV (DP4) inhibitors (for example, sitagliptin, saxagliptin, linagliptin. alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, peliglitazar, tesaglitazar, aleglitazar), glucokinase activators (e.g., PF-04937319 and AMG-151, as well as other compounds described in Fyfe, M. C. T. et al., *Drugs of the Future,* 34(8):641-653 (2009) and incorporated herein by reference), GPR40 receptor modulators (e.g., TAK-875), GPR119 receptor modulators (e.g., MBX-2952, PSN821, APD597), other GPR120 receptor modulators (e.g., compound 43 from *J. Med. Chem.,* 55:4511-4515 (2012)), sodium-glucose transporter-2 (SGLT2) inhibitors (for example dapagliflozin, canagliflozin, remagliflozin), 11β-HSD-1 inhibitors (for example MK-0736, BI35585, BMS-823778, and LY2523199), amylin analogs such as pramlintide, and/or insulin. Reviews of current and emerging therapies for the treatment of diabetes can be found in: Mohler, M. L. et al., *Medicinal Research Reviews,* 29(1):125-195 (2009) and Mizuno, C. S. et al., *Current Medicinal Chemistry,* 15:61-74 (2008).

The GPR120 receptor modulator of the present invention may also be optionally employed in combination with agents for treating complication of diabetes. These agents include PKC inhibitors and/or AGE inhibitors.

The GPR120 receptor modulator of the present invention way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, MGAT2 (monoacylglycerol transferase 2) inhibitors (for example, compounds from WO 2012/124744, or compound (S)-10 from *Bioorg. Med. Chem. Lett.* (2013), doi: http://dx.doi.org/10.1016/j.bmcl.2013.02.084) and the like. The compound of structure I may also be employed in combination with an agonist of the glucagon-like peptide-1 receptor (GLP-1 R), such as exenatide, liraglutide, GLP-1(1-36) amide, GLP-1 (7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, D., *Nature Reviews: Drug Discovery,* 8:833-834 (2009); Obici, S., *Endocrinology,* 150(6):2512-2517 (2009); and Elangbam, C. S., *Vet. Pathol.,* 46(1):10-24 (2009).

The above other therapeutic agents, when employed in combination with the compounds of the present invention may be used, for example, in those amounts indicated in the *Physicians' Desk Reference,* as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR120 receptor. Such compounds may be provided in a commercial kit, for example, for use in pharmaceutical research involving GPR120 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR120.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with GPR120 (as defined previously). In another embodiment, the package insert states that the pharmaceutical composition can be used in combination (as defined previously) with a second therapeutic agent for the treatment of multiple diseases or disorders associated with GPR120. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples Analytical HPLC (unless otherwise noted) was performed to determine compound purity on a Shimadzu SIL-10A using the following method:

HPLC-1: SunFire C18 (4.6×150 mm) 3.5µ, gradient 10 to 100% B:A for 12 min, then 3 min hold at 100% B
Mobile Phase A: 0.05% TFA in water: $CH_3CN$ (95:5)
Mobile Phase B: 0.05% TFA in $CH_3CN$: water (95:5)
TFA Buffer pH=2.5
Flow rate: 1 mL/min
Wavelength: 254 nm, 220 nm
HPLC-2: XBridge Phenyl (4.6×150 mm) 3.5 t, gradient 10 to 100% B:A for 12 min, then 3 min hold at 100% B
Mobile Phase A: 0.05% TFA in water: $CH_3CN$ (95:5)
Mobile Phase B: 0.05% TFA in $CH_3CN$: water (95:5)
TFA Buffer pH=2.5
Flow rate: 1 mL/min
Wavelength: 254 nm, 220 nm NMR Employed in Characterization of Examples NMR (nuclear magnetic resonance) spectra were typically obtained on Bruker or JEOL® 400 MHz and 500 MHz instruments in the indicated solvents. All chemical shifts are reported in ppm from tetramethylsilane with the solvent resonance as the internal standard. $^1H$ NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

Spectral data are reported as chemical shift (multiplicity, number of hydrogens, coupling constants in Hz) and are reported in ppm (6 units) relative to either an internal standard (tetramethylsilane=0 ppm) for $^1H$ NMR spectra, or are referenced to the residual solvent peak (2.49 ppm for CD$_3$SOCD$_2$H, 3.30 ppm for CD$_2$HOD, 1.94 for CHD$_2$CN, 7.26 ppm for CHCl$_3$, 5.32 ppm for CDHCl$_2$).

Example 1

5-(4-((+/−)-3-Phenoxycyclohexyl)phenyl)pentanoic acid (cis-1,3-cyclohexyl isomer; Absolute Stereochemistry is Arbitrarily Drawn)

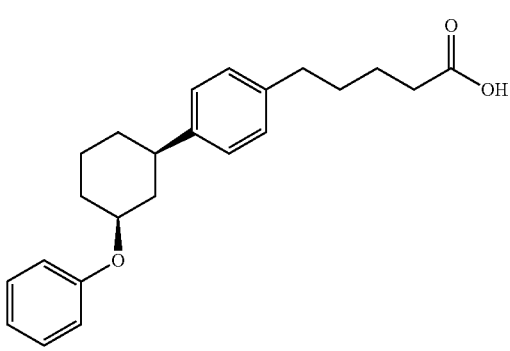

1A. 5-(4-Iodophenyl)pentanoic acid

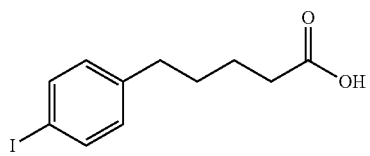 [SMILES: O=C(O)CCCCc1ccc(I)cc1]

The title compound was synthesized according to the procedure described by Gibson, S. E. et al. (*Tetrahedron*, 60:6945 (2004)). 5-Phenylpentanoic acid (20 g, 112 mmol), periodic acid (5.12 g, 22.4 mmol), and iodine (11.4 g, 44.9 mmol) were reacted with conc H$_2$SO$_4$ (3.68 mL) and AcOH (121 mL) in water (24 mL) to afford the title compound (16.8 g, 55.2 mmol, 49% yield) as a white solid. $^1$H NMR (400 MHz, CDCl$_3$) δ 7.85-7.39 (m, 2H), 7.08-6.72 (m, 2H), 2.58 (t, J=7.0 Hz, 2H), 2.41-2.25 (m, 2H), 1.80-1.52 (m, 4H).

1B. Methyl 5-(4-iodophenyl)pentanoate

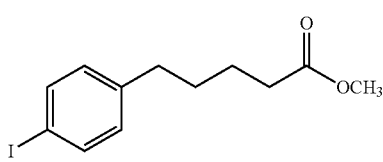 [SMILES: COC(=O)CCCCc1ccc(I)cc1]

HCl (g) was bubbled through a −78° C. mixture of 5-(4-iodophenyl)pentanoic acid (5.70 g, 18.7 mmol) and MeOH (50 mL) for 5 min. The reaction was allowed to warm to rt overnight and stirred under Ar. Volatiles were removed in vacuo and the residue was dissolved in EtOAc (100 mL) and washed with sat. aq. NaHCO$_3$ and brine, then dried (Na$_2$SO$_4$) and concentrated in vacuo. The residue was chromatographed (SiO$_2$; 10 g; 4:1 Hex:EtOAc), to afford the title compound (5.88 g, 18.48 mmol, 99% yield) as a pale yellow oil. $^1$H NMR (500 MHz, CDCl$_3$) δ 7.74-7.43 (m, 2H), 7.03-6.78 (m, 2H), 3.66 (s, 3H), 2.57 (t, J=7.2 Hz, 2H), 2.32 (t, J=7.2 Hz, 2H), 1.79-1.49 (m, 4H).

1C. Methyl 5-(4-(4,4,5,5-tetramethyl-1,3,2-dioxaborolan-2-yl)phenyl)pentanoate

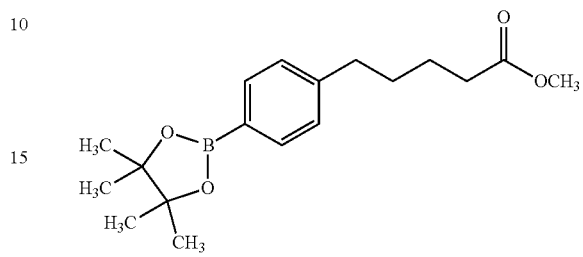

A mixture of methyl 5-(4-iodophenyl)pentanoate (5.88 g, 18.48 mmol), 4,4,4',4',5,5,5',5'-octamethyl-2,2'-bi(1,3,2-dioxaborolane) (5.63 g, 22.2 mmol), KOAc (5.44 g, 55.4 mmol) in DMSO (61.6 ml) was degassed and purged with Ar for 15 min, after which PdCl$_2$(dppf) (1.35 g, 1.85 mmol) was added and the mixture was degassed and purged for 15 min. The reaction mixture was heated at 85° C. under Ar overnight, then was cooled to rt and filtered; the filtrate was diluted with water (250 mL) and extracted with EtOAc (2×100 mL). The combined organic extracts were washed with brine, dried (Na$_2$SO$_4$) and concentrated in vacuo. The residue was chromatographed (SiO$_2$; 120 g; A=Hex, B=EtOAc; 30 min gradient from 100% hexane to 50:50 hexane:EtOAc; flow rate=80 mL/min) to afford the title compound (5.9 g, 18.5 mmol, 100% yield) as a colorless oil. $^1$H NMR (500 MHz, CDCl$_3$) δ 7.72 (d, J=8.0 Hz, 2H), 7.18 (d, J=8.0 Hz, 2H), 3.65 (s, 3H), 2.64 (s, 2H), 2.32 (s, 2H), 1.76-1.61 (m, 4H), 1.33 (s, 12H).

1D. (4-(5-Methoxy-5-oxopentyl)phenyl)boronic acid

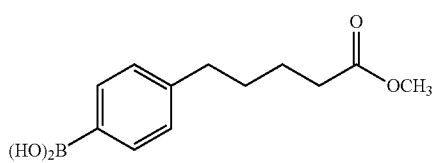 [SMILES: COC(=O)CCCCc1ccc(B(O)O)cc1]

To a mixture of methyl 5-(4-(4,4,5,5-tetramethyl-1,3,2-dioxaborolan-2-yl) phenyl)pentanoate (5.9 g, 18.5 mmol) and acetone (250 mL) was added a solution of NH$_4$OAc (4.29 g, 55.6 mmol) in water (250 mL), followed by NaIO$_4$ (11.90 g, 55.6 mmol). The reaction was stirred overnight at rt and most of the volatiles were removed in vacuo. The resultant aqueous phase was acidified with 1 N aq HCl and extracted with EtOAc (2×100 mL). The combined organic extracts were washed with brine, dried (Na$_2$SO$_4$) and concentrated in vacuo. The residue was chromatographed (SiO$_2$; 40 g; A=Hex, B=EtOAc; 20 min gradient from 100% A to 100% B; flow rate=40 mL/min) to afford the title compound (2.6 g, 11.0 mmol, 59.4% yield) as a pale yellow oil.

$^1$H NMR (500 MHz, CDCl$_3$) δ 8.14 (d, J=8.0 Hz, 2H), 7.31 (d, J=8.0 Hz, 2H), 3.76-3.56 (m, 3H), 2.81-2.65 (m, 2H), 2.36 (t, J=6.9 Hz, 2H), 1.78-1.61 (m, 4H).

1E. Methyl 5-(4-(3-oxocyclohexyl)phenyl)pentanoate

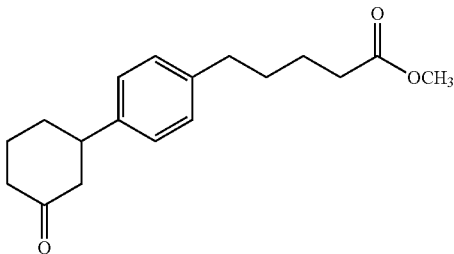 [SMILES: COC(=O)CCCCc1ccc(C2CCCC(=O)C2)cc1]

A mixture of (4-(5-methoxy-5-oxopentyl)phenyl) boronic acid (0.65 g, 2.75 mmol), cyclohex-2-enone (0.265 g, 2.75 mmol) and Na$_2$CO$_3$ (0.584 g, 5.51 mmol) in water (3.44 ml) was flushed with Ar, after which chloro(1,5-cyclooctadiene) rhodium(I) dimer (0.027 g, 0.055 mmol) was added and the mixture was flushed again with Ar. The sealed reaction vial was heated at 80° C. for 18 h, then cooled to rt and diluted with water (10 mL) and extracted with DCM (2×5 mL). The combined organic extracts were washed with brine, dried (Na$_2$SO$_4$) and concentrated in vacuo. The residue was chromatographed (SiO$_2$; 40 g; A=Hex, B=EtOAc; 15 min gradient from 0% B to 50% B; flow rate=12 mL/min; fractions with product were identified by TLC using PMA stain) to afford the title compound (0.7 g, 2.43 mmol, 88% yield) as a pale yellow oil.

$^1$H NMR (500 MHz, CDCl$_3$) δ 7.21-7.02 (m, 4H), 3.66 (s, 3H), 3.07-2.90 (m, 1H), 2.65-2.55 (m, 3H), 2.54-2.50 (m, 1H), 2.49-2.42 (m, 1H), 2.41-2.36 (m, 1H), 2.33 (t, J=7.2 Hz, 2H), 2.14 (ddd, J=9.7, 6.4, 3.2 Hz, 1H), 2.10-2.02 (m, 1H), 1.90-1.73 (m, 2H), 1.72-1.63 (m, 4H).

1F. Methyl 5-(4-((+/−)-3-hydroxycyclohexyl)phenyl)pentanoate (Diastereomer 1; Absolute Stereochemistry is Arbitrarily Drawn)

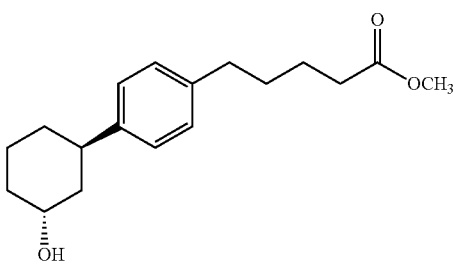 [SMILES: COC(=O)CCCCc1ccc([C@@H]2CCC[C@@H](O)C2)cc1]

and

1G. Methyl 5-(4-((+/−)-3-hydroxycyclohexyl)phenyl)pentanoate (Diastereomer 2; Absolute Stereochemistry is Arbitrarily Drawn)

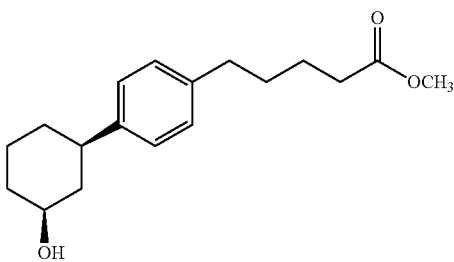 [SMILES: COC(=O)CCCCc1ccc([C@@H]2CCC[C@H](O)C2)cc1]

To a solution of methyl 5-(4-(3-oxocyclohexyl)phenyl) pentanoate 1E (0.70 g, 2.43 mmol) in MeOH (48.5 mL) was added NaBH$_4$ (0.037 g, 0.97 mmol) and the reaction was stirred at rt under Ar overnight. The reaction mixture was quenched with water (100 mL) and extracted with EtOAc (2×50 mL). The combined organic extracts were washed with brine, dried (Na$_2$SO$_4$) and concentrated in vacuo. The residue was chromatographed (SiO$_2$; 12 g; A=Hex, B=EtOAc; 15 min gradient from 0% B to 50% B; flow rate=12 mL/min; fractions containing product were identified by TLC using PMA stain).

The fractions containing the faster eluting diastereomer yielded the title compound 1F (0.17 g, 0.585 mmol, 24.1% yield) as a colorless oil. $^1$H NMR (500 MHz, CD$_3$OD) δ 7.21-6.99 (m, 4H), 4.20-4.11 (m, 1H), 3.65 (s, 3H), 3.03-2.90 (m, 1H), 2.59 (t, J=7.0 Hz, 2H), 2.40-2.25 (m, 2H), 2.00-1.76 (m, 4H), 1.73-1.42 (m, 8H).

The fractions containing the slower eluting diastereomer yielded the title compound 1G (0.40 g, 1.38 mmol, 56.7% yield) as a colorless oil. $^1$H NMR (500 MHz, CDCl$_3$) δ 7.23-7.00 (m, 4H), 3.76-3.57 (m, 4H), 2.68-2.50 (m, 3H), 2.42-2.27 (m, 2H), 2.15-2.08 (m, 1H), 2.02 (d, J=13.2 Hz, 1H), 1.93-1.84 (m, 1H), 1.77 (d, J=12.7 Hz, 1H), 1.71-1.55 (m, 4H), 1.52-1.18 (m, 4H).

Example 1

To a 0° C. mixture of methyl 5-(4-((+/−)-3-hydroxycyclohexyl)phenyl) pentanoate (1F, diastereomer 1; absolute stereochemistry arbitrarily drawn; 80 mg, 0.275 mmol), phenol (51.9 mg, 0.551 mmol) and Ph$_3$P (145 mg, 0.551 mmol) in THF (2 mL) was added dropwise DIAD (0.107 mL, 0.551 mmol) over 10 min. The reaction was allowed to slowly warm to rt overnight under Ar, then was concentrated in vacuo. The residue was chromatographed (SiO$_2$; 24 g; A=Hex, B=EtOAc; 15 min gradient from 0% B to 40% B; flow rate=24 mL/min; TLC R$_f$=0.65; 4:1 Hex:EtOAc). This material was dissolved in KOH (2 mL of a 2 N solution in MeOH) and water (1 drop), and stirred at rt for 2 h. The reaction was acidified with 1 N aq HCl (10 mL) and extracted with EtOAc (2×5 mL). The combined organic extracts were washed with brine, dried (Na$_2$SO$_4$) and concentrated in vacuo. The residue was purified by preparative HPLC (Column: Waters XBridge C18, 19×200 mm, 5-μm particles; Mobile Phase A: 5:95 MeCN: water with 10 mM NH$_4$OAc; Mobile Phase B: 95:5 MeCN: water with 10 mM NH$_4$OAc; Gradient from 65:35 A:B to 30:70 A:B over 20 min, then 5 min hold at 100% B; flow rate=20 mL/min) to afford the title compound (24.7 mg, 0.068 mmol, 24.7% yield) as a colorless oil. $^1$H NMR (500 MHz, DMSO-d$_6$) δ 7.27 (t, J=8.0 Hz, 2H), 7.18-7.14 (m, 2H), 7.13-7.08 (m, 2H), 6.96 (d, J=8.5 Hz, 2H), 6.90 (s, 1H), 4.50-4.37 (m, 1H), 2.76-2.63 (m, 1H), 2.58-2.51 (m, 2H), 2.22 (t, J=7.0 Hz, 2H), 2.19-2.10 (m, 2H), 1.92-1.83 (m, 1H), 1.81-1.71 (m, 1H), 1.61-1.46 (m, 6H), 1.43-1.26 (m, 2H).

Example 2

5-(4-((+/−)-3-Phenoxycyclohexyl)phenyl)pentanoic acid (trans-1,3-cyclohexy isomer; Absolute Stereochemistry is Arbitrarily Drawn)

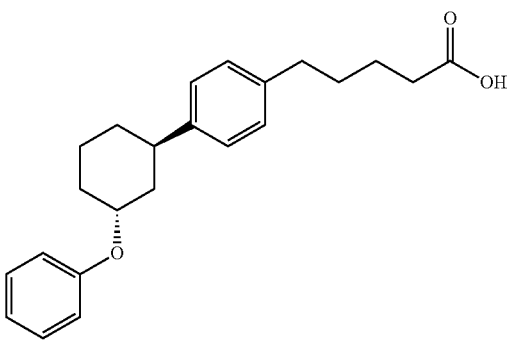 [SMILES: O=C(O)CCCCc1ccc([C@@H]2CCC[C@@H](Oc3ccccc3)C2)cc1]

Example 2 was synthesized from methyl 5-(4-((+/−)-3-hydroxycyclohexyl)phenyl) pentanoate 1G (diastereomer 2; absolute stereochemistry arbitrarily drawn) using the same synthetic sequence as for the synthesis of Example 1 from Intermediate 1F, to afford the title compound (2.6 mg, 7.3 μmol, 2.7% yield) as a colorless residue. $^1$H NMR (500 MHz, DMSO-$d_6$) δ 7.34-7.25 (m, 2H), 7.11 (d, J=7.2 Hz, 4H), 7.04-6.97 (m, 2H), 6.96-6.88 (m, 1H), 4.82-4.74 (m, 1H), 2.99-2.87 (m, 2H), 2.57-2.52 (m, 2H), 2.23-2.16 (m, 2H), 2.08-1.93 (m, 2H), 1.86-1.68 (m, 3H), 1.66-1.43 (m, 6H).

Example 3

5-(4-((+/−)-3-Isopropoxycyclohexyl)phenyl)pentanoic acid (cis-1,3-cyclohexyl isomer, Absolute Stereochemistry is Arbitrarily Drawn)

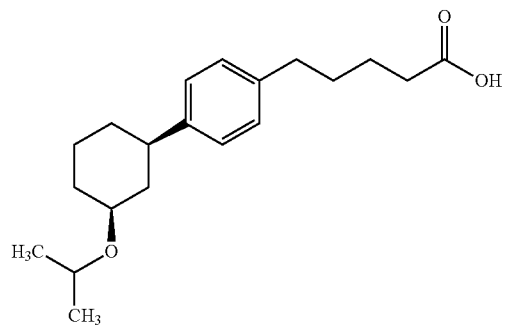 [SMILES: CC(C)O[C@H]1CCC[C@@H](c2ccc(CCCCC(=O)O)cc2)C1]

A mixture of methyl 5-(4-((+/−)-3-hydroxycyclohexyl)phenyl)pentanoate 1G (diastereomer 2; absolute stereochemistry is arbitrarily drawn) (28 mg, 0.096 mmol), 2-iodopropane (481 μL, 4.82 mmol) and silver(I) oxide (44.7 mg, 0.193 mmol) was stirred under Ar in the dark (reaction covered with Al foil) for 6 days. Analytical HPLC showed the formation of the desired product (longer retention time peak) in addition to a small amount of starting material. Volatiles were removed in vacuo to provide the desired isopropyl ether product, which was used in the next step without further purification.

A mixture of the isopropyl ether ester product, KOH (1 mL of a 2 N solution in MeOH) and water (3 drops) was stirred at rt for 3 h, then was diluted with 10% aq. citric acid (10 mL) and extracted with EtOAc (2×5 mL). The combined organic extracts were washed with brine, dried (Na$_2$SO$_4$) and concentrated in vacuo. The residue was purified by preparative HPLC (continuous gradient from 80% A:20% B to 100% B; A=10% MeCN/90% H$_2$O+0.1% TFA; B=90% MeCN/10% H$_2$O+0.1% TFA; detection at 220 nm; 10 min gradient; PHENOMENEX® Axia 5μ C18, 30×100 mm) to give the title compound (14.3 mg, 0.043 mmol, 44.6% yield) as a colorless oil. $^1$H NMR (500 MHz, CDCl$_3$) δ 7.19-7.02 (m, 4H), 3.75 (quin, J=6.1 Hz, 1H), 3.41 (tt, J=10.9, 4.1 Hz, 1H), 2.60 (t, J=7.0 Hz, 2H), 2.51 (tt, J=12.2, 3.3 Hz, 1H), 2.37 (t, J=6.9 Hz, 2H), 2.19-2.10 (m, 1H), 2.08-1.97 (m, 1H), 1.92-1.84 (m, 1H), 1.83-1.76 (m, 1H), 1.72-1.60 (m, 4H), 1.52-1.21 (m, 4H), 1.16 (s, 6H).

Example 4

2-(4-((+/−)-3-Phenoxycyclohexyl)phenethoxy)acetic acid (racemic cis-1,3-cyclohexyl isomer; Absolute Stereochemistry is Arbitrarily Drawn)

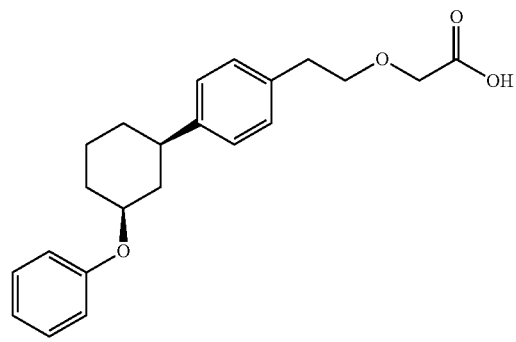

4A. tert-Butyl 2-(4-bromophenethoxy)acetate

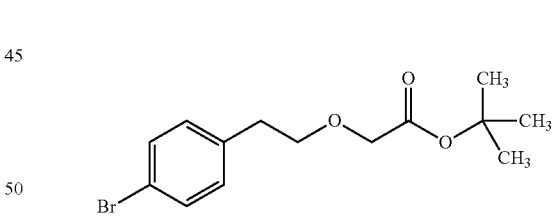

To a solution of 2-(4-bromophenyl)ethanol (10 g, 49.7 mmol) in toluene (300 mL) was added Bu$_4$NCl.H$_2$O (7.36 g, 24.87 mmol). The mixture was cooled to 0° C., then NaOH (30% w/v aq.; 83 mL, 622 mmol) and tert-butyl 2-bromoacetate (11.0 mL, 74.6 mmol) were successively added. The reaction mixture was stirred vigorously overnight at rt, after which the aqueous phase was extracted with EtOAc (50 mL). The combined organic phases were washed with brine, dried (Na$_2$SO$_4$) and concentrated in vacuo. The residue was chromatographed (SiO$_2$; 80 g; A=Hex, B=EtOAc; 20 min gradient from 0% B to 50% B; flow rate=60 mL/min) to afford the title compound (11.6 g, 36.8 mmol, 74.0% yield) as a colorless oil. $^1$H NMR (500 MHz, CDCl$_3$) δ 7.46-7.34 (m, 2H), 7.12 (d, J=8.3 Hz, 2H), 3.95 (s, 2H), 3.72 (t, J=7.0 Hz, 2H), 2.89 (t, J=7.0 Hz, 2H), 1.53-1.41 (m, 9H).

4B. tert-Butyl 2-(4-(5,5-dimethyl-1,3,2-dioxaborinan-2-yl)phenethoxy)acetate

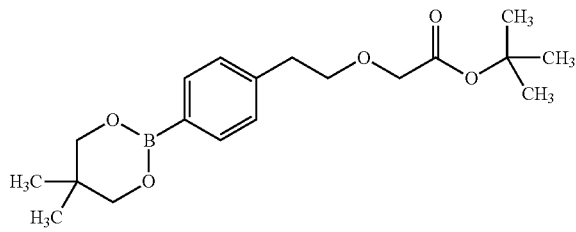 [SMILES: CC1(C)COB(c2ccc(CCOCC(=O)OC(C)(C)C)cc2)OC1]

A mixture of tert-butyl 2-(4-bromophenethoxy)acetate (11.6 g, 36.8 mmol), 5,5,5',5'-tetramethyl-2,2'-bi(1,3,2-dioxaborinane (9.98 g, 44.2 mmol), KOAc (10.84 g, 110 mmol) and DMSO (147 mL) was purged and flushed with Ar, after which PdCl$_2$(dppf) (1.346 g, 1.84 mmol) was added. The mixture was purged and flushed again with Ar and was stirred at 85° C. under Ar overnight, then cooled to rt and filtered. The filtrate was partitioned between water (300 mL) and EtOAc (150 mL) and the aqueous phase was extracted with EtOAc (150 mL). The combined organic extracts were washed with brine, dried (Na$_2$SO$_4$) and concentrated in vacuo. The residue was chromatographed (SiO$_2$; 120 g; A=Hex, B=EtOAc; 30 min gradient from 0% B to 60% B; flow rate=80 mL/min) to afford the title compound (10.06 g, 28.9 mmol, 78% yield) as a white solid.
$^1$H NMR (400 MHz, CDCl$_3$) δ 7.65 (d, J=7.5 Hz, 2H), 7.30-6.93 (m, 2H), 3.88 (s, 2H), 3.75-3.54 (m, 6H), 2.88 (t, J=7.3 Hz, 2H), 1.40 (s, 9H), 0.94 (s, 6H).

4C. tert-Butyl 2-(4-(3-oxocyclohexyl)phenethoxy)acetate

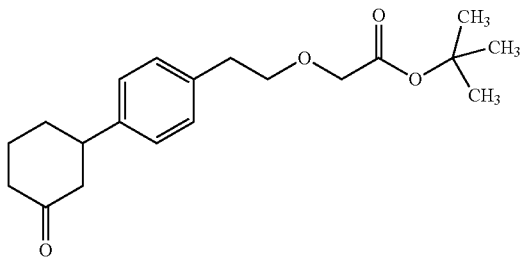 [SMILES: CC(C)(C)OC(=O)COCCc1ccc(C2CCCC(=O)C2)cc1]

A mixture of tert-butyl 2-(4-(5,5-dimethyl-1,3,2-dioxaborinan-2-yl) phenethoxy)acetate 4B (2.5 g, 7.18 mmol), cyclohex-2-enone (0.828 g, 8.61 mmol), Na$_2$CO$_3$ (1.522 g, 14.36 mmol) and water (8.97 ml) was flushed with Ar, after which chloro(1,5-cyclooctadiene)rhodium(I) dimer (0.354 g, 0.718 mmol) was added and the reaction vial was flushed again with Ar. The sealed reaction vial was heated at 85° C. overnight, then was cooled to rt, diluted with water (10 mL) and extracted with DCM (2×10 mL). The combined organic extracts were washed with brine, dried (Na$_2$SO$_4$) and concentrated in vacuo. The residue was chromatographed (SiO$_2$; 80 g; A=Hex, B=EtOAc; 15 min gradient from 0% B to 50% B; flow rate=12 mL/min; fractions containing product were identified by TLC using PMA stain) to afford the title compound (2.01 g, 6.05 mmol, 84% yield) as a pale yellow solid. $^1$H NMR (500 MHz, CDCl$_3$) δ 7.25-7.21 (m, 2H), 7.19-7.13 (m, 2H), 3.99 (s, 2H), 3.76 (t, J=7.2 Hz, 2H), 3.06-2.97 (m, 1H), 2.95 (t, J=7.2 Hz, 2H), 2.63-2.56 (m, 1H), 2.56-2.51 (m, 1H), 2.50-2.44 (m, 1H), 2.43-2.34 (m, 1H), 2.21-2.12 (m, 1H), 2.06 (s, 1H), 1.92-1.73 (m, 2H), 1.49 (s, 9H).

4D. tert-Butyl 2-(4-((+/−)-3-hydroxycyclohexyl)phenethoxy)acetate (Diastereomer 1; Absolute Stereochemistry is Arbitrarily Drawn)

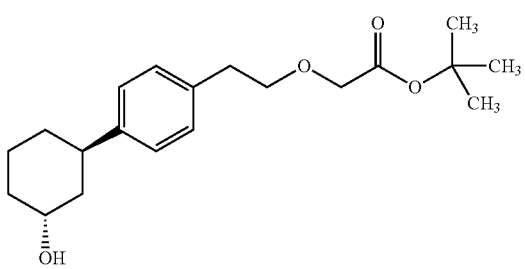 [SMILES: CC(C)(C)OC(=O)COCCc1ccc([C@@H]2CCC[C@@H](O)C2)cc1]

and

4E. tert-Butyl 2-(4-((+/−)-3-hydroxycyclohexyl)phenethoxy)acetate (Diastereomer 2; Absolute Stereochemistry is Arbitrarily Drawn)

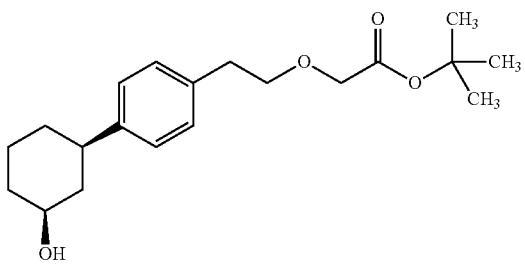 [SMILES: CC(C)(C)OC(=O)COCCc1ccc([C@@H]2CCC[C@H](O)C2)cc1]

To a mixture of tert-butyl 2-(4-(3-oxocyclohexyl) phenethoxy)acetate 4C (2.0 g, 6.02 mmol) in MeOH (60.2 ml) was added portionwise NaBH$_4$ (0.228 g, 6.02 mmol). The reaction mixture was stirred overnight under Ar at rt, then quenched was with 1 N aq HCl (100 mL) and extracted with EtOAc (2×75 mL). The combined organic extracts were washed with brine, dried (Na$_2$SO$_4$) and concentrated in vacuo. The residue was chromatographed (SiO$_2$; 80 g; A=Hex, B=EtOAc; 15 min gradient from 0% B to 50% B; flow rate=40 mL/min; product fractions identified by TLC using PMA stain) to give two compounds.

The faster eluting diastereomer 4D (0.50 g, 1.50 mmol, 24.9% yield) was obtained as a colorless oil. $^1$H NMR (400 MHz, CDCl$_3$) δ 7.24-7.15 (m, 4H), 4.32-4.20 (m, 1H), 3.99 (s, 2H), 3.76 (t, J=7.3 Hz, 2H), 3.04-2.99 (m, 1H), 2.94 (t, J=7.4 Hz, 2H), 2.01-1.77 (m, 4H), 1.74-1.55 (m, 4H), 1.50 (s, 9H), 1.40 (br. s., 1H).

The slower eluting diastereomer 4E (1.28 g, 3.83 mmol, 63.6% yield) was obtained as a colorless oil. $^1$H NMR (400 MHz, CDCl$_3$) δ 7.23-7.10 (m, 4H), 3.99 (s, 2H), 3.76 (t, J=7.3 Hz, 3H), 2.95 (t, J=7.3 Hz, 2H), 2.66-2.50 (m, 1H), 2.24-2.13 (m, 1H), 2.07 (s, 1H), 1.97-1.87 (m, 1H), 1.86-1.75 (m, 1H), 1.62 (s, 1H), 1.50 (s, 9H), 1.47-1.22 (m, 4H).

Example 4

Method A

To a 0° C. mixture of tert-butyl 2-(4-((+/−)-3-hydroxycyclohexyl)phenethoxy) acetate diastereomer 4D (150 mg, 0.448 mmol), phenol (84 mg, 0.897 mmol), Ph$_3$P (235 mg, 0.897 mmol) in THF (5 mL) was added dropwise a solution of DIAD (0.174 mL, 0.897 mmol) in THF (1 mL) over 10 min. The reaction was allowed to slowly warm to rt overnight under Ar. The solvent was concentrated and the residue was chromatographed (SiO$_2$; 12 g; A=Hex, B=EtOAc; 15 min gradient from 0% B to 40% B; flow rate=24 mL/min; TLC R$_f$=0.65; 4:1 Hex:EtOAc) to give the desired phenoxy ether. This material was dissolved in TFA (2 mL) and DCM (2 mL), then was stirred at rt for 2 h. Volatiles were removed in vacuo and the residue was purified by preparative HPLC (Gradient from 80% A:20% B to 0% A:100% B; [A=10% MeCN/90% H$_2$O+0.1% TFA); (B=90% MeCN/10% H$_2$O+0.1% TFA]; detection at 220 nm; 10 min gradient; PHENOMENEX® Axia 5μ C18, 30×100 mm) to afford the title compound (67 mg, 0.189 mmol, 42.1% yield) as a pale yellow oil. $^1$H NMR (500 MHz, DMSO-d$_6$) δ 7.27 (t, J=7.6 Hz, 2H), 7.17 (s, 4H), 6.96 (d, J=8.0 Hz, 2H), 6.90 (t, J=7.3 Hz, 1H), 4.50-4.35 (m, 1H), 4.00 (s, 2H), 3.66 (t, J=7.0 Hz, 2H), 2.80 (t, J=6.9 Hz, 2H), 2.70 (t, J=12.2 Hz, 1H), 2.15 (t, J=13.8 Hz, 2H), 1.87 (d, J=13.5 Hz, 1H), 1.77 (d, J=12.4 Hz, 1H), 1.52 (q, J=11.4 Hz, 2H), 1.44-1.28 (m, 2H).

Method B

Step 1: A mixture of tert-butyl 2-(4-((+/−)-3-hydroxycyclohexyl)phenethoxy) acetate diastereomer 4E (0.25 g, 0.75 mmol), potassium trifluoro(phenyl)borate (0.275 g, 1.50 mmol), DMAP (0.091 g, 0.75 mmol) and 4 Å molecular sieves (0.5 g) in DCM (3 mL) was stirred for 5 min, then Cu(OAc)$_2$ (0.136 g, 0.747 mmol) was added and the reaction was stirred overnight at rt under an atmosphere of 02. The reaction was then filtered, and the solids were washed repeatedly with DCM. The combined filtrates were washed with water and brine, then dried (Na$_2$SO$_4$) and concentrated in vacuo. The residue was chromatographed (SiO$_2$; 12 g; A=Hex, B=EtOAc; 15 min gradient from 0% B to 50% B; flow rate=12 mL/min) to give the desired phenyl ether. This material was dissolved in DCM (1 mL) and TFA (1 mL) and stirred at RT for 3 h (at this point LC/MS showed near complete reaction). Volatiles were removed in vacuo and the residue was purified by preparative HPLC (Gradient from 80% A:20% B to 0% A: 100% B; (A=10% MeCN/90% H$_2$O+0.1% TFA); (B=90% MeCN/10% H$_2$O+0.1% TFA); detection at 220 nm; 10 min gradient; PHENOMENEX® Axia 5μ C18, 30×100 mm) to afford the title compound (41 mg, 0.115 mmol, 15.4% yield) as a pale yellow oil. le;2q$^1$H NMR (500 MHz, CDCl$_3$) δ 8.74-7.71 (br. s., 1H), 7.34-7.24 (m, 2H), 7.19 (s, 4H), 7.01-6.87 (m, 3H), 4.43-4.27 (m, 1H), 4.14 (s, 2H), 3.80 (t, J=7.2 Hz, 2H), 2.95 (t, J=7.2 Hz, 2H), 2.74-2.58 (m, 1H), 2.37 (dt, J=12.4, 1.5 Hz, 1H), 2.28 (d, J=11.8 Hz, 1H), 2.07-1.96 (m, 1H), 1.91 (d, J=12.7 Hz, 1H), 1.73-1.34 (m, 4H).

Example 5

2-(4-((1S,3R)-3-Phenoxycyclohexyl)phenethoxy) acetic acid (cis-1,3-cyclohexyl enantiomer 1; Absolute Stereochemistry is Arbitrarily Drawn)

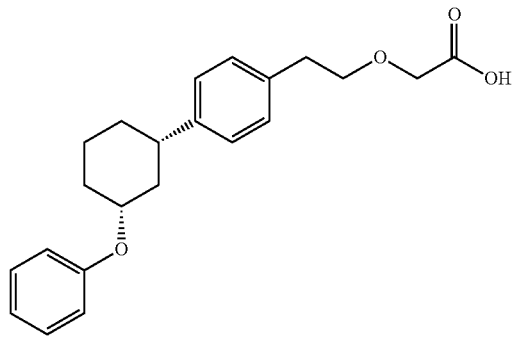 [SMILES: O=C(O)COCCc1ccc([C@H]2CCC[C@@H](Oc3ccccc3)C2)cc1]

and

Example 6

2-(4-((1R,3S)-3-Phenoxycyclohexyl)phenethoxy) acetic acid (cis-1,3-cyclohexyl enantiomer 2; Absolute Stereochemistry is Arbitrarily Drawn)

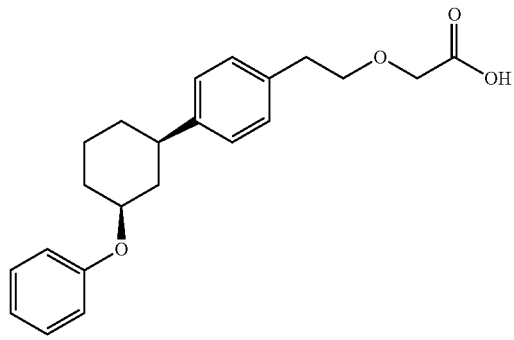 [SMILES: O=C(O)COCCc1ccc([C@@H]2CCC[C@H](Oc3ccccc3)C2)cc1]

The racemic 2-(4-((+/−)-3-phenoxycyclohexyl)phenethoxy)acetic acid Example 4 was separated by chiral preparative HPLC (Berger Multigram II SFC; Column: CHIRALPAK® OJ-H, 21×250 mm, 5 m; Mobile Phase: 20% EtOH/80% CO$_2$; Flow Conditions: 45 mL/min, 150 Bar, 40° C.; Detector Wavelength: 220 nm; Injection using 0.5 mL of 33 mg/mL in EtOH/MeOH) to afford the title compounds 5 and 6.

The faster eluting peak (Example 5; 30 mg, 0.082 mmol, 43.2% yield) was obtained as a pale yellow oil. ee=99%. $^1$H NMR (500 MHz, CDCl$_3$) δ 7.40-7.24 (m, 2H), 7.23-7.12 (m, 4H), 7.01-6.88 (m, 3H), 4.41-4.28 (m, 1H), 4.13 (s, 2H), 3.80 (t, J=7.0 Hz, 2H), 2.94 (t, J=6.9 Hz, 2H), 2.73-2.60 (m, 1H), 2.41-2.33 (m, 1H), 2.31-2.23 (m, 1H), 2.06-1.95 (m, 1H), 1.91 (d, J=12.7 Hz, 1H), 1.69-1.34 (m, 4H). [α]$_D^{20}$=+58° (c=1 in MeOH).

The slower eluting peak (Example 6; 31.4 mg, 0.087 mmol, 46.2% yield) was obtained as a pale yellow oil. ee=99%. $^1$H NMR (500 MHz, CDCl$_3$) δ 7.34-7.25 (m, 2H), 7.23-7.14 (m, 4H), 6.98-6.89 (m, 3H), 4.41-4.28 (m, 1H), 4.13 (s, 2H), 3.80 (t, J=6.9 Hz, 2H), 2.94 (t, J=6.9 Hz, 2H), 2.73-2.60 (m, 1H), 2.40-2.32 (m, 1H), 2.32-2.22 (m, 1H), 2.02-1.95 (m, 1H), 1.95-1.85 (m, 1H), 1.69-1.36 (m, 4H). $[\alpha]_D^{20}=-55°$ (c=1 in MeOH).

Example 7

(1S,2S)-2-(4-((+/−)-3-Phenoxycyclohexyl)phenethyl)cyclopropanecarboxylic acid (cis-1,3-cyclohexyl isomer; Absolute Stereochemistry of the Cyclohexyl Moiety is Arbitrarily Drawn)

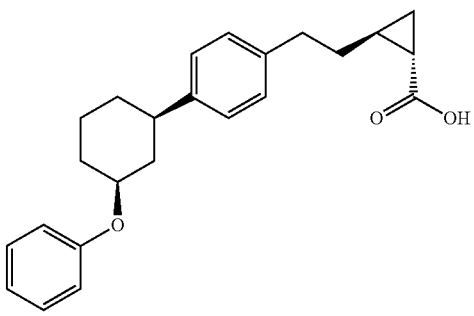 [SMILES: O=C(O)[C@H]1C[C@@H]1CCc1ccc([C@@H]2CCC[C@H](Oc3ccccc3)C2)cc1]

7A. 1-Bromo-4-(but-3-en-1-yl)benzene

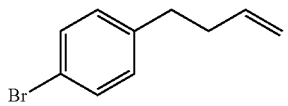

To a 0° C. solution of allylmagnesium chloride (60.0 mL of a 2 M solution in THF; 120 mmol) was dropwise added a solution of 1-bromo-4-(bromomethyl)benzene (20 g, 80 mmol) in THF (10 mL) over 30 min. The reaction was then allowed to slowly warm to rt under Ar overnight, then was carefully quenched with 10% aq. citric acid (100 mL) and extracted with EtOAc (2×50 mL). The combined organic extracts were washed with brine, dried (Na$_2$SO$_4$) and concentrated in vacuo. The residue was chromatographed (SiO$_2$; 120 g; A=Hex, B=EtOAc; 30 min gradient from 0% B to 40% B; flow rate=80 mL/min) to afford the title compound (16.21 g, 77 mmol, 96% yield) as a colorless oil.

$^1$H NMR (400 MHz, CDCl$_3$) δ 7.48-7.33 (m, 2H), 7.13-6.97 (m, 2H), 5.82 (ddt, J=17.1, 10.4, 6.5 Hz, 1H), 5.13-4.88 (m, 2H), 2.72-2.59 (m, 2H), 2.45-2.25 (m, 2H).

7B. (R)-4-(4-Bromophenyl)butane-1,2-diol

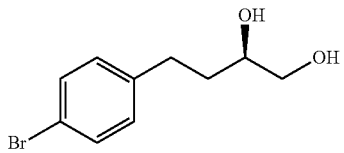 [SMILES: OC[C@H](O)CCc1ccc(Br)cc1]

To a 0° C. biphasic mixture of (DHQD)$_2$PHAL (AD-mix-beta) (55.1 g, 70.8 mmol) in t-BuOH (250 mL) and water (250 mL) was added 1-bromo-4-(but-3-en-1-yl)benzene (8.3 g, 39.3 mmol). The reaction was stirred at 0° C. overnight, then sodium sulfite (29.7 g, 236 mmol) was added; stirring at rt was continued for 1 h (after which the yellow color disappeared). The reaction was diluted with water (500 mL) and extracted with EtOAc (2×250 mL). The combined organic extracts were washed with brine, dried (Na$_2$SO$_4$) and concentrated in vacuo. The residue was chromatographed (SiO$_2$; 120 g; A=Hex, B=EtOAc; 15 min gradient from 0% B to 100% B; flow rate=40 mL/min) to afford the title compound (8.07 g, 32.9 mmol, 84% yield) as a pale yellow oil which became a white solid upon standing. $^1$H NMR (500 MHz, CDCl$_3$) δ 7.46-7.38 (m, 2H), 7.16-7.06 (m, 2H), 3.81-3.62 (m, 2H), 3.49 (ddd, J=10.9, 7.1, 4.3 Hz, 1H), 2.85-2.74 (m, 1H), 2.73-2.63 (m, 1H), 2.18 (d, J=3.9 Hz, 1H), 1.94-1.85 (m, 1H), 1.82-1.68 (m, 2H).

7C. (R)-4-(4-Bromophenyl)-2-hydroxybutyl 4-methylbenzenesulfonate

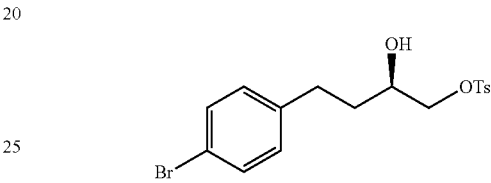

To a 0° C. mixture of (R)-4-(4-bromophenyl)butane-1,2-diol (8.07 g, 32.9 mmol) and pyridine (32.9 mL) was added portionwise p-toluenesulfonyl chloride (6.90 g, 36.2 mmol) and the reaction was stirred at 0° C. overnight. Water (100 mL) was added and the mixture was extracted with Et$_2$O (2×75 mL). The combined organic extracts were washed with 1 N aq. HCl (100 mL) and brine, then dried (Na$_2$SO$_4$) and concentrated in vacuo. The residue was chromatographed (SiO$_2$; 120 g; A=Hex, B=EtOAc; 30 min gradient from 0% B to 100% B; flow rate=80 mL/min) to afford the title compound (14.5 g, 26.1 mmol, 79% yield) as a pale yellow oil. $^1$H NMR (400 MHz, CDCl$_3$) δ 7.80 (d, J=8.1 Hz, 2H), 7.73 (dd, J=11.7, 8.4 Hz, 1H), 7.41-7.35 (m, 3H), 7.05 (d, J=8.4 Hz, 2H), 4.15 (q, J=7.2 Hz, 1H), 4.09-4.00 (m, 1H), 3.97-3.89 (m, 1H), 3.84 (dd, J=7.0, 3.3 Hz, 1H), 2.81-2.71 (m, 1H), 2.64 (dt, J=14.0, 8.1 Hz, 1H), 2.49-2.47 (m, 3H), 1.80-1.69 (m, 2H).

7D. (R)-2-(4-Bromophenethyl)oxirane

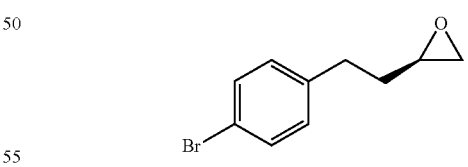

To aq. KOH (75 mL of a 2N solution) was added a solution of (R)-4-(4-bromophenyl)-2-hydroxybutyl 4-methylbenzenesulfonate (14.5 g, 26.1 mmol) in Et$_2$O (150 mL) at rt and the reaction was stirred overnight at rt. The organic phase was then separated and the aqueous phase was extracted with Et$_2$O (50 mL). The combined organic phases were washed with brine, dried (Na$_2$SO$_4$) and concentrated in vacuo. The residue was chromatographed (SiO$_2$; 80 g; A=Hex, B=EtOAc; 30 min gradient from 0% B to 50% B; flow rate=60 mL/min) to yield the title compound (4.97 g, 21.9 mmol, 84% yield) as a pale yellow oil. $^1$H NMR (500

MHz, CDCl₃) δ 7.45-7.40 (m, 2H), 7.13-7.07 (m, 2H), 2.99-2.91 (m, 1H), 2.84-2.69 (m, 3H), 2.49 (dd, J=5.1, 2.6 Hz, 1H), 1.94-1.85 (m, 1H), 1.85-1.76 (m, 1H).

7E. (1S,2S)-Ethyl 2-(4-bromophenethyl)cyclopropanecarboxylate

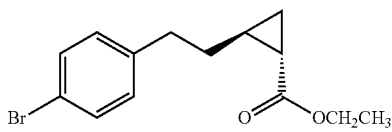

To a mixture of NaOtBu (4.21 g, 43.8 mmol) and DME (25 mL) was added dropwise ethyl 2-(diethoxyphosphoryl) acetate (9.99 mL, 50.3 mmol) over 15 min while maintaining the reaction temperature between 20-30° C. To the resulting homogenous, pale yellow solution was added a solution of (R)-2-(4-bromophenethyl)oxirane (4.97 g, 21.9 mmol) in DME (10 mL) in one portion and the reaction was heated at 60° C. overnight under Ar, then at 70° C. for a further 5 h. The reaction was cooled to rt, diluted with EtOAc (150 mL) and washed with sat. aq. NH₄Cl and brine, then dried (Na₂SO₄) and concentrated in vacuo. The residue was chromatographed (SiO₂; 120 g; A=Hex, B=EtOAc; 30 min gradient from 0% B to 50% B flow rate=80 mL/min; TLC R$_f$=0.65 (4:1 Hex:EtOAc)) to yield the title compound (5.29 g, 17.8 mmol, 81% yield) as a pale yellow oil. ¹H NMR (500 MHz, CDCl₃) δ 7.43-7.38 (m, 2H), 7.09-7.03 (m, 2H), 4.13 (q, J=7.2 Hz, 2H), 2.69 (t, J=7.6 Hz, 2H), 1.67-1.56 (m, 2H), 1.42-1.32 (m, 2H), 1.31-1.25 (m, 3H), 1.17 (dt, J=8.7, 4.5 Hz, 1H), 0.69 (ddd, J=8.1, 6.3, 4.3 Hz, 1H). [α]$_D^{20}$=+44.8° (c=1 in MeOH).

7F. (1S,2S)-Ethyl 2-(4-(5,5-dimethyl-1,3,2-dioxaborinan-2-yl)phenethyl)-cyclopropanecarboxylate

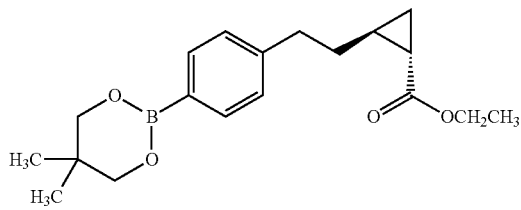 [SMILES: CCOC(=O)[C@H]1C[C@@H]1CCc1ccc(B2OCC(C)(C)CO2)cc1]

The title compound was prepared from (1S,2S)-ethyl 2-(4-bromophenethyl) cyclopropanecarboxylate using the same procedure as used for the synthesis of Compound 4B from Compound 4A. The title compound (4.72 g, 14.29 mmol, 94% yield) was obtained as a pale yellow oil. ¹H NMR (500 MHz, CDCl₃) δ 7.64 (d, J=8.0 Hz, 2H), 7.09 (d, J=8.0 Hz, 2H), 4.03 (q, J=7.2 Hz, 2H), 3.69 (s, 4H), 2.65 (t, J=7.6 Hz, 2H), 1.58-1.51 (m, 2H), 1.35-1.24 (m, 2H), 1.21-1.15 (m, 3H), 1.10-1.04 (m, 1H), 0.97-0.93 (m, 7H).

7G. (1S,2S)-Ethyl 2-(4-(3-oxocyclohexyl)phenethyl) cyclopropanecarboxylate

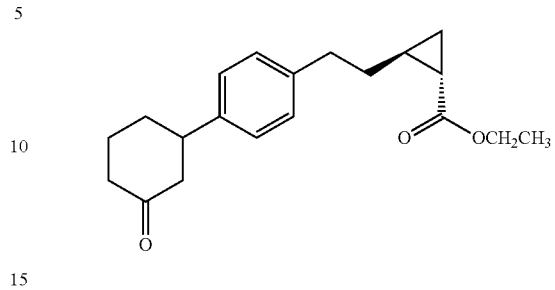

The title compound was synthesized from (1S,2S)-ethyl 2-(4-(5,5-dimethyl-1,3,2-dioxaborinan-2-yl)phenethyl)-cyclopropanecarboxylate using the same procedure as used for the preparation of Compound 4C from Compound 4B. The title compound (0.67 g, 2.13 mmol, 70.4% yield) was obtained as a tan solid. ¹H NMR (500 MHz, CDCl₃) δ 7.15 (s, 4H), 4.19-4.07 (m, 2H), 3.06-2.95 (m, 1H), 2.72 (t, J=7.7 Hz, 2H), 2.63-2.58 (m, 1H), 2.54 (dd, J=12.5, 1.0 Hz, 1H), 2.51-2.45 (m, 1H), 2.44-2.35 (m, 1H), 2.16 (ddd, J=9.7, 6.4, 3.2 Hz, 1H), 2.12-2.05 (m, 1H), 1.91-1.74 (m, 2H), 1.69-1.57 (m, 2H), 1.44-1.36 (m, 2H), 1.28 (t, J=7.2 Hz, 3H), 1.18 (dt, J=8.7, 4.5 Hz, 1H), 0.72 (ddd, J=8.0, 6.4, 4.3 Hz, 1H).

7H. (1S,2S)-Ethyl 2-(4-((+/−)-3-hydroxycyclohexyl) phenethyl)cyclopropanecarboxylate (trans-1,3-cyclohexyl diastereomer 1; Absolute Stereochemistry of the Cyclohexyl Moiety is Arbitrarily Drawn)

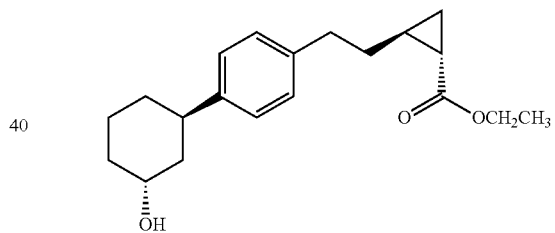

and

7I. (1S,2S)-Ethyl 2-(4-((+/−)-3-hydroxycyclohexyl) phenethyl)cyclopropane-carboxylate (cis-1,3-cyclohexyl diastereomer 2; Absolute Stereochemistry of the Cyclohexyl Moiety is Arbitrarily Drawn)

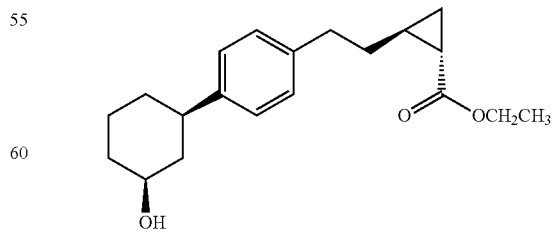

To a solution of (1S,2S)-ethyl 2-(4-(3-oxocyclohexyl) phenethyl)cyclopropane carboxylate (0.67 g, 2.13 mmol) in MeOH (42.6 ml) was added NaBH₄ (0.081 g, 2.13 mmol)

portionwise. The reaction was stirred under Ar overnight at rt, then was quenched with 1 N aq. HCl (100 mL) and extracted with EtOAc (2×50 mL). The combined organic extracts were washed with brine, dried (Na$_2$SO$_4$) and concentrated in vacuo. The residue was chromatographed (SiO$_2$; 40 g; A=Hex, B=EtOAc; 15 min gradient from 0% B to 50% B; flow rate=40 mL/min; fractions containing product were identified by TLC using PMA stain) to afford two products.

The faster eluting diastereomer 7H (0.13 g, 0.411 mmol, 19.3% yield) was obtained as a colorless oil. 1H NMR (500 MHz, CDCl$_3$) δ 7.08-6.98 (m, 4H), 4.10-4.00 (m, 2H), 3.65 (tt, J=10.9, 4.3 Hz, 1H), 2.61 (t, J=7.7 Hz, 2H), 2.48 (tt, J=12.3, 3.3 Hz, 1H), 2.11-2.05 (m, 1H), 2.01-1.95 (m, 1H), 1.84-1.79 (m, 1H), 1.77-1.71 (m, 1H), 1.59-1.47 (m, 3H), 1.39-1.27 (m, 4H), 1.26-1.21 (m, 1H), 1.20-1.16 (m, 4H), 1.09 (dt, J=8.7, 4.5 Hz, 1H).

The slower eluting diastereomer 7I (0.45 g, 1.422 mmol, 66.7% yield) was obtained as a colorless oil. $^1$H NMR (500 MHz, CDCl$_3$) δ 7.17-7.09 (m, 4H), 4.27-4.23 (m, 1H), 4.19-4.07 (m, 2H), 3.00 (tt, J=12.2, 3.3 Hz, 1H), 2.71 (t, J=7.7 Hz, 2H), 2.01-1.94 (m, 1H), 1.93-1.88 (m, 1H), 1.87-1.80 (m, 2H), 1.74-1.54 (m, 5H), 1.49-1.36 (m, 3H), 1.32-1.24 (m, 3H), 1.18 (dt, J=8.8, 4.4 Hz, 1H), 0.72 (ddd, J=8.3, 6.3, 4.1 Hz, 1H).

Example 7

To a 0° C. mixture of (1S,2S)-ethyl 2-(4-((+/−)-3-hydroxycyclohexyl) phenethyl)cyclopropanecarboxylate (trans-1,3-cyclohexyl diastereomer; 120 mg, 0.379 mmol), phenol (71.4 mg, 0.758 mmol), Ph$_3$P (199 mg, 0.758 mmol) in THF (5 mL) was added dropwise a solution of DIAD (0.147 mL, 0.758 mmol) in THF (1 mL) over 10 min. The reaction was allowed to slowly warm to rt overnight under Ar, then was concentrated in vacuo and the residue was chromatographed (SiO$_2$; 12 g; A=Hex, B=EtOAc; 15 min gradient from 0% B to 40% B; flow rate=24 mL/min; TLC R$_f$=0.65; 4:1 Hex:EtOAc) to give the desired phenyl ether product. A mixture of this material in KOH (2 N in MeOH; 1 mL) and water (1 mL) was stirred at rt overnight, then was partitioned into 1 N aq. HCl (10 mL) and extracted with EtOAc (2×5 mL). The combined organic extracts were washed with brine, dried (Na$_2$SO$_4$) and concentrated in vacuo. The residue was purified by preparative HPLC (Column: Waters XBridge C18, 19×200 mm, 5-μm particles; Mobile Phase A: 5:95 MeCN:water with 10 mM NH$_4$OAc; Mobile Phase B: 95:5 MeCN: water with 10 mM NH$_4$OAc; Continuous gradient from 35-70% B over 20 min, then a 5-min hold at 100% B; Flow rate: 20 mL/min) to yield the title compound (45.6 mg, 0.118 mmol, 31% yield) as a pale yellow oil. 1H NMR (500 MHz, DMSO-d$_6$) δ 7.30-7.23 (m, 2H), 7.18-7.14 (m, 2H), 7.13-7.09 (m, 2H), 6.98-6.93 (m, 2H), 6.89 (t, J=7.3 Hz, 1H), 4.41 (s, 1H), 2.69 (br. s., 1H), 2.64-2.57 (m, 2H), 2.14 (br. s., 2H), 1.91-1.81 (m, 1H), 1.80-1.72 (m, 1H), 1.58-1.47 (m, 4H), 1.41-1.29 (m, 3H), 1.25-1.14 (m, 1H), 0.97-0.90 (m, 1H), 0.71 (dt, J=3.9, 2.0 Hz, 1H).

Example 8

(1S,2S)-2-(4-((1S,3S)-3-Phenoxycyclohexyl)phenethyl)cyclopropanecarboxylic acid (trans-1,3-cyclohexyl enantiomer 1; Absolute Stereochemistry of the Cyclohexyl Moiety is Arbitrarily Drawn)

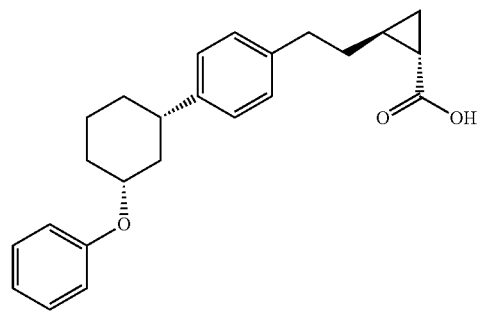 [SMILES: O=C(O)[C@H]1C[C@@H]1CCc1ccc([C@H]2CCC[C@@H](Oc3ccccc3)C2)cc1]

and

Example 9

(1S,2S)-2-(4-((1R,3R)-3-Phenoxycyclohexyl)phenethyl)cyclopropanecarboxylic acid (trans-1,3-cyclohexyl enantiomer 2; Absolute Stereochemistry of the Cyclohexyl Moiety is Arbitrarily Drawn)

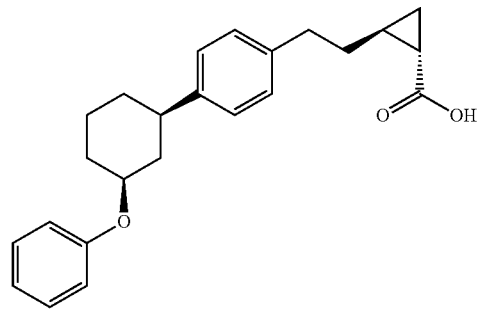 [SMILES: O=C(O)[C@H]1C[C@@H]1CCc1ccc([C@@H]2CCC[C@H](Oc3ccccc3)C2)cc1]

The racemic mixture Example 7 was separated by chiral preparative HPLC (Instrument=PIC Solution 200 SFC; Column: CHIRALPAK® OJ-H, 21×250 mm, 5 μm; Mobile Phase: 25% EtOH/75% CO$_2$; Flow Conditions: 45 mL/min, 150 Bar, 40° C.; Detector Wavelength: 220 nm; Injection Details: 0.5 mL of 9 mg/mL in EtOH) to afford the title compounds:

The faster eluting enantiomer Example 8 (11 mg, 0.030 mmol, 29.1% yield) was obtained as a pale yellow oil. ee>99%. $^1$H NMR (500 MHz, CDCl$_3$) δ 7.21-7.15 (m, 2H), 7.08-6.99 (m, 4H), 6.87-6.81 (m, 3H), 4.27-4.20 (m, 1H), 2.67-2.50 (m, 3H), 2.30-2.23 (m, 1H), 2.17 (d, J=11.8 Hz, 1H), 1.92-1.85 (m, 1H), 1.84-1.75 (m, 1H), 1.59-1.49 (m, 3H), 1.46-1.27 (m, 5H), 1.15 (br. s., 1H), 0.70 (br. s., 1H).

The slower eluting enantiomer Example 9 (12 mg, 0.032 mmol, 31.8% yield) was obtained as a pale yellow oil. ee>99%. $^1$H NMR (500 MHz, CDCl$_3$) δ 7.26-7.13 (m, 2H), 7.10-6.94 (m, 4H), 6.89-6.78 (m, 3H), 4.30-4.18 (m, 1H), 2.67-2.49 (m, 3H), 2.31-2.23 (m, 1H), 2.17 (d, J=11.8 Hz, 1H), 1.94-1.85 (m, 1H), 1.80 (d, J=12.7 Hz, 1H), 1.59-1.49 (m, 3H), 1.46-1.27 (m, 5H), 1.16 (d, J=12.4 Hz, 1H), 0.70 (br. s., 1H).

Example 10

(1R,2R)-2-(4-((+/−)-3-Phenoxycyclohexyl)phenethyl)cyclopropanecarboxylic acid (cis-1,3-cyclohexyl isomer; Absolute Stereochemistry of the Cyclohexyl Moiety is Arbitrarily Drawn)

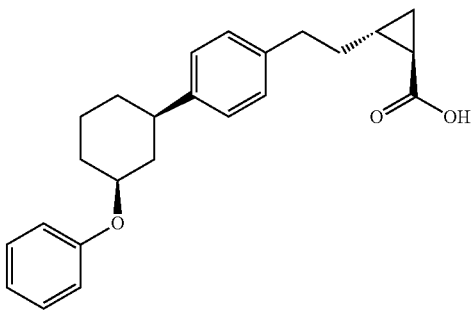 [SMILES: O=C(O)[C@@H]1C[C@H]1CCc1ccc([C@@H]2CCC[C@H](Oc3ccccc3)C2)cc1]

10A. (S)-4-(4-Bromophenyl)butane-1,2-diol

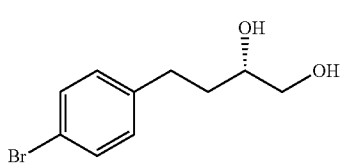 [SMILES: OC[C@@H](O)CCc1ccc(Br)cc1]

The title compound was prepared from 1-bromo-4-(but-3-en-1-yl)benzene using the same procedure as for the generation of Compound 7B from Compound 7A, except that (DHQ)₂PHAL (AD-mix-alpha) was used instead of (DHQD)₂PHAL (AD-mix-beta). The title compound (7.58 g, 30.9 mmol, 82% yield) was obtained as an off-white solid. ¹H NMR (400 MHz, CDCl₃) δ 7.46-7.34 (m, 2H), 7.14-7.03 (m, 2H), 3.78-3.60 (m, 2H), 3.56-3.40 (m, 1H), 2.83-2.72 (m, 1H), 2.71-2.61 (m, 1H), 2.11 (d, J=4.4 Hz, 1H), 1.83-1.68 (m, 3H).

10B. (S)-4-(4-Bromophenyl)-2-hydroxybutyl 4-methylbenzenesulfonate

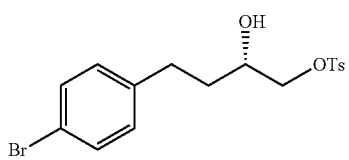 [SMILES: Cc1ccc(S(=O)(=O)OC[C@@H](O)CCc2ccc(Br)cc2)cc1]

The title compound was prepared from (S)-4-(4-bromophenyl)butane-1,2-diol by an analogous procedure used for the synthesis of Compound 7C from Compound 7B. The title compound (7.46 g, 18.76 mmol, 60.7% yield) was obtained as a pale yellow oil. ¹H NMR (500 MHz, CDCl₃) δ 7.82-7.76 (m, 2H), 7.41-7.31 (m, 4H), 7.05-6.99 (m, 2H), 4.01 (dd, J=10.2, 3.0 Hz, 1H), 3.93-3.88 (m, 1H), 3.85-3.77 (m, 1H), 2.78-2.69 (m, 1H), 2.66-2.58 (m, 1H), 2.48-2.44 (m, 3H), 2.13 (dd, J=5.0, 0.6 Hz, 1H), 1.77-1.62 (m, 2H).

10C. (S)-2-(4-Bromophenethyl)oxirane

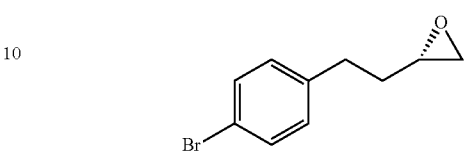

The title compound was prepared from (S)-4-(4-bromophenyl)-2-hydroxybutyl 4-methylbenzenesulfonate by a procedure analogous to that used for the synthesis of Compound 7D from Compound 7C. The title compound (3.87 g, 17.04 mmol, 91% yield) was obtained as a pale yellow oil. ¹H NMR (500 MHz, CDCl₃) δ 7.46-7.36 (m, 2H), 7.13-7.04 (m, 2H), 2.98-2.88 (m, 1H), 2.84-2.66 (m, 3H), 2.47 (dd, J=5.0, 2.8 Hz, 1H), 1.92-1.83 (m, 1H), 1.82-1.74 (m, 1H).

10D. (1R,2R)-Ethyl 2-(4-bromophenethyl)cyclopropanecarboxylate

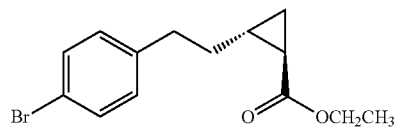 [SMILES: CCOC(=O)[C@@H]1C[C@H]1CCc1ccc(Br)cc1]

The title compound was prepared from (S)-2-(4-bromophenethyl)oxirane by a procedure analogous to that used for the synthesis of Compound 7E from Compound 7D. The title compound (1.98 g, 6.66 mmol, 40.3% yield) was obtained as a pale yellow oil. ¹H NMR (500 MHz, CDCl₃) δ 7.44-7.34 (m, 2H), 7.10-6.99 (m, 2H), 4.10 (q, J=7.2 Hz, 2H), 2.67 (t, J=7.6 Hz, 2H), 1.63-1.55 (m, 2H), 1.39-1.30 (m, 2H), 1.28-1.23 (m, 3H), 1.18-1.11 (m, 1H), 0.67 (ddd, J=8.1, 6.5, 4.4 Hz, 1H). [α]_D^{20}=−37.7° (c=1 in MeOH).

10E. (1R,2R)-Ethyl 2-(4-(5,5-dimethyl-1,3,2-dioxaborinan-2-yl)phenethyl)-cyclopropanecarboxylate

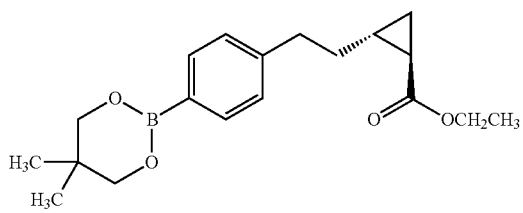 [SMILES: CCOC(=O)[C@@H]1C[C@H]1CCc1ccc(B2OCC(C)(C)CO2)cc1]

The title compound was prepared from (1R,2R)-ethyl 2-(4-bromophenethyl)cyclopropane carboxylate by a procedure analogous to that used for the synthesis of Compound 4B from Compound 4A. The title compound (1.91 g, 5.78 mmol, 96% yield) was obtained as a pale yellow oil. ¹H NMR (500 MHz, CDCl₃) δ 7.78-7.68 (m, 2H), 7.18 (d, J=8.0 Hz, 2H), 4.13 (q, J=7.2 Hz, 2H), 3.83-3.72 (m, 4H), 2.75 (t, J=7.7 Hz, 2H), 1.69-1.57 (m, 2H), 1.37 (dd, J=8.1, 4.5 Hz, 2H), 1.31-1.24 (m, 3H), 1.21-1.14 (m, 1H), 1.09-1.00 (m, 6H), 0.70 (td, J=4.1, 2.2 Hz, 1H).

10F. (1R,2R)-Ethyl 2-(4-(3-oxocyclohexyl)phenethyl)cyclopropanecarboxylate

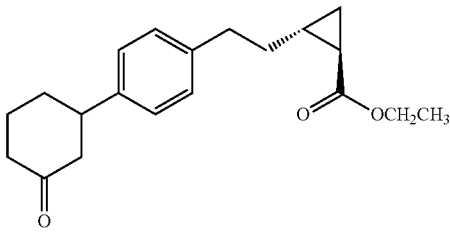 [SMILES: CCOC(=O)[C@@H]1C[C@H]1CCc1ccc(C2CCCC(=O)C2)cc1]

The title compound was prepared from (1R,2R)-ethyl 2-(4-(5,5-dimethyl-1,3,2-dioxaborinan-2-yl)phenethyl)-cyclopropanecarboxylate and cyclohexenone by a procedure analogous to that used for the synthesis of Compound 4C from Compound 4B. The title compound (0.86 g, 2.74 mmol, 90% yield) was obtained as a pale yellow oil. $^1$H NMR (500 MHz, CDCl$_3$) δ 7.21-7.07 (m, 4H), 4.14 (qd, J=7.2, 1.7 Hz, 2H), 3.00 (s, 1H), 2.72 (t, J=7.7 Hz, 2H), 2.59 (dt, J=4.3, 2.0 Hz, 1H), 2.56-2.45 (m, 2H), 2.43-2.34 (m, 1H), 2.17 (td, J=6.4, 3.2 Hz, 1H), 2.12-2.05 (m, 1H), 1.89-1.74 (m, 2H), 1.67-1.58 (m, 2H), 1.44-1.36 (m, 2H), 1.28 (t, J=7.0 Hz, 3H), 1.18 (dt, J=8.8, 4.4 Hz, 1H), 0.72 (ddd, J=8.3, 6.3, 4.1 Hz, 1H).

10G. (1R,2R)-Ethyl 2-(4-((+/−)-3-hydroxycyclohexyl)phenethyl) cyclopropanecarboxylate (Diastereomer 1; Absolute Stereochemistry of the Cyclohexyl Moiety is Arbitrarily Drawn)

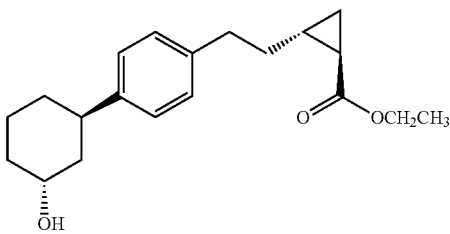 [SMILES: CCOC(=O)[C@@H]1C[C@H]1CCc1ccc([C@@H]2CCC[C@@H](O)C2)cc1]

and 10H. (1R,2R)-Ethyl 2-(4-((+/−)-3-hydroxycyclohexyl)phenethyl)-cyclopropanecarboxylate (Diastereomer 2; Absolute Stereochemistry of the Cyclohexyl Moiety is Arbitrarily Drawn)

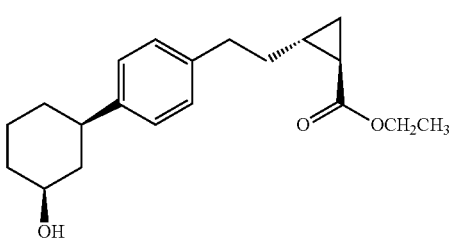 [SMILES: CCOC(=O)[C@@H]1C[C@H]1CCc1ccc([C@@H]2CCC[C@H](O)C2)cc1]

Compounds 10G and 10H were prepared from (1R,2R)-ethyl 2-(4-(3-oxocyclohexyl)phenethyl)cyclopropanecarboxylate 10F by the same procedure as used for the synthesis of Compounds 7H and 7I from 7G. The title compounds were obtained as a mixture of diastereomers.

The faster eluting diastereomer 10G (174 mg, 0.550 mmol, 20.1% yield) was obtained as a pale yellow oil. $^1$H NMR (400 MHz, CDCl$_3$) δ 7.04 (q, J=8.1 Hz, 4H), 4.20-4.13 (m, 1H), 4.10-3.98 (m, 2H), 2.90 (tt, J=12.2, 3.4 Hz, 1H), 2.61 (t, J=7.7 Hz, 2H), 1.92-1.68 (m, 4H), 1.65-1.44 (m, 6H), 1.42-1.25 (m, 3H), 1.22-1.15 (m, 3H), 1.08 (dt, J=8.7, 4.5 Hz, 1H), 0.62 (ddd, J=8.1, 6.3, 4.1 Hz, 1H).

The slower eluting diastereomer 10H (520 mg, 1.64 mmol, 60.1% yield) was obtained as a pale yellow oil. $^1$H NMR (400 MHz, CDCl$_3$) δ 7.18-7.08 (m, 4H), 4.20-4.09 (m, 2H), 3.75 (tt, J=10.8, 4.2 Hz, 1H), 2.71 (t, J=7.7 Hz, 2H), 2.58 (tt, J=12.2, 3.3 Hz, 1H), 2.22-2.15 (m, 1H), 2.13-2.04 (m, 1H), 1.96-1.88 (m, 1H), 1.88-1.80 (m, 1H), 1.71-1.55 (m, 4H), 1.51-1.37 (m, 4H), 1.35-1.24 (m, 4H), 1.18 (dt, J=8.6, 4.4 Hz, 1H), 0.72 (ddd, J=8.1, 6.4, 4.2 Hz, 1H).

Example 10

To a 0° C. mixture of diastereomer 10G (0.174 g, 0.55 mmol), phenol (0.103 g, 1.10 mmol), Ph$_3$P (0.288 g, 1.10 mmol) and THF (7 mL) was added dropwise a solution of DIAD (0.214 mL, 1.10 mmol) in THF (2 mL) over 10 min. The reaction was allowed to slowly to warm to RT overnight under Ar. Volatiles were removed in vacuo and the residue was chromatographed (SiO$_2$; 12 g; A=Hex, B=EtOAc; 15 min gradient from 0% B to 40% B; flow rate=24 mL/min; TLC R$_f$=0.65; 4:1 Hex:EtOAc) to give the desired phenyl ether ester. A solution of this product in KOH (2 N in MeOH) (5 mL), THF (1 mL) and water (1 drop) was stirred overnight at RT, then was partitioned into 1 N aq. HCl (10 mL) and extracted with EtOAc (2×5 mL). The combined organic extracts were washed with brine, dried (Na$_2$SO$_4$) and concentrated in vacuo. The residue was purified by preparative HPLC (Column: Waters XBridge C18, 19×200 mm, 5-μm particles; Mobile Phase A: 5:95 MeCN: water with 10 mM NH$_4$OAc; Mobile Phase B: 95:5 MeCN: water with 10-mM NH$_4$OAc; Gradient: 35-70% B over 20 min, then a 5-min hold at 100% B; Flow rate: 20 mL/min) to give the title compound (40.4 mg, 0.110 mmol, 20.0% yield) as a pale yellow oil. $^1$H NMR (500 MHz, DMSO-d$_6$) δ 7.26 (dd, J=8.7, 7.3 Hz, 2H), 7.17-7.14 (m, 2H), 7.13-7.08 (m, 2H), 6.95 (dd, J=8.7, 1.0 Hz, 2H), 6.89 (s, 1H), 4.45-4.37 (m, 1H), 2.72-2.65 (m, 1H), 2.61 (s, 2H), 2.20-2.09 (m, 2H), 1.89-1.83 (m, 1H), 1.79-1.72 (m, 1H), 1.58-1.45 (m, 4H), 1.40-1.28 (m, 3H), 1.23-1.13 (m, 1H), 0.97-0.89 (m, 1H), 0.74-0.67 (m, 1H).

Example 11

(1S,2S)-2-((4-((+/−)-3-Phenoxycyclohexyl)phenoxy)methyl)cyclopropanecarboxylic acid (Absolute Stereochemistry of the Cyclohexyl Moiety is Arbitrarily Drawn)

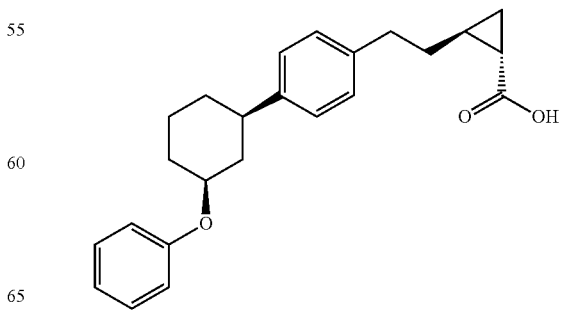

11A. (R)-2-((4-Bromophenoxy)methyl)oxirane

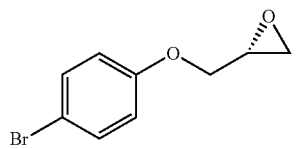

To a 0° C. biphasic solution of (S)-2-(chloromethyl) oxirane (12.03 g, 130 mmol), N,N,N-trimethyl-1-phenyl-methanaminium chloride (1.610 g, 8.67 mmol), toluene (30 mL) and water (30 mL) were successively added 4-bromophenol (15 g, 87 mmol) and 6 N aq. NaOH (18.8 mL, 113 mmol; dropwise) over 30 min. The reaction was then allowed to slowly reach rt overnight, then was diluted with EtOAc (150 mL), and washed with 1 N aq. KOH (3×75 mL). The organic phase was washed with brine, dried ($Na_2SO_4$) and concentrated in vacuo. The residue was chromatographed ($SiO_2$; 120 g; A=Hex, B=EtOAc; 30 min gradient from 0% B to 20% B; flow rate=80 mL/min) to afford the title compound (12.68 g, 55.4 mmol, 63.8% yield) as a colorless oil. $^1$H NMR (400 MHz, $CDCl_3$) δ 7.43-7.32 (m, 2H), 6.86-6.76 (m, 2H), 4.20 (dd, J=11.0, 3.1 Hz, 1H), 3.90 (dd, J=11.0, 5.7 Hz, 1H), 3.40-3.29 (m, 1H), 2.90 (dd, J=4.8, 4.2 Hz, 1H), 2.74 (dd, J=4.8, 2.6 Hz, 1H). $[α]_D^{20}$=−9.2° (c=1 in MeOH).

11B. (1S,2S)-Ethyl 2-((4-bromophenoxy)methyl)cyclopropanecarboxylate

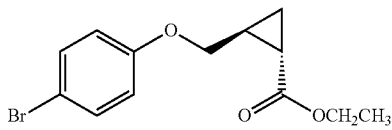 [SMILES: CCOC(=O)[C@H]1C[C@@H]1COc1ccc(Br)cc1]

To a 0° C. suspension of NaH (3.93 g, 98 mmol, 60% dispersion in mineral oil) and toluene (80 mL) was added freshly distilled ethyl 2-(diethoxyphosphoryl)acetate (26.2 mL, 131 mmol) over 50 min. After stirring for another 10 min, a solution of (R)-2-((4-bromo-phenoxy)methyl)oxirane (7.5 g, 32.7 mmol; dried by azeotroping with toluene) in toluene (20 mL) was added dropwise over 20 min. The reaction was heated to 80° C. under Ar for 18 h, then at reflux for 5 h, then cooled to rt and dissolved in EtOAc (150 mL). The organic phase was washed with sat. aq. $NH_4Cl$ and brine, dried ($Na_2SO_4$) and concentrated in vacuo. The residue was chromatographed ($SiO_2$; 120 g cartridge; A=Hex, B=EtOAc; 30 min gradient from 0% B to 100% B flow rate=80 mL/min) to afford the title compound (3.14 g, 10.50 mmol, 32.1% yield) as a colorless oil. $^1$H NMR (400 MHz, $CDCl_3$) δ 7.40-7.31 (m, 2H), 6.84-6.65 (m, 2H), 4.20-4.08 (m, 2H), 3.91 (dd, J=10.1, 5.9 Hz, 1H), 3.83 (dd, J=10.1, 6.6 Hz, 1H), 1.95-1.81 (m, 1H), 1.76-1.62 (m, 1H), 1.34-1.23 (m, 4H), 0.98 (ddd, J=8.5, 6.2, 4.4 Hz, 1H). $[α]_D^{20}$=−63° (c=1 in MeOH).

11C. (1S,2S)-Ethyl 2-((4-(4,4,5,5-tetramethyl-1,3,2-dioxaborolan-2-yl)phenoxy)methyl) cyclopropanecarboxylate

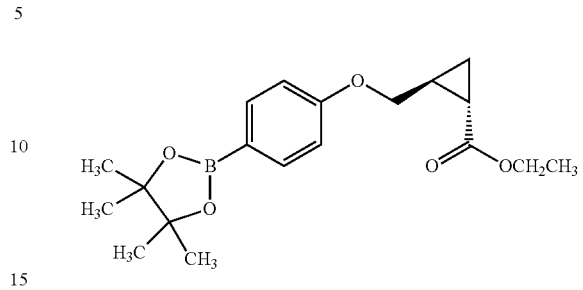

The title was prepared from (1S,2S)-ethyl 2-((4-bromophenoxy)methyl)cyclo-propanecarboxylate by the same procedure as used for the synthesis of Compound 1C from Compound 1B. The title compound was obtained (0.97 g, 2.80 mmol, 84% yield) as a pale yellow oil. $^1$H NMR (400 MHz, $CDCl_3$) δ 7.80-7.66 (m, 2H), 6.92-6.77 (m, 2H), 4.14 (dd, J=7.3, 0.7 Hz, 2H), 3.96 (d, J=5.9 Hz, 1H), 3.91 (d, J=6.4 Hz, 1H), 1.94-1.84 (m, 1H), 1.75-1.66 (m, 1H), 1.36-1.31 (m, 12H), 1.31-1.27 (m, 4H), 1.03-0.96 (m, 1H).

11D. (4-(((1S,2S)-2-(Ethoxycarbonyl)cyclopropyl)methoxy)phenyl)boronic acid

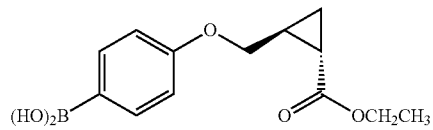 [SMILES: CCOC(=O)[C@H]1C[C@@H]1COc1ccc(B(O)O)cc1]

The title compound was prepared from (1S,2S)-ethyl 2-((4-(4,4,5,5-tetramethyl-1,3,2-dioxaborolan-2-yl)phenoxy) methyl) cyclopropanecarboxylate by an analogous procedure to that used for the synthesis of Compound 1D from Compound 1C. The title compound (0.54 g, 2.045 mmol, 80% yield) was obtained as a pale yellow oil. $^1$H NMR (500 MHz, $CD_3CN$) δ 8.23-8.12 (m, 2H), 7.09-7.01 (m, 2H), 4.18-4.10 (m, 3H), 3.93 (dd, J=10.2, 7.4 Hz, 1H), 1.91-1.81 (m, 1H), 1.77-1.71 (m, 1H), 1.30-1.23 (m, 4H), 1.09-1.01 (m, 1H).

11E. (1S,2S)-Ethyl 2-((4-(3-oxocyclohexyl)phenoxy)methyl)cyclopropanecarboxylate

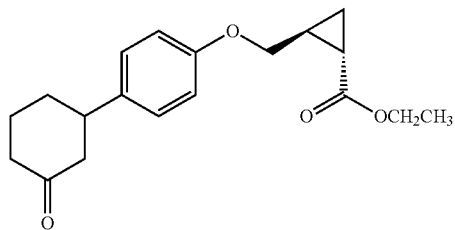 [SMILES: CCOC(=O)[C@H]1C[C@@H]1COc1ccc(C2CCCC(=O)C2)cc1]

The title compound was prepared from (4-(((1S,2S)-2 (ethoxycarbonyl) cyclopropyl)methoxy)phenyl)boronic acid by an analogous procedure to that used for the synthesis of Compound 1E from Compound 1D. The title compound (0.57 g, 1.80 mmol, 88% yield) was obtained as a pale yellow oil. $^1$H NMR (500 MHz, CDCl$_3$) δ 7.19-7.06 (m, 2H), 6.93-6.74 (m, 2H), 4.21-4.09 (m, 2H), 3.96-3.90 (m, 1H), 3.89-3.83 (m, 1H), 2.95 (ddt, J=11.6, 7.8, 4.0 Hz, 1H), 2.60-2.54 (m, 1H), 2.52-2.42 (m, 2H), 2.41-2.31 (m, 1H), 2.13 (ddt, J=9.7, 6.4, 3.3 Hz, 1H), 2.08-2.01 (m, 1H), 1.92-1.85 (m, 1H), 1.85-1.73 (m, 2H), 1.72-1.65 (m, 1H), 1.32-1.24 (m, 4H), 0.98 (ddd, J=8.5, 6.3, 4.4 Hz, 1H).

11F. (1S,2S)-Ethyl 2-((4-((+/−)-3-hydroxycyclohexyl)phenoxy)methyl) cyclopropanecarboxylate

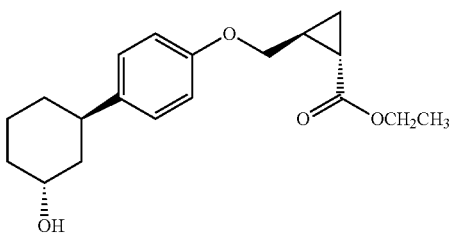 [SMILES: CCOC(=O)[C@H]1C[C@@H]1COc1ccc([C@@H]2CCC[C@@H](O)C2)cc1]

and 11G. (1S,2S)-Ethyl 2-((4-((+/−)-3-hydroxycyclohexyl)phenoxy)methyl) cyclopropanecarboxylate

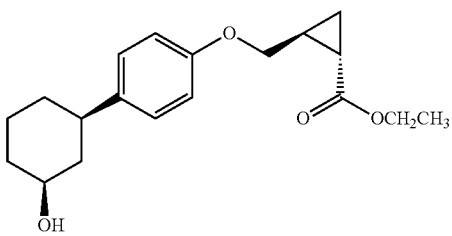 [SMILES: CCOC(=O)[C@H]1C[C@@H]1COc1ccc([C@@H]2CCC[C@H](O)C2)cc1]

Compounds 11F and 11G were prepared by an analogous procedure used for the generation of Compounds 1F and 1G using 11E instead of 1E to afford the title compounds:

The faster eluting diastereomer 11F (118 mg, 0.371 mmol, 22.6% yield) was obtained as a pale yellow oil. $^1$H NMR (500 MHz, CDCl$_3$) δ 7.16-7.06 (m, 2H), 6.86-6.76 (m, 2H), 4.24-4.19 (m, 1H), 4.17-4.09 (m, 2H), 3.93-3.81 (m, 2H), 3.00-2.90 (m, 1H), 1.97-1.73 (m, 6H), 1.71-1.59 (m, 3H), 1.57-1.49 (m, 1H), 1.45-1.36 (m, 1H), 1.30-1.25 (m, 4H), 0.97 (ddd, J=8.5, 6.3, 4.5 Hz, 1H).

The slower eluting diastereomer 11G (290 mg, 0.911 mmol, 55.4% yield) was obtained as a pale yellow oil. $^1$H NMR (500 MHz, CDCl$_3$) δ 7.15-7.07 (m, 2H), 6.86-6.77 (m, 2H), 4.20-4.10 (m, 2H), 3.96-3.82 (m, 2H), 3.78-3.66 (m, 1H), 2.53 (tt, J=12.2, 3.3 Hz, 1H), 2.19-2.10 (m, 1H), 2.09-2.00 (m, 1H), 1.93-1.85 (m, 2H), 1.82-1.76 (m, 1H), 1.72-1.65 (m, 1H), 1.59 (br. s., 1H), 1.46-1.34 (m, 2H), 1.32-1.21 (m, 6H), 0.98 (ddd, J=8.5, 6.3, 4.5 Hz, 1H).

Example 11

To a 0° C. mixture of (1S,2S)-ethyl 2-((4-((+/−)-3-hydroxycyclohexyl) phenoxy)methyl)cyclopropane carboxylate diastereomer 11F (0.090 g, 0.283 mmol), phenol (0.053 g, 0.565 mmol) and Ph$_3$P (0.148 g, 0.565 mmol) in THF (2 mL) was added dropwise DIAD (0.110 mL, 0.565 mmol) over 10 min. The reaction was allowed to warm to rt overnight under Ar. Volatiles were removed in vacuo and the residue was chromatographed (SiO$_2$; 24 g; A=Hex, B=EtOAc; 15 min gradient from 0% B to 40% B; flow rate=24 mL/min; TLC R$_f$=0.65; 4:1 Hex:EtOAc) to give the desired phenyl ether product. This material was dissolved in KOH (2 N in MeOH) (2 mL) and water (1 drop), then stirred at RT for 2 h. 1 N aq. HCl (10 mL) was added and the mixture was extracted with EtOAc (2×5 mL). The combined organic extracts were washed with brine, then dried (Na$_2$SO$_4$) then concentrated in vacuo. The residue was purified by preparative HPLC (Column: Waters XBridge C18, 19×200 mm, 5-μm particles; Mobile Phase A: 5:95 MeCN: water with 10-mM NH$_4$OAc; Mobile Phase B: 95:5 MeCN: water with 10-mM NH$_4$OAc; Gradient: 35-70% B over 20 min, then a 5-min hold at 100% B; Flow rate: 20 mL/min) to yield the title compound (17.9 mg, 0.046 mmol, 16.4% yield) as a pale yellow oil. $^1$H NMR (500 MHz, DMSO-d$_6$) δ 7.27 (t, J=7.8 Hz, 2H), 7.17 (d, J=8.5 Hz, 2H), 6.96 (d, J=8.5 Hz, 2H), 6.90 (t, J=7.3 Hz, 1H), 6.85 (d, J=8.5 Hz, 2H), 4.47-4.37 (m, 1H), 3.95 (dd, J=10.5, 6.3 Hz, 1H), 3.80 (dd, J=10.3, 7.3 Hz, 1H), 2.71-2.64 (m, 1H), 2.14 (t, J=11.4 Hz, 2H), 1.90-1.82 (m, 1H), 1.78-1.65 (m, 2H), 1.59 (dt, J=8.4, 4.3 Hz, 1H), 1.55-1.45 (m, 2H), 1.41-1.28 (m, 2H), 1.07 (dt, J=8.7, 4.3 Hz, 1H), 0.98-0.90 (m, 1H).

Example 12

5-(4-(3-Phenoxycycloheptyl)phenyl)pentanoic acid (diastereomer 1)

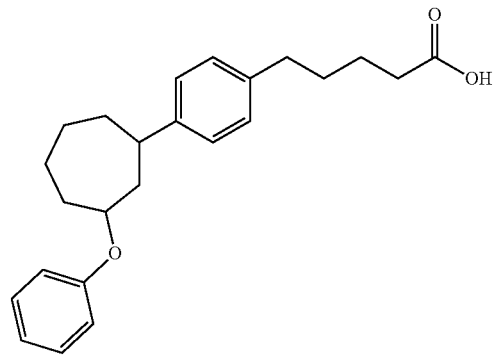 [SMILES: O=C(O)CCCCc1ccc(C2CCCCC(Oc3ccccc3)C2)cc1]

12A. Methyl 5-(4-(3-oxocycloheptyl)phenyl)pentanoate

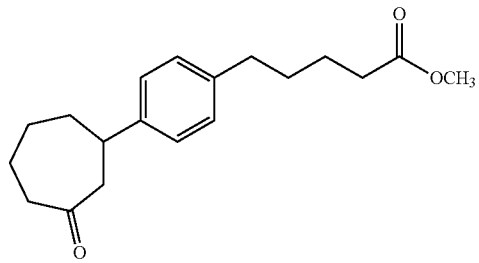 [SMILES: COC(=O)CCCCc1ccc(C2CCCCC(=O)C2)cc1]

The title compound was prepared from (4-(5-methoxy-5-oxopentyl)phenyl) boronic acid and 2-cycloheptenone by an analogous procedure to that used for the synthesis of Compound 1E. The title compound (0.58 g, 1.92 mmol, 69.7% yield) was obtained as a colorless oil. $^1$H NMR (500 MHz, CDCl$_3$) δ 7.13-7.05 (m, 4H), 3.66 (s, 3H), 2.97-2.84 (m, 2H), 2.66-2.54 (m, 5H), 2.38-2.28 (m, 2H), 2.11-1.94 (m, 3H), 1.77-1.60 (m, 6H), 1.55-1.43 (m, 1H).

12B. Methyl 5-(4-(3-hydroxycycloheptyl)phenyl)pentanoate (diastereomer 1)

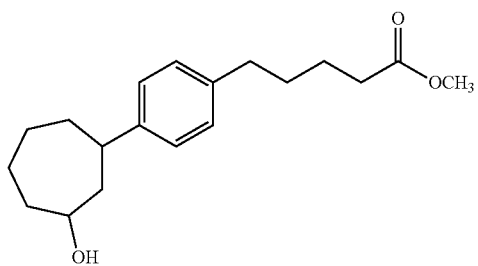 [SMILES: COC(=O)CCCCc1ccc(C2CCCCC(O)C2)cc1]

and

12C. Methyl 5-(4-(3-hydroxycycloheptyl)phenyl)pentanoate (diastereomer 2)

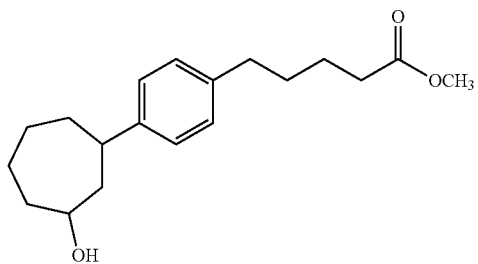 [SMILES: COC(=O)CCCCc1ccc(C2CCCCC(O)C2)cc1]

Compounds 12B and 12C were prepared from methyl 5-(4-(3-oxocycloheptyl) phenyl)pentanoate by an analogous procedure to that used for the synthesis of Compounds 1F and 1G from Compound 1E.

The faster eluting diastereomer 12B (360 mg, 1.18 mmol, 61.7% yield) was obtained as a pale yellow oil. $^1$H NMR (500 MHz, CDCl$_3$) δ 7.14-7.04 (m, 4H), 4.15 (br. s., 1H), 3.66 (s, 3H), 3.06-2.93 (m, 1H), 2.58 (t, J=7.3 Hz, 2H), 2.37-2.29 (m, 2H), 2.13-2.04 (m, 1H), 2.03-1.95 (m, 2H), 1.94-1.88 (m, 1H), 1.87-1.78 (m, 2H), 1.75-1.50 (m, 7H), 1.46-1.37 (m, 1H), 1.33 (br. s., 1H).

The slower eluting diastereomer 12C (150 mg, 0.493 mmol, 25.7% yield) was obtained as a pale yellow oil. $^1$H NMR (500 MHz, CDCl$_3$) δ 7.12-7.05 (m, 4H), 3.97-3.88 (m, 1H), 3.66 (s, 3H), 2.70-2.62 (m, 1H), 2.59 (t, J=7.3 Hz, 2H), 2.35-2.30 (m, 2H), 2.14-2.07 (m, 1H), 2.03 (br. s., 1H), 1.92-1.83 (m, 2H), 1.75 (br. s., 1H), 1.71-1.53 (m, 9H), 1.37 (d, J=3.3 Hz, 1H).

Example 12

The title compound was prepared from methyl 5-(4-(3-hydroxycycloheptyl) phenyl)pentanoate (diastereomer 1; Example 12B) by a 2-step procedure analogous to that used for the synthesis of Example 1 from Example 1F. The title compound (85 mg, 0.230 mmol, 69.9% yield) was obtained as a white solid. $^1$H NMR (500 M Hz, CDCl$_3$) δ 7.28-7.19 (m, 2H), 7.13-7.03 (m, 4H), 6.91-6.79 (m, 3H), 4.47 (ddt, J=9.9, 8.2, 4.1 Hz, 1H), 2.70 (tt, J=11.0, 2.9 Hz, 1H), 2.57 (t, J=7.0 Hz, 2H), 2.35 (t, J=6.9 Hz, 2H), 2.31-2.25 (m, 1H), 2.18-2.08 (m, 1H), 2.06-1.97 (m, 1H), 1.97-1.89 (m, 2H), 1.87-1.52 (m, 9H).

Example 13

5-(4-(3-Phenoxycycloheptyl)phenyl)pentanoic acid (diastereomer 2)

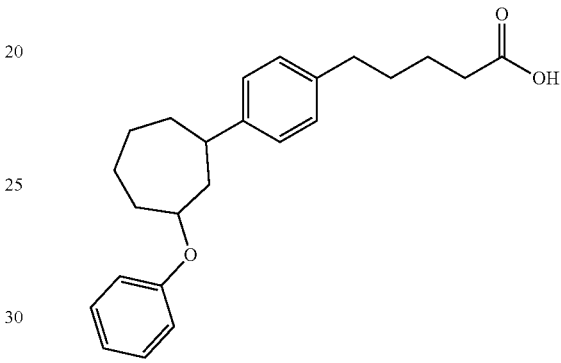

The title compound was synthesized from methyl 5-(4-(3-hydroxycycloheptyl) phenyl)pentanoate (diastereomer 2, Example 12C) using the same synthetic sequence as for the synthesis of Example 12 from 12B. The title compound (66 mg, 0.177 mmol, 67.3% yield) was obtained as a white solid. $^1$H NMR (400 MHz, CDCl$_3$) δ 7.26-7.19 (m, 2H), 7.12-7.04 (m, 4H), 6.91-6.82 (m, 3H), 4.68-4.60 (m, 1H), 3.12-3.04 (m, 1H), 2.58 (t, J=7.0 Hz, 2H), 2.41-2.33 (m, 2H), 2.29-2.20 (m, 1H), 2.14-2.03 (m, 2H), 2.02-1.84 (m, 4H), 1.75-1.55 (m, 6H), 1.54-1.39 (m, 1H).

Example 14

2-(4-(3-Phenoxycycloheptyl)phenethoxy)acetic acid (diastereomeric mixture)

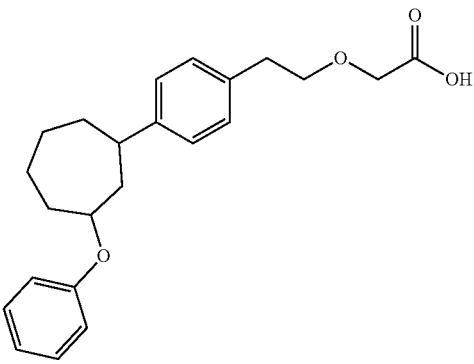 [SMILES: O=C(O)COCCc1ccc(C2CCCCC(Oc3ccccc3)C2)cc1]

14A. tert-Butyl 2-(4-(3-oxocycloheptyl)phenethoxy)acetate

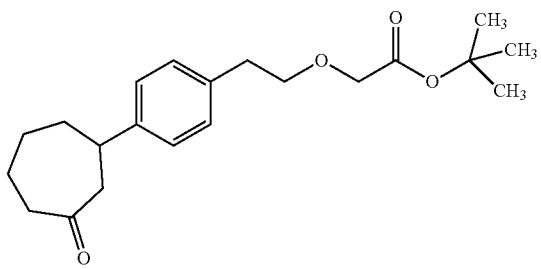 [SMILES: CC(C)(C)OC(=O)COCCc1ccc(C2CCCCC(=O)C2)cc1]

The title compound was prepared from tert-butyl 2-(4-(5,5-dimethyl-1,3,2-dioxaborinan-2-yl)phenethoxy)acetate and cyclohept-2-enone by a procedure analogous to that used for the synthesis of Compound 4C from Compound 4B and cyclohex-2-enone. The title compound (0.54 g, 1.559 mmol, 72.4% yield) was obtained as a pale yellow oil. $^1$H NMR (500 MHz, CDCl$_3$) δ 7.20-7.15 (m, 2H), 7.13-7.08 (m, 2H), 3.96 (s, 2H), 3.73 (t, J=7.3 Hz, 2H), 2.95-2.86 (m, 4H), 2.65-2.56 (m, 3H), 2.10-1.94 (m, 3H), 1.77-1.67 (m, 2H), 1.47 (s, 10H).

14B. tert-Butyl 2-(4-(3-hydroxycycloheptyl)phenethoxy)acetate (diastereomeric mixture)

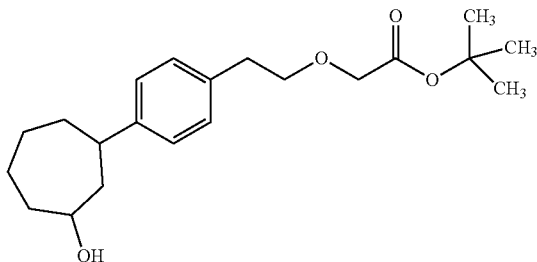 [SMILES: CC(C)(C)OC(=O)COCCc1ccc(C2CCCCC(O)C2)cc1]

To a solution of tert-butyl 2-(4-(3-oxocycloheptyl) phenethoxy)acetate (0.50 g, 1.44 mmol) and MeOH (28.9 ml) was added NaBH$_4$ (0.022 g, 0.577 mmol) and the mixture was stirred under Ar overnight. The reaction was then quenched with 1 N aq. HCl (100 mL) and extracted with EtOAc (2×50 mL). The combined organic extracts were washed with brine, dried (Na$_2$SO$_4$) and concentrated in vacuo. The residue was chromatographed (SiO$_2$; 40 g; A=Hex, B=EtOAc; 15 min gradient from 0% B to 50% B; flow rate=40 mL/min; fractions containing the desired product were identified by TLC using PMA stain) to afford the title compound (0.47 g, 1.349 mmol, 93% yield; mixture of diastereomers) as a white solid. $^1$H NMR (500 MHz, CDCl$_3$) δ 7.22-7.10 (m, 4H), 4.24-4.12 (m, 1H), 3.99 (s, 2H), 3.97-3.91 (m, 1H), 3.74 (t, J=7.4 Hz, 2H), 3.06-2.98 (m, 1H), 2.93 (t, J=7.3 Hz, 2H), 2.73-2.61 (m, 1H), 2.14-1.98 (m, 2H), 1.97-1.80 (m, 2H), 1.78-1.53 (m, 4H), 1.50 (s, 9H), 1.45-1.26 (m, 1H).

Example 14

The title compound was prepared from tert-butyl 2-(4-(3-hydroxycycloheptyl) phenethoxy)acetate by a procedure analogous to the one used for the synthesis of Example 4 from Compound 4D. The title compound (118 mg, 0.321 mmol, 50.9% yield) was obtained as a pale yellow oil. $^1$H NMR (500 MHz, DMSO-d$_6$) δ 7.33-7.19 (m, 2H), 7.18-7.07 (m, 4H), 6.89 (d, J=8.0 Hz, 3H), 4.78-4.53 (m, 1H), 3.67-3.63 (m, 2H), 3.03-2.72 (m, 4H), 2.13-1.91 (m, 3H), 1.88-1.66 (m, 6H), 1.63-1.38 (m, 2H).

Example 15

2-(4-(3-Phenoxycycloheptyl)phenethoxy)acetic acid (diastereomer 1, racemate)

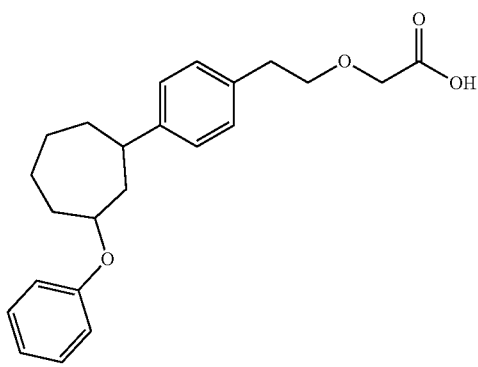 [SMILES: O=C(O)COCCc1ccc(C2CCCCC(Oc3ccccc3)C2)cc1]

Example 16

2-(4-(3-Phenoxycycloheptyl)phenethoxy)acetic acid (diastereomer 2, enantiomer 1)

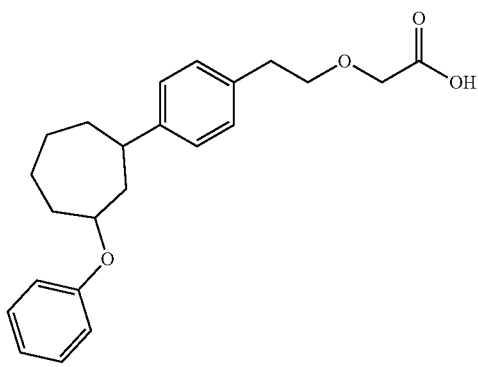 [SMILES: O=C(O)COCCc1ccc(C2CCCCC(Oc3ccccc3)C2)cc1]

Example 17

2-(4-(3-Phenoxycycloheptyl)phenethoxy)acetic acid (diastereomer 2, enantiomer 2)

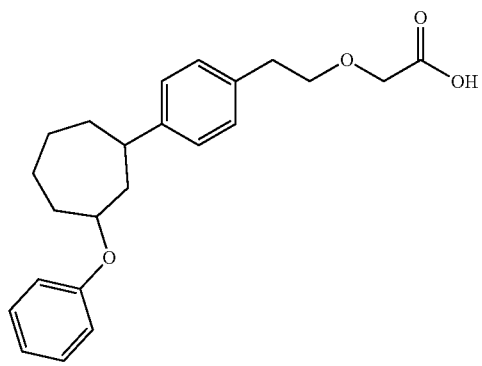 [SMILES: O=C(O)COCCc1ccc(C2CCCCC(Oc3ccccc3)C2)cc1]

The racemic diastereomers Example 14 was separated by chiral preparative HPLC (Instrument=Berger Multigram II SFC; Column: KROMASIL®, 5-CelluCoat, 21×250 mm, 5 μm; Mobile Phase: 13% EtOH/87% $CO_2$; Flow Conditions: 45 mL/min, 150 Bar, 40° C.; Detector Wavelength: 220 nm; Injection Details: 0.75 mL of 8 mg/mL in EtOH) to afford the title compounds.

The first eluting peak was a single racemic diastereomer, Example 15 (4.5 mg, 0.012 mmol, 4.9% yield), which was obtained as a tan oil. $^1$H NMR (500 MHz, $CDCl_3$) δ 7.21-7.13 (m, 3H), 7.04 (s, 3H), 6.89-6.74 (m, 3H), 4.61-4.54 (m, 1H), 4.00 (br. s., 2H), 3.70 (br. s., 2H), 3.04-3.00 (m, 1H), 2.83 (br. s., 2H), 2.19-2.10 (m, 1H), 2.05-1.97 (m, 2H), 1.93-1.77 (m, 4H), 1.67-1.52 (m, 2H), 1.45-1.33 (m, 1H). $[α]_D^{20}$=−2.7° (c=1 in MeOH).

The second eluting peak was a single chiral diastereomer, Example 16 (17.5 mg, 0.047 mmol, 19.1% yield), which was obtained as a tan oil. $^1$H NMR (500 MHz, $CDCl_3$) δ 7.22-7.13 (m, 2H), 7.05 (s, 4H), 6.85-6.74 (m, 3H), 4.40 (ddt, J=9.8, 8.2, 4.1 Hz, 1H), 4.01 (br. s., 2H), 3.69 (br. s., 2H), 2.82 (t, J=6.3 Hz, 2H), 2.71-2.57 (m, 1H), 2.21 (dd, J=13.5, 1.4 Hz, 1H), 2.12-2.02 (m, 1H), 1.99-1.57 (m, 7H), 1.55-1.44 (m, 1H). $[α]_D^{20}$=+50.2° (c=1 in MeOH).

The third eluting peak was another single chiral diastereomer, Example 17 (24 mg, 0.064 mmol, 26.4% yield), which was obtained as a tan oil. $^1$H NMR (500 MHz, $CDCl_3$) δ 7.21-7.16 (m, 2H), 7.09-7.01 (m, 4H), 6.87-6.71 (m, 3H), 4.40 (ddd, J=8.2, 5.8, 4.1 Hz, 1H), 4.02 (br. s., 2H), 3.68 (t, J=6.7 Hz, 2H), 2.82 (t, J=6.9 Hz, 2H), 2.64 (ddd, J=10.8, 8.0, 2.9 Hz, 1H), 2.21 (dd, J=13.8, 1.4 Hz, 1H), 2.12-2.03 (m, 1H), 1.98-1.60 (m, 7H), 1.56-1.46 (m, 1H). $[α]_D^{20}$=−41.9° (c=1 in MeOH).

Example 18

5-(4-(3-Phenoxycyclopentyl)phenyl)pentanoic acid (diastereomeric mixture)

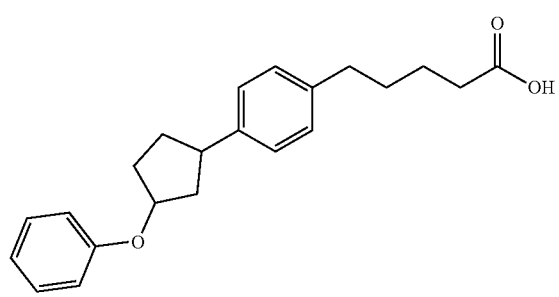 [SMILES: O=C(O)CCCCc1ccc(C2CCC(Oc3ccccc3)C2)cc1]

18A. Methyl 5-(4-(3-oxocyclopentyl)phenyl)pentanoate

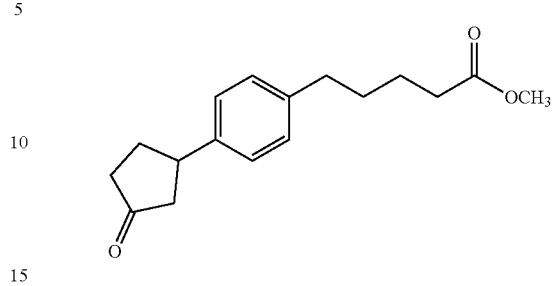

The title compound was prepared from (4-(5-methoxy-5-oxopentyl)phenyl) boronic acid and cyclopent-2-enone by a procedure analogous to that used for the synthesis of Compound 1E from 1D. The title compound (0.410 g, 1.49 mmol, 54.3% yield) was obtained as a colorless oil. $^1$H NMR (500 MHz, $CDCl_3$) δ 7.22-7.10 (m, 4H), 3.66 (s, 3H), 3.45-3.35 (m, 1H), 2.66-2.58 (m, 3H), 2.51-2.39 (m, 2H), 2.37-2.27 (m, 4H), 2.01-1.92 (m, 1H), 1.72-1.64 (m, 4H).

18B. Methyl 5-(4-(3-hydroxycyclopentyl)phenyl)pentanoate (diastereomeric mixture)

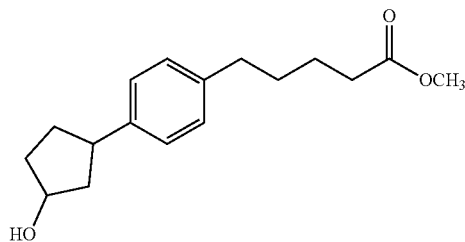 [SMILES: COC(=O)CCCCc1ccc(C2CCC(O)C2)cc1]

Compound 18B was prepared from methyl 5-(4-(3-oxocyclopentyl)phenyl) pentanoate by a procedure analogous to that used for the synthesis of Compound 14B from Compound 14A. The title compound (0.33 g, 1.194 mmol, 80% yield; mixture of diastereomers) was obtained as a pale yellow oil. $^1$H NMR (500 MHz, $CDCl_3$) δ 7.21-7.06 (m, 4H), 4.55-4.40 (m, 1H), 3.66 (s, 3H), 3.42-2.95 (m, 1H), 2.59 (t, J=7.2 Hz, 2H), 2.51-2.41 (m, 1H), 2.33 (t, J=7.2 Hz, 2H), 2.28-2.18 (m, 1H), 2.11-2.02 (m, 1H), 1.96-1.77 (m, 2H), 1.71-1.58 (m, 6H).

Example 18

The title compound was prepared from methyl 5-(4-(3-hydroxycyclopentyl) phenyl) pentanoate (diastereomeric mixture) by a procedure analogous to that used for the synthesis of Example 4 (Method A) from Example 4D. The title compound (62.6 mg, 0.185 mmol, 51.1% yield) was obtained as a pale yellow oil. $^1$H NMR (500 MHz, DMSO-$d_6$) δ 7.29 (t, J=8.0 Hz, 2H), 7.24-7.18 (m, 2H), 7.15-7.09 (m, 2H), 6.97-6.91 (m, 3H), 5.00-4.89 (m, 1H), 3.28-3.06 (m, 1H), 2.67-2.54 (m, 2H), 2.38-2.28 (m, 1H), 2.27-2.21 (m, 2H), 2.19-2.12 (m, 1H), 2.09-2.00 (m, 1H), 1.95 (ddd, J=13.6, 11.3, 6.2 Hz, 1H), 1.84-1.74 (m, 1H), 1.72-1.45 (m, 5H).

Example 19

2-(4-(3-Phenoxycyclopentyl)phenethoxy)acetic acid (diastereomer mixture)

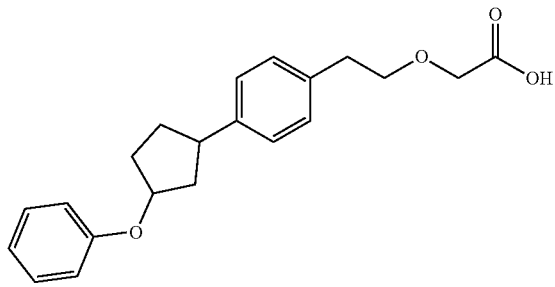 [SMILES: O=C(O)COCCc1ccc(C2CCC(Oc3ccccc3)C2)cc1]

19A. tert-Butyl 2-(4-(3-oxocyclopentyl)phenethoxy)acetate

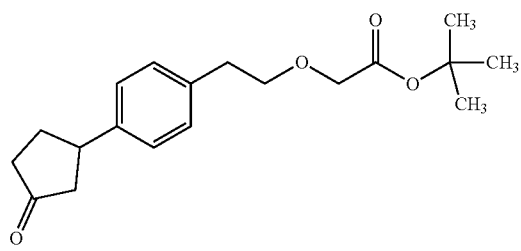 [SMILES: CC(C)(C)OC(=O)COCCc1ccc(C2CCC(=O)C2)cc1]

The title compound was prepared from tert-butyl 2-(4-(5,5-dimethyl-1,3,2-dioxaborinan-2-yl)phenethoxy)acetate and cyclopent-2-enone by a procedure analogous to that used for the synthesis of Compound 4C from Compound 4B. The title compound (0.49 g, 1.54 mmol, 35.7% yield) was obtained as a pale yellow oil. $^1$H NMR (400 MHz, CDCl$_3$) δ 7.25-7.14 (m, 4H), 3.97 (s, 2H), 3.74 (t, J=7.2 Hz, 2H), 3.45-3.33 (m, 1H), 2.94 (t, J=7.2 Hz, 2H), 2.72-2.58 (m, 1H), 2.43 (s, 2H), 2.31 (s, 2H), 2.07-1.86 (m, 1H), 1.47 (s, 9H).

19B. tert-Butyl 2-(4-(3-hydroxycyclopentyl)phenethoxy)acetate

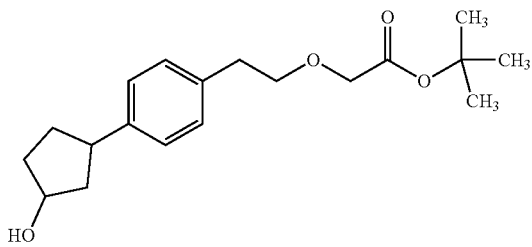 [SMILES: CC(C)(C)OC(=O)COCCc1ccc(C2CCC(O)C2)cc1]

The title compound was prepared from tert-butyl 2-(4-(3-oxocyclopentyl) phenethoxy)acetate by a procedure analogous to that used for the synthesis of Example 14B from Example 14A. The title compound (0.37 g, 1.16 mmol, 75% yield) was obtained as a pale yellow oil. $^1$H NMR (500 MHz, CDCl$_3$) δ 7.24-7.14 (m, 4H), 4.54-4.40 (m, 1H), 3.97 (s, 2H), 3.73 (t, J=7.3 Hz, 2H), 3.41-2.98 (m, 1H), 2.92 (t, J=7.3 Hz, 2H), 2.53-2.39 (m, 1H), 2.29-2.15 (m, 1H), 2.13-2.00 (m, 1H), 1.97-1.75 (m, 2H), 1.60 (br. s., 2H), 1.47 (s, 9H).

Example 19

The title compound was prepared from tert-butyl 2-(4-(3-hydroxycyclopentyl) phenethoxy)acetate by a procedure analogous to that used for the synthesis of Example 4 from Example 4D. The title compound (35.1 mg, 0.098 mmol, 28.5% yield) was obtained as a pale yellow oil. $^1$H NMR (500M Hz, DMSO-d$_6$) δ 7.32-7.25 (m, 2H), 7.22-7.14 (m, 4H), 6.96-6.85 (m, 3H), 5.02-4.84 (m, 1H), 3.98 (d, J=2.8 Hz, 2H), 3.66-3.62 (m, 2H), 3.12-3.03 (m, 1H), 2.79 (td, J=6.9, 4.5 Hz, 2H), 2.37-2.29 (m, 1H), 2.19-2.11 (m, 1H), 2.06-1.88 (m, 2H), 1.85-1.74 (m, 1H), 1.71-1.57 (m, 1H).

Example 20

5-(4-(3-Phenoxypiperidin-1-yl)phenyl)pentanoic acid

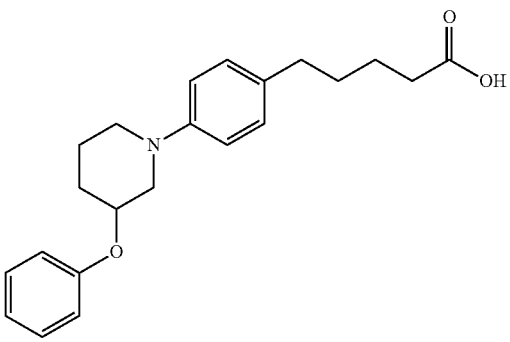 [SMILES: O=C(O)CCCCc1ccc(N2CCCC(Oc3ccccc3)C2)cc1]

Step 1: A mixture of 1D (50 mg, 0.212 mmol), 3-phenoxypiperidine (45.0 mg, 0.254 mmol), pyridine (0.034 mL, 0.424 mmol), DCM (2 mL) and 4 Å MS (50 mg). was stirred for 15 min at rt, then Cu(OAc)$_2$ (38.5 mg, 0.212 mmol) was added and the reaction was stirred at reflux for 18 h under dry air, then cooled to rt, filtered and concentrated in vacuo. The residue was purified by preparative HPLC (10 min gradient from 60% A:40% B to 0% A:100% B; (A=10% MeOH/90% H$_2$O+0.1% TFA); (B=90% MeOH/10% H$_2$O+0.1% TFA); Detection at 220 nm; PHENOMENEX® Axia 5μ C$_{18}$, 30×100 mm) to afford the N-phenyl piperidine product as a colorless residue. LCMS [M+1]$^+$=368.

A mixture of this N-phenyl piperidine ester (3.5 mg, 9.52 μmol), LiOH (1.1 mg, 0.048 mmol), THF (1 mL) and water (1 mL) was stirred at rt for 3 h. The mixture was then diluted with 10% aq. citric acid (10 mL) and extracted with EtOAc (10 mL). The organic phase was washed with brine, dried (Na$_2$SO$_4$) and concentrated in vacuo. The residue was purified by preparative HPLC (Method: Gradient Solv. System: From 60% A:40% B to 0% A:100% B; (A=10% MeOH/90% H$_2$O+0.1% TFA); (B=90% MeOH/10% H$_2$O+0.1% TFA); Detection at 220 nm; 10 min gradient; PHENOMENEX® Axia 5μ C18, 30×100 mm) to afford the title compound (3.3 mg, 8.6 μmol, 4.1% yield) as a colorless residue. $^1$H NMR (500 MHz, CD$_2$Cl$_2$) δ 7.40 (d, J=8.5 Hz, 2H), 7.28-7.18 (m, 4H), 6.96-6.89 (m, 3H), 4.93-4.83 (m, 1H), 3.76 (dd, J=11.7, 3.4 Hz, 1H), 3.60-3.52 (m, 1H), 3.31-3.18 (m, 2H), 2.59 (t, J=7.0 Hz, 2H), 2.27 (t, J=6.7 Hz, 2H), 2.20 (dd, J=8.9, 4.0 Hz, 1H), 2.16-2.09 (m, 2H), 1.76-1.67 (m, 1H), 1.62-1.53 (m, 4H).

Example 21

2-(4-(3-Phenoxypiperidin-1-yl)phenethoxy)acetic acid

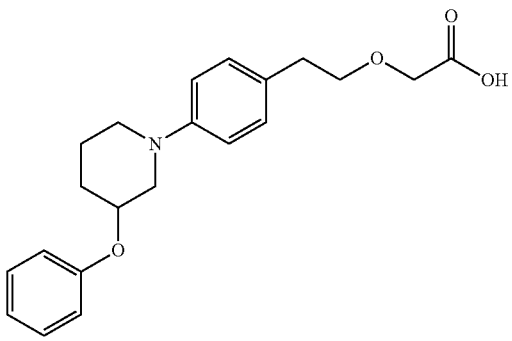

A mixture of tert-butyl 2-(4-bromophenethoxy)acetate (100 mg, 0.317 mmol), 3-phenoxypiperidine (112 mg, 0.635 mmol), $Cs_2CO_3$ (413 mg, 1.269 mmol) and toluene (2 mL; deoxygenated by vigorously bubbling Ar through it for at least 1 h) was purged and degassed with Ar, then Xantphos (36.7 mg, 0.063 mmol) and Pd(OAc)$_2$ (14.3 mg, 0.063 mmol) were added and the reaction mixture was purged and degassed again, then was stirred at 110° C. for 18 h and cooled to rt. The mixture was filtered and the filtrate was concentrated in vacuo. The residue was chromatographed (SiO$_2$; 12 g; A=Hex, B=EtOAc; 15 min gradient from 0% B to 35% B; flow rate=12 mL/min) to afford the phenyl piperidine product as a colorless oil. LCMS [M+1]$^+$=412.

This material was dissolved in DCM (1 mL) and TFA (1 mL) was added. The reaction was stirred for 2 h at rt and then concentrated in vacuo. The residue was purified by preparative HPLC (Method: Gradient Solv. System: From 100% A:0% B to 0% A: 100% B; (A=10% MeCN/90% H$_2$O+0.1% TFA); (B=90% MeCN/10% H$_2$O+0.1% TFA); Detection at 220 nm; 10 min gradient; PHENOMENEX® Axia 5µ C18, 30×100 mm) to afford the title compound (54.3 mg, 0.119 mmol, 59.6% yield) as an off-white solid. $^1$H NMR (500 MHz, CD$_3$OD) δ 7.42-7.34 (m, 4H), 7.26-7.20 (m, 2H), 7.00-6.95 (m, 2H), 6.94-6.88 (m, 1H), 4.76-4.71 (m, 1H), 3.96 (s, 2H), 3.74 (dd, J=12.7, 2.8 Hz, 1H), 3.66 (t, J=6.6 Hz, 2H), 3.64-3.59 (m, 1H), 3.55 (dd, J=12.5, 4.8 Hz, 1H), 3.46-3.39 (m, 1H), 2.86 (t, J=6.6 Hz, 2H), 2.19 (td, J=6.8, 3.4 Hz, 1H), 1.98-1.91 (m, 2H), 1.90-1.83 (m, 1H).

Example 22

(R)-5-(4-(3-Phenoxypiperidin-1-yl)phenyl)pentanoic acid

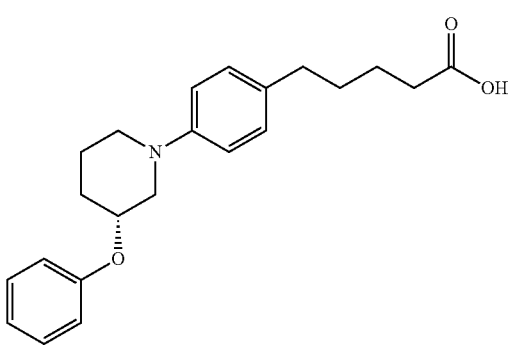 [SMILES: O=C(O)CCCCc1ccc(N2CCC[C@@H](Oc3ccccc3)C2)cc1]

22A. (E)-5-(4-Bromophenyl)pent-4-enoic acid

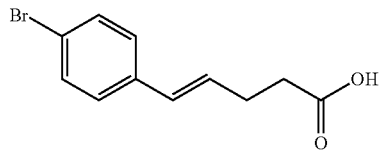 [SMILES: O=C(O)CC/C=C/c1ccc(Br)cc1]

To a solution of 3-carboxypropyltriphenylphosphonium bromide (15 g, 34.9 mmol) in DMSO (30 mL) was added KOtBu (1 M solution in THF) (73.4 mL, 73.4 mmol) at rt, during which time a slight exotherm was observed. After stirring for 40 min at rt, 4-bromobenzaldehyde (6.46 g, 34.9 mmol) was added slowly. The reaction mixture was stirred at rt for 16 h, then was quenched with water (200 mL), then washed with EtOAc/hexanes (1:1). The aqueous layer was neutralized with conc. aq. HCl (pH=2), then extracted with EtOAc. The organic layer was concentrated in vacuo and the residue was chromatographed (SiO$_2$; 160 g, continuous gradient from 100% hexanes-100% EtOAc) to afford the title compound (5.6 g, 21.95 mmol, 62.8% yield). $^1$H NMR (500 MHz, CDCl$_3$) δ 7.48-7.40 (m, 2H), 7.26-7.20 (m, 2H), 6.48-6.36 (m, 1H), 6.30-6.15 (m, 1H), 2.61-2.53 (m, 4H).

22B. 5-(4-Bromophenyl)pentanoic acid

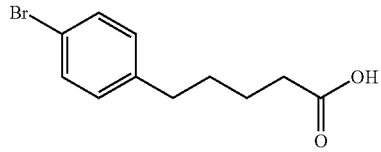 [SMILES: O=C(O)CCCCc1ccc(Br)cc1]

To a solution of (E)-5-(4-bromophenyl)pent-4-enoic acid (5.6 g, 22.0 mmol) in isopropanol (40 mL) was added platinum on sulfide, 5 wt. % on carbon (2 g, 22.0 mmol) under N$_2$. The mixture was stirred under H$_2$ (1 atm) for 3 h, then was filtered; the filtrate was concentrated in vacuo to afford the title compound (5.2 g, 20.2 mmol, 92% yield). $^1$H NMR (500 MHz, CDCl$_3$) δ 7.44-7.38 (m, 2H), 7.12-7.02 (m, 2H), 2.65-2.57 (m, 2H), 2.45-2.34 (m, 2H), 1.75-1.63 (m, 4H).

22C. Methyl 5-(4-bromophenyl)pentanoate

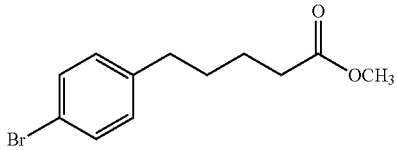 [SMILES: COC(=O)CCCCc1ccc(Br)cc1]

To a rt mixture of 5-(4-bromophenyl)pentanoic acid (2 g, 7.78 mmol), DCM (30 mL) and DMF (0.060 mL, 0.778 mmol) was added dropwise oxalyl chloride (0.817 mL, 9.33 mmol) and the reaction was stirred under Ar at rt for 1 h. Volatiles were removed in vacuo and the residue was dissolved in DCM (10 mL). This solution was added dropwise to a 0° C. suspension of K$_2$CO$_3$ (5.38 g, 38.9 mmol) in MeOH (30 mL). The reaction mixture was warmed to rt over 2 h, then was diluted with 10% aq. citric acid (100 mL), and extracted with EtOAc (2×50 mL). The combined organic extracts were washed with brine, dried (Na$_2$SO$_4$), and concentrated in vacuo. The residue was chromatographed (SiO$_2$; 80 g; A=Hex, B=EtOAc; 25 min gradient; 0% B to 50% B flow rate=60 mL/min) to afford the title compound (1.74 g, 6.42 mmol, 82% yield) as a pale yellow oil. $^1$H NMR (500 MHz, CD$_3$CN) δ 7.49-7.42 (m, 2H), 7.21-7.10 (m, 2H), 3.63 (s, 3H), 2.67-2.58 (m, 2H), 2.36-2.28 (m, 2H), 1.67-1.55 (m, 4H).

22D. (R)-3-Phenoxypiperidine

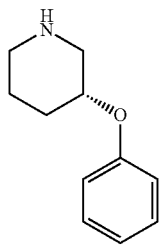

Step 1: To a 0° C. mixture of (S)-tert-butyl 3-hydroxypiperidine-1-carboxylate (1 g, 4.97 mmol), phenol (0.935 g, 9.94 mmol) and Ph$_3$P (2.61 g, 9.94 mmol) in THF (10 ml) was added dropwise DIAD (1.93 mL, 9.94 mmol). The reaction was allowed to warm slowly to rt overnight, then was concentrated in vacuo. The residue was chromatographed (SiO$_2$; 80 g; A=Hex, B=EtOAc; 20 min gradient; 0% B to 70% B flow rate=60 mL/min) to afford the desired phenoxypiperidine as a pale yellow oil (product contains phenol as an impurity which is removed in the next step).

A solution of this material in TFA (10 mL) and DCM (10 mL) was stirred at rt for 3 h, after which volatiles were removed in vacuo; the residue was dissolved in 1 N aq. HCl (20 mL) and washed with EtOAc (3×10 mL) to remove the phenol impurity from the prior step. The aq. phase was then neutralized with solid NaHCO$_3$, and saturated with NaCl, then was extracted successively with EtOAc (3×10 mL) and 10% IPA/CHCl$_3$ (3×10 mL). The combined organic extracts were dried (Na$_2$SO$_4$) and concentrated in vacuo to afford the title compound (0.12 g, 0.677 mmol, 13.7% yield) as a tan oil. $^1$H NMR (400 MHz, CD$_2$Cl$_2$) δ 7.22-7.15 (m, 2H), 6.87-6.78 (m, 3H), 4.19 (tt, J=7.4, 3.5 Hz, 1H), 3.07 (dd, J=12.4, 2.1 Hz, 1H), 2.82-2.62 (m, 3H), 1.97-1.90 (m, 1H), 1.75-1.58 (m, 2H), 1.49-1.37 (m, 1H).

Example 22

A mixture of methyl 5-(4-bromophenyl)pentanoate (30 mg, 0.111 mmol), (R)-3-phenoxypiperidine (23.5 mg, 0.133 mmol) and Cs$_2$CO$_3$ (144 mg, 0.443 mmol) in toluene (1 mL; deoxygenated by vigorously bubbling Ar through it for at least 1 h) was purged and degassed with Ar, then Xantphos (12.8 mg, 0.022 mmol) and Pd(OAc)$_2$ (5.0 mg, 0.022 mmol) was added and the reaction mixture was purged and degassed again. The reaction was stirred at 110° C. for 18 h, then was cooled to rt, filtered and the filtrate was concentrated in vacuo. The residue was chromatographed (SiO$_2$; 4 g; A=Hex, B=EtOAc; 15 min gradient from 0% B to 100% B; flow rate=4 mL/min) to yield the desired phenylpiperidine product (30 mg, 0.082 mmol, 73.8% yield) as a pale yellow oil. LCMS [M+1]$^+$=368.

A mixture of this phenylpiperidine ester (30 mg, 0.082 mmol) and LiOH.H$_2$O (9.78 mg, 0.408 mmol) in water (1 mL) and THF (1 mL) was stirred overnight at rt, then was acidified with conc. HCl (4 drops) and the mixture was concentrated in vacuo. The residue was purified by preparative HPLC (Method: Continuous gradient from 80% A:20% B to 0% A:100% B; (A=10% MeCN/90% H$_2$O+0.1% TFA); (B=90% MeCN/10% H$_2$O+0.1% TFA); detection at 220 nm; 10 min gradient; PHENOMENEX® Axia 5µ C18, 30×100 mm) to afford the title compound (2.0 mg, 5.62 µmol, 6.9% yield) as a tan oil. $^1$H NMR (500 MHz, CDCl$_3$) δ 7.36-7.27 (m, 2H), 7.09 (d, J=8.8 Hz, 2H), 7.01-6.96 (m, 3H), 6.93 (d, J=8.5 Hz, 2H), 4.52 (tt, J=8.9, 4.3 Hz, 1H), 3.82-3.76 (m, 1H), 3.49 (dt, J=12.0, 3.9 Hz, 1H), 2.94-2.83 (m, 2H), 2.58 (t, J=7.2 Hz, 2H), 2.42-2.35 (m, 2H), 2.25-2.19 (m, 1H), 2.02-1.93 (m, 1H), 1.87-1.78 (m, 1H), 1.73-1.60 (m, 5H).

Example 23

(S)-5-(4-(3-Phenoxypiperidin-1-yl)phenyl)pentanoic acid

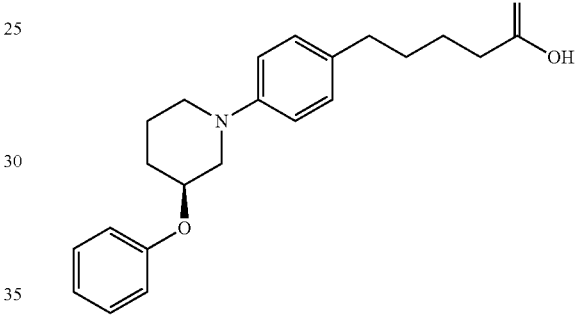

23A. (S)-3-Phenoxypiperidine

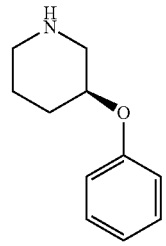 [SMILES: c1ccc(O[C@H]2CCCNC2)cc1]

The title compound was prepared from (R)-tert-butyl 3-hydroxypiperidine-1-carboxylate and phenol using an analogous procedure to that used for the synthesis of (R)-3-phenoxypiperidine (Compound 22D) from (S)-tert-butyl 3-hydroxypiperidine-1-carboxylate and phenol. The title compound (59 mg, 0.333 mmol, 7.2% yield) was obtained as a tan oil. $^1$H NMR (500 MHz, CDCl$_3$) δ 7.33-7.26 (m, 2H), 6.98-6.93 (m, 3H), 4.39-4.31 (m, 1H), 3.22 (d, J=11.8 Hz, 1H), 2.98-2.70 (m, 3H), 2.08-1.98 (m, 1H), 1.92-1.74 (m, 2H), 1.58 (br. s., 1H).

Example 23

The title compound was prepared from (S)-3-phenoxypiperidine by an analogous procedure used for the synthesis of Example 22. The title compound (12.2 mg, 0.034 mmol, 30.8% yield over 2 steps) was obtained as a tan oil. $^1$H NMR (500 MHz, CDCl$_3$) δ 7.35-7.27 (m, 2H), 7.11-7.06 (m, 2H), 7.02-6.96 (m, 3H), 6.92-6.87 (m, 2H), 4.49 (tt, J=8.9, 4.3 Hz, 1H), 3.81-3.74 (m, 1H), 3.48 (dt, J=12.0, 3.9 Hz, 1H), 2.92-2.81 (m, 2H), 2.58 (t, J=7.2 Hz, 2H), 2.44-2.36 (m, 2H), 2.25-2.17 (m, 1H), 2.00-1.92 (m, 1H), 1.85-1.75 (m, 1H), 1.72-1.61 (m, 5H).

Example 24

(S)-5-(4-(3-(4-Fluorophenoxy)piperidin-1-yl)phenyl)pentanoic acid

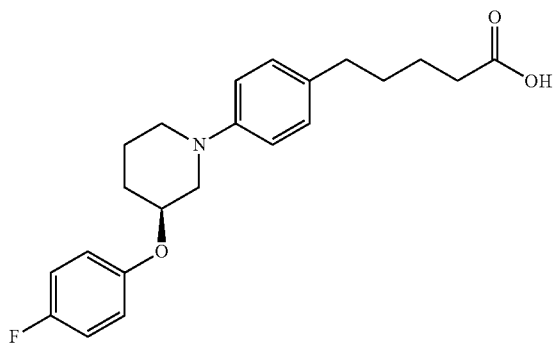 [SMILES: O=C(O)CCCCc1ccc(N2CCC[C@H](Oc3ccc(F)cc3)C2)cc1]

24A. (S)-3-(4-Fluorophenoxy)piperidine

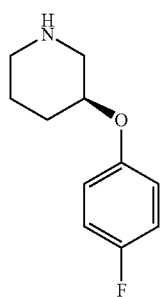 [SMILES: Fc1ccc(O[C@H]2CCCNC2)cc1]

The title compound was prepared from (R)-tert-butyl 3-hydroxypiperidine-1-carboxylate and 4-fluorophenol by an analogous procedure to that used for the synthesis of (R)-3-phenoxypiperidine (Compound 22D). The title compound (0.142 g, 0.727 mmol, 14.6% yield) was obtained as a dark tan oil. $^1$H NMR (500 MHz, CDCl$_3$) δ 7.02-6.95 (m, 2H), 6.93-6.85 (m, 2H), 4.30 (br. s., 1H), 3.24 (br. s., 1H), 3.07-2.78 (m, 3H), 2.05-1.95 (m, 1H), 1.93-1.83 (m, 1H), 1.78 (d, J=7.7 Hz, 1H), 1.72-1.52 (m, 1H).

Example 24

The title compound was prepared from (S)-3-(4-fluorophenoxy)piperidine by an analogous procedure to that used for the synthesis of Example 22. The title compound (20 mg, 0.051 mmol, 34.3% yield over 2 steps) was obtained as a pale yellow oil. $^1$H NMR (500 MHz, DMSO-d$_6$) δ 7.14-7.08 (m, 2H), 7.05-6.97 (m, 4H), 6.84 (d, J=8.4 Hz, 2H), 4.49-4.41 (m, 1H), 3.61-3.55 (m, 1H), 2.92-2.81 (m, 2H), 2.47 (t, J=6.9 Hz, 3H), 2.20 (t, J=6.9 Hz, 2H), 2.09-2.01 (m, 1H), 1.88-1.79 (m, 1H), 1.66 (dd, J=9.9, 3.5 Hz, 1H), 1.59-1.42 (m, 5H).

Example 25

(S)-5-(2,6-Difluoro-4-(3-phenoxypiperidin-1-yl)phenyl)pentanoic acid

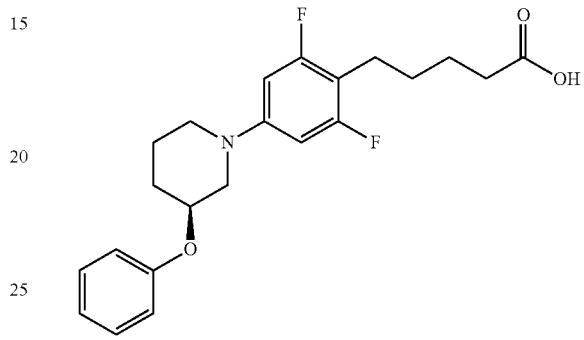

25A. (E)-5-(4-Bromo-2,6-difluorophenyl)pent-4-enoic acid

To a RT suspension of (3-carboxypropyl)-triphenylphosphonium bromide (2.91 g, 6.79 mmol) in THF (100 mL) was added dropwise NaN(TMS)$_2$ (13.57 mL of a 1 N solution in THF; 13.57 mmol) over 10 min under Ar. The mixture was stirred at rt for 1.5 h, after which the suspension became dark orange. To this mixture was added 4-bromo-2,6-difluorobenzaldehyde (1.0 g, 4.52 mmol) and the reaction was stirred at rt overnight under Ar, then was quenched with 10% aq. citric acid and water (200 mL) was added. The aqueous phase was extracted with EtOAc (2×100 mL). The combined organic extracts were washed with brine, dried (Na$_2$SO$_4$) and concentrated in vacuo. The residue was chromatographed (SiO$_2$; 80 g; A=Hex, B=EtOAc/1% AcOH; 40 min gradient from 0% B to 60% B; flow rate=60 mL/min) to afford the title compound (0.97 g, 3.33 mmol, 73.6% yield) as a pale yellow solid. $^1$H NMR (500 MHz, CD$_3$OD) δ 7.17-7.04 (m, 2H), 6.49-6.26 (m, 1H), 6.04-5.84 (m, 1H), 2.42 (t, J=6.7 Hz, 1H), 2.40-2.34 (m, 1H), 2.29-2.24 (m, 1H), 2.21-2.14 (m, 1H).

25B. (E)-Methyl 5-(4-bromo-2,6-difluorophenyl)pent-4-enoate

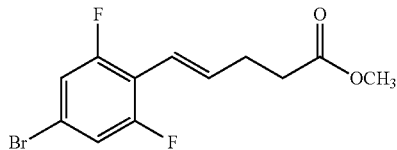 [SMILES: COC(=O)CC/C=C/c1c(F)cc(Br)cc1F]

To a mixture of (E)-5-(4-bromo-2,6-difluorophenyl)pent-4-enoic acid (0.3 g, 1.03 mmol), MeOH (0.334 mL, 8.24 mmol) and DMAP (0.252 g, 2.061 mmol) in DCM (5 mL) was added EDC (0.395 g, 2.06 mmol) and the reaction was stirred overnight at rt. Volatiles were removed in vacuo and the residue was chromatographed (SiO$_2$; 24 g cartridge; A=Hex, B=EtOAc; 15 min gradient from 0% B to 50% B; flow rate=24 mL/min) to afford the title compound (0.208 g, 0.682 mmol, 66.1% yield) as a pale yellow oil. $^1$H NMR (400 MHz, CDCl$_3$) δ 7.15-7.02 (m, 2H), 6.58-6.33 (m, 1H), 6.18-5.89 (m, 1H), 3.70 (d, J=15.0 Hz, 3H), 2.58 (t, J=6.4 Hz, 1H), 2.55-2.49 (m, 1H), 2.47-2.41 (m, 1H), 2.39-2.31 (m, 1H).

Example 25

A mixture of (E)-methyl 5-(4-bromo-2,6-difluorophenyl)pent-4-enoate 25B (50 mg, 0.164 mmol), (S)-3-phenoxypiperidine 23A (29.0 mg, 0.164 mmol), Cs$_2$CO$_3$ (214 mg, 0.655 mmol) in toluene (1 mL; deoxygenated by vigorously bubbling Ar through it for at least 1 h) was purged and degassed with Ar. Xantphos (19.0 mg, 0.033 mmol) and Pd(OAc)$_2$ (7.4 mg, 0.033 mmol) were added and the reaction vessel was purged and degassed again, then was stirred at 110° C. overnight, then was cooled to rt. The reaction mixture was filtered and the filtrate was concentrated in vacuo. The residue was chromatographed (SiO$_2$; 4 g; A=Hex, B=EtOAc; 15 min gradient from 0% B to 60% B; flow rate=4 mL/min) to afford the desired phenylpiperidine product (20 mg, 0.050 mmol, 30.4% yield) as a tan oil. LCMS [M+1]$^+$=402.

A mixture of the phenylpiperidine ester from the first step (20 mg, 0.050 mmol) and 2 N aq. NaOH in MeOH (1 mL) was stirred overnight at rt, then was diluted was 10% aq. citric acid (10 mL) and extracted with EtOAc (2×5 mL). The combined organic extracts were washed with brine, dried (Na$_2$SO$_4$) and concentrated in vacuo to afford the desired phenylpiperidine acid (19 mg, 0.049 mmol, 98% yield) as a tan oil. LCMS [M+1]$^+$=388.

A solution of the phenylpiperidine alkene acid from the previous step (19 mg, 0.049 mmol) and MeOH (5 mL) was flushed with Ar, then Pd—C (5.2 mg, 4.90 μmol) was added and the reaction was flushed and evacuated with Ar. The vessel was then placed under an atmosphere of H$_2$ and the reaction was stirred overnight at rt. The catalyst was filtered off and the filtrate was concentrated in vacuo. The residue was purified by preparative HPLC (Column: Waters XBridge C18, 19×200 mm, 5-μm particles; Mobile Phase A:5:95 MeCN: water with 10 mM aq. NH$_4$OAc; Mobile Phase B: 95:5 MeCN: water with 10 mM aq. NH$_4$OAc; Gradient: 35-70% B over 20 min, then a 5-min hold at 100% B; Flow: 20 mL/min) to yield the title compound (1.3 mg, 3.27 μmol, 6.67% yield) as a colorless residue. $^1$H NMR (500 MHz, DMSO-d$_6$) δ 7.29 (s, 2H), 6.97 (d, J=8.5 Hz, 3H), 6.57 (d, J=10.7 Hz, 2H), 4.55-4.45 (m, 1H), 3.67-3.61 (m, 1H), 3.14-3.00 (m, 3H), 2.49 (br. s., 2H), 2.17 (br. s., 2H), 2.10-2.01 (m, 1H), 1.87-1.77 (m, 1H), 1.66-1.56 (m, 2H), 1.48 (br. s., 4H).

Example 26

(S)-5-(2-Fluoro-4-(3-phenoxypiperidin-1-yl)phenyl)pentanoic acid

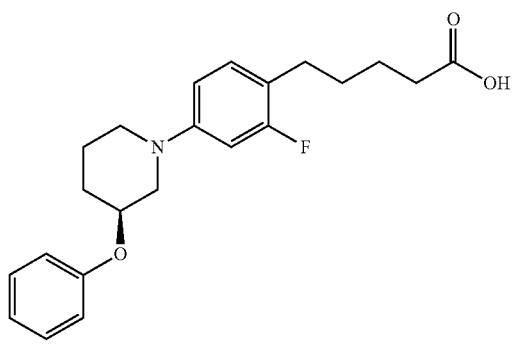 [SMILES: O=C(O)CCCCc1ccc(N2CCC[C@H](Oc3ccccc3)C2)cc1F]

26A. (E)-Methyl 5-(4-bromo-2-fluorophenyl)pent-4-enoate

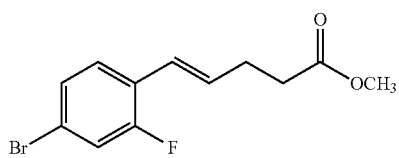 [SMILES: COC(=O)CC/C=C/c1ccc(Br)cc1F]

The title compound was prepared from 4-bromo-2-fluorobenzaldehyde by an analogous sequence to that used for the synthesis of (E)-5-(4-bromo-2,6-difluorophenyl) pent-4-enoic acid 25B. The title compound (0.25 g, 0.871 mmol, 67.2% yield over 2 steps) was obtained as a pale yellow oil. $^1$H NMR (400 MHz, CDCl$_3$) δ 7.36-7.13 (m, 3H), 6.56-6.36 (m, 1H), 6.35-5.75 (m, 1H), 3.81-3.62 (m, 3H), 2.67-2.40 (m, 4H).

Example 26

The title compound was prepared from (E)-methyl 5-(4-bromo-2-fluorophenyl)pent-4-enoate using the same synthetic sequence as for the synthesis of Example 25. The title compound (5.4 mg, 0.014 mmol, 8.19% yield over 3 steps) was obtained as an oil. $^1$H NMR (500 MHz, DMSO-d$_6$) δ 7.30 (t, J=7.4 Hz, 2H), 7.06 (t, J=8.5 Hz, 1H), 7.02-6.91 (m, 3H), 6.71-6.64 (m, 2H), 4.50 (br. s., 1H), 3.63 (d, J=11.8 Hz, 1H), 3.05-2.89 (m, 3H), 2.49 (br. s., 2H), 2.21 (br. s., 2H), 2.06 (d, J=5.5 Hz, 1H), 1.83 (br. s., 1H), 1.70-1.55 (m, 2H), 1.50 (br. s., 4H).

Example 27

2-(3-(4-(3-Phenoxypiperidin-1-yl)phenyl)propoxy)acetic acid

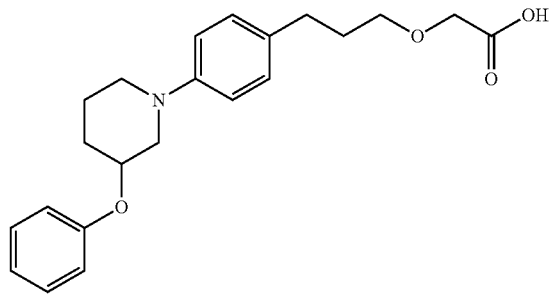 [SMILES: O=C(O)COCCCc1ccc(N2CCCC(Oc3ccccc3)C2)cc1]

27A. tert-Butyl 2-(3-(4-bromophenyl)propoxy)acetate

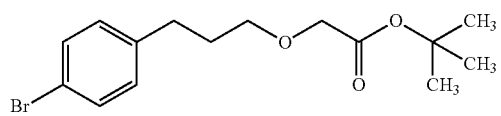 [SMILES: CC(C)(C)OC(=O)COCCCc1ccc(Br)cc1]

To a 0° C. mixture of 3-(4-bromophenyl)propan-1-ol (3.0 g, 14.0 mmol) and Bu$_4$NCl.H$_2$O (1.94 g, 6.97 mmol) in toluene (100 mL) was added NaOH (22.3 mL of a 30% w/v aq. solution; 167 mmol) followed by tert-butyl 2-bromoacetate (3.79 mL, 25.6 mmol). The reaction was stirred vigorously overnight, then was diluted with water (100 mL) and extracted with EtOAc (2×50 mL). The combined organic extracts were washed with brine, dried (Na$_2$SO$_4$), and concentrated in vacuo. The residue was chromatographed (SiO$_2$; 80 g; A=Hex, B=EtOAc; 15 min gradient from 0% B to 50% B; flow rate=60 mL/min) to afford the title compound (2.45 g, 7.44 mmol, 53.4% yield) as a colorless oil. $^1$H NMR (400 MHz, CD$_2$Cl$_2$) δ 7.47-7.41 (m, 2H), 7.14 (d, J=8.6 Hz, 2H), 3.95 (s, 2H), 3.53 (t, J=6.3 Hz, 2H), 2.74-2.67 (m, 2H), 1.96-1.86 (m, 2H), 1.50 (s, 9H).

Example 27

The title compound was prepared from tert-butyl 2-(3-(4-bromophenyl) propoxy)acetate using the same synthetic sequence as used for the preparation of Example 21. The title compound (58.4 mg, 0.152 mmol, 67.2% yield over 2 steps) was obtained as a tan oil. $^1$H NMR (500 MHz, CD$_2$Cl$_2$) δ 7.42 (d, J=8.8 Hz, 2H), 7.36-7.29 (m, 4H), 7.08-6.98 (m, 3H), 4.96-4.88 (m, 1H), 4.05 (s, 2H), 3.86 (dd, J=11.7, 3.7 Hz, 1H), 3.64 (dt, J=11.9, 3.7 Hz, 1H), 3.54 (t, J=6.2 Hz, 2H), 3.31-3.21 (m, 2H), 2.74 (t, J=7.6 Hz, 2H), 2.35-2.26 (m, 1H), 2.20-2.12 (m, 2H), 1.97-1.87 (m, 2H), 1.84-1.72 (m, 1H).

Example 28

(+/−)-2-((4-(3-Phenoxypiperidin-1-yl)phenoxy)methyl)cyclopropanecarboxylic acid (cis-Configuration; Absolute Stereochemistry is Arbitrarily Drawn)

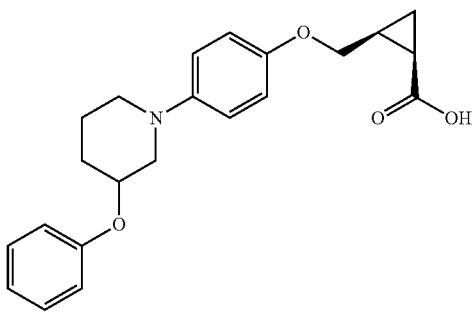 [SMILES: O=C(O)[C@@H]1C[C@@H]1COc1ccc(N2CCCC(Oc3ccccc3)C2)cc1]

28A. (±)-2-(Methoxycarbonyl)cyclopropanecarboxylic acid

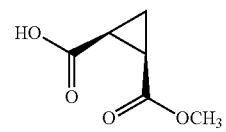

A mixture of (1R,2S)-dimethyl cyclopropane-1,2-dicarboxylate (5.0 g, 31.6 mmol), NaOH (1.265 g, 31.6 mmol), MeOH (120 mL) and water (10 mL) was stirred overnight at rt, and then was acidified with 1 N aq. HCl (150 mL) and extracted with EtOAc (2×100 mL). The combined organic extracts were washed with brine, dried (Na$_2$SO$_4$), and concentrated in vacuo to afford the title compound (4.24 g, 29.4 mmol, 93% yield) as a pale yellow oil. $^1$H NMR (500 MHz, CDCl$_3$) δ 3.69 (s, 3H), 2.16-2.04 (m, 2H), 1.71-1.64 (m, 1H), 1.31 (td, J=8.5, 5.1 Hz, 1H).

28B. (±)-Methyl 2-(hydroxymethyl)cyclopropanecarboxylate

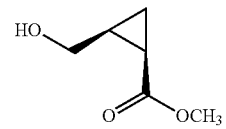

To a 0° C. solution of (±)-2-(methoxycarbonyl)cyclopropanecarboxylic acid (4.24 g, 29.4 mmol) in THF (75 mL) was added dropwise BH$_3$.THF complex (29.4 mL of a 1 M solution in THF; 29.4 mmol). The reaction was allowed to warm slowly to RT under Ar overnight, then was cautiously quenched by adding AcOH (5 mL) and stirring for 15 min. The mixture was neutralized with sat. aq. NaHCO$_3$ (50 mL) and extracted with EtOAc (50 mL). The organic phase was washed with brine, dried (Na$_2$SO$_4$) and concentrated in vacuo. The residue was chromatographed (SiO$_2$; 80 g;

A=Hex, B=EtOAc; 20 min gradient from 0% B to 50% B; flow rate=60 mL/min; fractions containing product were identified by TLC using KMnO₄ stain; TLC R$_f$=0.5, 2:1 Hex:EtOAc) to afford the title compound (1.65 g, 12.68 mmol, 43.1% yield) as a pale yellow oil. ¹H NMR (400 MHz, CDCl₃) δ 3.94 (dd, J=11.8, 5.2 Hz, 1H), 3.75 (dd, J=11.7, 8.1 Hz, 1H), 3.71 (s, 3H), 2.32 (br. s., 1H), 1.83-1.74 (m, 1H), 1.61 (td, J=7.9, 5.3 Hz, 1H), 1.18-1.09 (m, 2H).

28C. (±)-Methyl 2-((4-bromophenoxy)methyl)cyclopropanecarboxylate

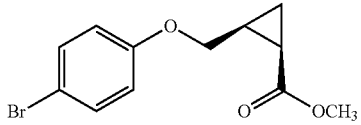 [SMILES: COC(=O)[C@@H]1C[C@@H]1COc1ccc(Br)cc1]

To a 0° C. solution of (±)-methyl 2-(hydroxymethyl) cyclopropanecarboxylate (1.65 g, 12.68 mmol), 4-bromophenol (4.39 g, 25.4 mmol) and Ph₃P (7.65 g, 29.2 mmol) in THF (16.90 ml) was added dropwise DIAD (5.67 ml, 29.2 mmol). The reaction was allowed to slowly warm to rt overnight, then was heated to 65° C. and stirred at 65° C. overnight. The reaction was then cooled to rt and volatiles were removed in vacuo. The residue was chromatographed (SiO₂; 120 g cartridge; A=Hex, B=EtOAc; 30 min gradient from 0% B to 50% B; flow rate=80 mL/min) to afford the title compound (2.76 g, 9.68 mmol, 76% yield) as a pink solid. ¹H NMR (500 MHz, CDCl₃) δ 7.40-7.33 (m, 2H), 6.82-6.75 (m, 2H), 4.27 (dd, J=10.2, 6.1 Hz, 1H), 4.04 (dd, J=10.0, 8.7 Hz, 1H), 3.67 (s, 3H), 1.92 (td, J=8.3, 5.8 Hz, 1H), 1.79 (ddd, J=8.5, 7.2, 6.1 Hz, 1H), 1.25-1.16 (m, 2H).

Example 28

The title compound was prepared from (±)-methyl 2-((4-bromophenoxy) methyl)cyclopropanecarboxylate and 3-phenoxypiperidine by a procedure analogous to that used for the synthesis of Example 22. The title compound (16.4 mg, 0.045 mmol, 42.3% yield over 2 steps) was obtained as an oil. ¹H NMR (500 MHz, DMSO-d₆) δ 7.31 (t, J=8.0 Hz, 2H), 7.02 (d, J=8.0 Hz, 3H), 6.96 (t, J=7.3 Hz, 1H), 6.85 (d, J=7.4 Hz, 2H), 4.59 (br. s., 1H), 4.20 (dd, J=10.0, 5.1 Hz, 1H), 3.95 (t, J=9.2 Hz, 1H), 3.35 (br. s., 2H), 2.94 (br. s., 2H), 2.06 (br. s., 1H), 1.92 (br. s., 1H), 1.82-1.70 (m, 3H), 1.60 (br. s., 1H), 1.13 (td, J=8.2, 4.3 Hz, 1H), 0.98-0.89 (m, 1H).

Example 31

5-(4-(3-(4-Fluorophenoxy)azepan-1-yl)phenyl)pentanoic acid

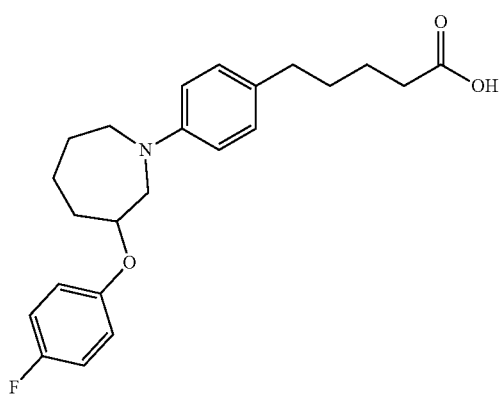 [SMILES: O=C(O)CCCCc1ccc(N2CCCCC(Oc3ccc(F)cc3)C2)cc1]

31A. 1-(Allylamino)pent-4-en-2-ol

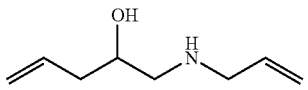

A mixture of 1-chloropent-4-en-2-ol (8.41 g, 69.7 mmol) and prop-2-en-1-amine (26.2 ml, 349 mmol) was heated at 87° C. overnight, then was cooled to rt and the excess prop-2-en-1-amine was evaporated. The residue was chromatographed (SiO₂; 120 g; A=DCM, B=10% MeOH/1% NH₄OH/DCM; 30 min gradient from 0% B to 100% B; flow rate=80 mL/min; fractions containing product were identified by TLC using PMA stain; TLC R$_f$=0.5, 10% MeOH/1% NH₄OH/DCM) to afford the title compound (4.22 g, 29.9 mmol, 42.8% yield) as a dark tan oil. ¹H NMR (400 MHz, CDCl₃) δ 6.02-5.78 (m, 2H), 5.32-5.09 (m, 4H), 3.88-3.85 (m, 1H), 3.45-3.32 (m, 2H), 2.82 (dd, J=12.3, 3.1 Hz, 1H), 2.61 (dd, J=12.2, 9.4 Hz, 1H), 2.32-2.22 (m, 2H).

31B. tert-Butyl allyl(2-hydroxypent-4-en-1-yl)carbamate

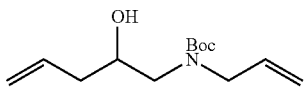 [SMILES: C=CCC(O)CN(CC=C)C(=O)OC(C)(C)C]

To a mixture of 1-(allylamino)pent-4-en-2-ol (4.22 g, 29.9 mmol) and TEA (5.00 ml, 35.9 mmol) in DCM (50 ml) was added Boc₂O (7.50 g, 34.4 mmol) and the reaction was stirred under Ar overnight at rt. Volatiles were removed in vacuo and the residue was chromatographed (SiO₂; 120 g; A=Hex, B=EtOAc; 30 min gradient from 0% B to 70% B; flow rate=80 mL/min; fractions containing product were identified by TLC using PMA stain; TLC R$_f$=0.5, 2:1 Hex: EtOAc) to afford the title compound (5.37 g, 22.3 mmol, 74.5% yield) as a pale yellow oil. ¹H NMR (500 MHz, CDCl₃) δ 5.91-5.76 (m, 2H), 5.20-5.09 (m, 4H), 3.98-3.80 (m, 3H), 3.49-3.20 (m, 2H), 2.31-2.18 (m, 2H), 1.48 (s, 9H).

31C. tert-Butyl 3-hydroxy-2,3,4,7-tetrahydro-1H-azepine-1-carboxylate

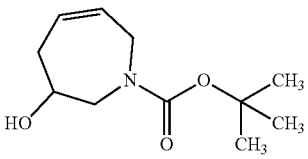

A solution of tert-butyl allyl(2-hydroxypent-4-en-1-yl) carbamate (3.0 g, 12.4 mmol) in DCM (100 ml) was purged with Ar (2×), after which Grubbs II catalyst (1.06 g, 1.24 mmol) was added and the reaction was purged with Ar again (2×). The reaction mixture was heated at reflux under Ar overnight, then cooled to rt and concentrated in vacuo. The residue was chromatographed (SiO₂; 80 g; A=Hex, B=EtOAc; 15 min gradient from 0% B to 100% B; flow rate=60 mL/min; fractions containing product were identified by TLC using PMA stain; TLC R$_f$=0.5, 4:1 Hex:EtOAc) to afford the title compound (1.39 g, 6.52 mmol, 52.4% yield) as a dark tan oil. ¹H NMR (500 MHz, CDCl₃) δ 6.66-6.43 (m, 1H), 5.07-4.90 (m, 1H), 4.14-4.07 (m, 1H), 3.84-3.70 (m, 2H), 2.57-2.45 (m, 1H), 2.35-2.23 (m, 1H), 2.14-2.04 (m, 2H), 1.77 (d, J=1.7 Hz, 1H), 1.50 (s, 9H).

31D. tert-Butyl 3-hydroxyazepane-1-carboxylate

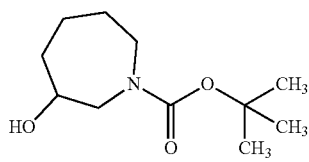

A solution of tert-butyl 3-hydroxy-2,3,4,7-tetrahydro-1H-azepine-1-carboxylate (0.55 g, 2.58 mmol) in MeOH (20 mL) was purged with Ar, after which Pd—C (0.274 g, 0.258 mmol) was added and the reaction was purged again with Ar, then stirred under an atmosphere of H₂ for 3 h. The catalyst was filtered off and the filtrate was concentrated in vacuo to afford the title compound (0.55 g, 2.55 mmol, 99% yield) as a pale yellow oil. ¹H NMR (400 MHz, CDCl₃) δ 4.00-3.91 (m, 1H), 3.83-3.75 (m, 1H), 3.74-3.64 (m, 1H), 3.48-3.25 (m, 2H), 3.08-2.97 (m, 1H), 1.88 (d, J=9.2 Hz, 1H), 1.81-1.65 (m, 3H), 1.61-1.51 (m, 1H), 1.49 (s, 9H), 1.44-1.32 (m, 1H).

31E. 3-(4-Fluorophenoxy)azepane

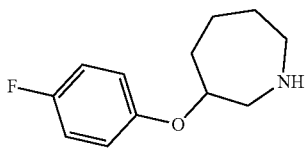

A mixture of tert-butyl 3-hydroxyazepane-1-carboxylate (0.5 g, 2.32 mmol) and Ph₃P (1.52 g, 5.81 mmol) in toluene (100 mL) was heated to 100° C. and stirred for 30 min at 100° C., after which a solution of 4-fluorophenol (0.521 g, 4.64 mmol) and DIAD (2.26 mL, 11.6 mmol) in toluene (20 mL) was added over 1 h via syringe pump at this temperature. The reaction mixture was stirred for 4 h at 100° C., then was cooled to rt and volatiles were removed in vacuo. The residue was chromatographed (SiO₂; 80 g; A=Hex, B=EtOAc; 60 min gradient from 0% B to 70% B; flow rate=60 mL/min) to give the desired phenyl-azepane product.

A solution of the phenyl-azepane product in DCM (5 mL) and TFA (5 mL) was stirred at rt for 2 h, then was concentrated in vacuo. The residue was dissolved in aq. 1 N HCl (30 mL) and washed with EtOAc (3×15 mL). The aqueous phase was then neutralized with solid Na₂CO₃, saturated with solid NaCl and extracted with 10% IPA/CHCl₃ (3×15 mL), and EtOAc (3×15 mL). The combined organic extracts were dried (Na₂SO₄), and concentrated in vacuo to provide the title compound (20 mg, 0.096 mmol, 4.1% yield) as a tan oil. LCMS [M+1]⁺=210.

Example 31

The title compound was prepared from 3-(4-fluorophenoxy)azepane and methyl 5-(4-bromophenyl)pentanoate by a procedure analogous to the one used for the synthesis of Example 22. The title compound (7.7 mg, 0.019 mmol, 12.9% yield over 2 steps) was obtained as a tan oil. ¹H NMR (400 MHz, CD₂Cl₂) δ 6.94-6.87 (m, 4H), 6.82-6.78 (m, 2H), 6.59 (br. s., 2H), 4.47 (br. s., 1H), 3.85 (d, J=12.5 Hz, 1H), 3.50 (br. s., 1H), 3.32 (br. s., 2H), 2.42 (br. s., 2H), 1.87-1.74 (m, 3H), 1.74-1.60 (m, 3H), 1.59-1.45 (m, 5H), 1.40-1.30 (m, 1H).

Example 32

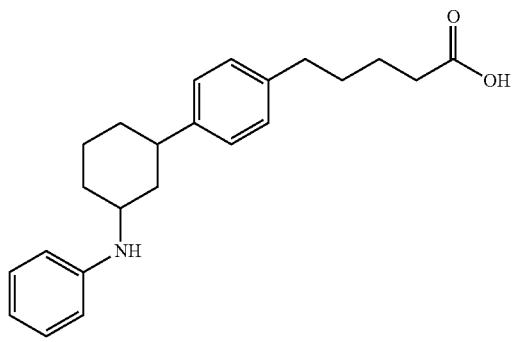 [SMILES: O=C(O)CCCCc1ccc(C2CCCC(Nc3ccccc3)C2)cc1]

Step 1: To a mixture of methyl 5-(4-(3-oxocyclohexyl)phenyl)pentanoate 1E (40 mg, 0.139 mmol), aniline (52 mg, 0.56 mmol) and MeOH (1.85 mL) was added NaBH(OAc)₃ (58.8 mg, 0.277 mmol) and the reaction was stirred at rt under Ar overnight. The reaction was then diluted with 10% aq. citric acid (10 mL) and extracted with EtOAc (2×5 mL). The combined organic extracts were washed with brine, dried (Na₂SO₄) and concentrated in vacuo to yield the desired cyclohexyl aniline product (50.2 mg, 0.137 mmol, 99% yield) as a pale yellow oil. LCMS [M+1]⁺=366.

A mixture of the cyclohexyl aniline product (50.2 mg, 0.137 mmol) in KOH (0.5 mL of a 2 N solution in MeOH) and water (1 drop) was stirred at rt for 2 h, after which volatiles were removed in vacuo. The residue was purified by preparative HPLC (Method: Gradient Solv. System: From 80% A:20% B to 0% A:100% B; (A=10% MeCN/90% H₂O+0.1% TFA); (B=90% MeCN/10% H₂O+0.1% TFA); Detection at 220 nm; 10 min gradient; PHENOMENEX® Axia 5μ C18, 30×100 mm) to afford the title compound (19.8 mg, 0.054 mmol, 39.4% yield) as a light tan solid. ¹H NMR (500 MHz, CDCl₃) δ 7.44-7.38 (m, 2H), 7.37-7.30 (m, 3H), 7.08-7.03 (m, 4H), 3.75-3.66 (m, 1H), 3.13-3.04 (m, 1H), 2.58 (t, J=6.9 Hz, 2H), 2.40-2.32 (m, 2H), 2.07-1.94 (m, 2H), 1.89-1.74 (m, 3H), 1.71-1.60 (m, 6H), 1.55 (dd, J=7.2, 3.6 Hz, 1H).

The following Examples were prepared according to the methods previously described above.

| Ex. No. | Structure and Name | $^1$H NMR | Method |
|---|---|---|---|
| 34 | 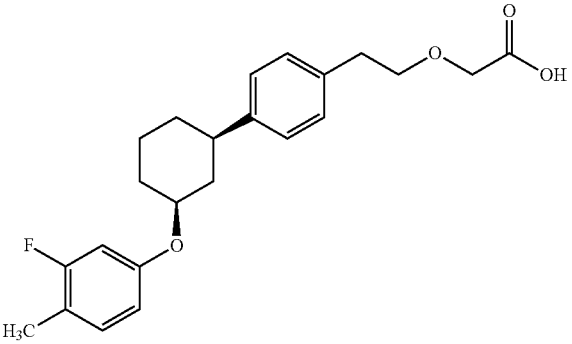<br>2-(4-((+/−)-3-(3-fluoro-4-methylphenoxy)cyclohexyl)phenethoxy)acetic acid | $^1$H NMR (500 MHz, DMSO-d$_6$) δ 7.20-7.07 (m, 5H), 6.76 (d, J = 12.2 Hz, 1H), 6.68 (d, J = 6.4 Hz, 1H), 4.37 (t, J = 10.5 Hz, 1H), 3.95 (s, 2H), 3.62 (t, J = 6.9 Hz, 1H), 2.76 (t, J = 6.7 Hz, 2H), 2.67 (t, J = 12.1 Hz, 1H), 2.54-2.50 (m, 1H), 2.11 (s, 5H), 1.83 (d, J = 13.4 Hz, 1H), 1.72 (d, J = 11.9 Hz, 1H), 1.56-1.40 (m, 2H), 1.39-1.24 (m, 2H) | Ex. 4 (Method A) |
| 35 | 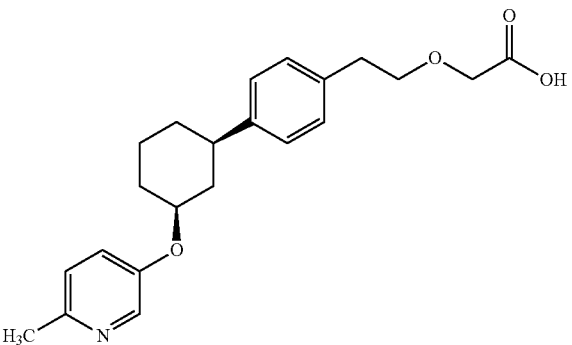<br>2-(4-((+/−)-3-((6-methylpyridin-3-yl)oxy)cyclohexyl)phenethoxy)acetic acid | $^1$H NMR (500 MHz, DMSO-d$_6$) δ 8.36 (br. s., 1H), 7.84 (d, J = 6.7 Hz, 1H), 7.54 (d, J = 8.8 Hz, 1H), 7.15 (s, 4H), 4.57 (t, J = 10.5 Hz, 1H), 3.97 (s, 2H), 3.61 (br. s., 1H), 2.81-2.61 (m, 4H), 2.56-2.52 (m, 3H), 2.13 (t, J = 11.0 Hz, 2H), 1.87 (d, J = 14.3 Hz, 1H), 1.74 (d, J = 12.5 Hz, 1H), 1.59-1.45 (m, 2H), 1.43-1.30 (m, 2H) | Ex. 4 (Method A) |
| 36 | 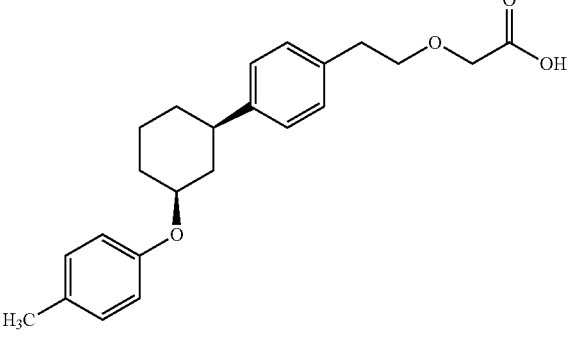<br>2-(4-((+/−)-3-(p-tolyloxy)cyclohexyl)phenethoxy)acetic acid | $^1$H NMR (500 MHz, DMSO-d$_6$) δ 7.14 (s, 4H), 7.04 (d, J = 8.2 Hz, 2H), 6.82 (d, J = 8.2 Hz, 2H), 4.32 (t, J = 10.7 Hz, 1H), 3.95 (s, 2H), 3.62 (t, J = 6.7 Hz, 1H), 2.76 (t, J = 6.7 Hz, 2H), 2.65 (t, J = 12.2 Hz, 1H), 2.50 (br. s., 1H), 2.19 (s, 3H), 2.14-2.02 (m, 2H), 1.83 (d, J = 13.4 Hz, 1H), 1.72 (d, J = 12.2 Hz, 1H), 1.55-1.39 (m, 2H), 1.37-1.21 (m, 2H) | Ex. 4 (Method B) |
| 37 | 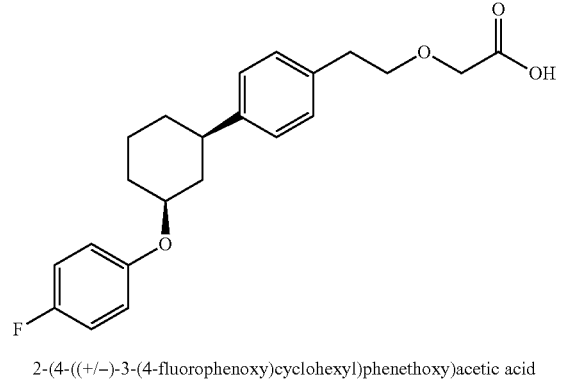 [SMILES: O=C(O)COCCc1ccc([C@@H]2CCC[C@H](Oc3ccc(F)cc3)C2)cc1]<br>2-(4-((+/−)-3-(4-fluorophenoxy)cyclohexyl)phenethoxy)acetic acid | $^1$H NMR (500 MHz, DMSO-d$_6$) δ 7.14 (s, 4H), 7.10-7.03 (m, 2H), 6.95 (dd, J = 9.0, 4.4 Hz, 2H), 4.40-4.25 (m, 1H), 3.95 (s, 2H), 3.62 (t, J = 7.0 Hz, 1H), 2.76 (t, J = 6.9 Hz, 2H), 2.65 (t, J = 12.4 Hz, 1H), 2.52 (br. s., 1H), 2.10 (t, J = 11.1 Hz, 2H), 1.84 (d, J = 13.4 Hz, 1H), 1.73 (d, J = 12.2 Hz, 1H), 1.55-1.40 (m, 2H), 1.40-1.26 (m, 2H) | Ex. 4 (Method B) |

-continued

| Ex. No. | Structure and Name | ¹H NMR | Method |
|---|---|---|---|
| 38 | 2-(4-((+/−)-3-(4-chlorophenoxy)cyclohexyl)phenethoxy)acetic acid | ¹H NMR (500 MHz, DMSO-d₆) δ 7.35 (d, J = 8.9 Hz, 2H), 7.22 (s, 4H), 7.04 (d, J = 8.5 Hz, 2H), 4.54-4.41 (m, 1H), 4.02 (s, 2H), 3.70 (t, J = 6.6 Hz, 1H), 2.84 (t, J = 6.7 Hz, 2H), 2.75 (t, J = 12.2 Hz, 1H), 2.63-2.58 (m, 1H), 2.26-2.09 (m, 2H), 1.92 (d, J = 13.1 Hz, 1H), 1.81 (d, J = 12.8 Hz, 1H), 1.63-1.49 (m, 2H), 1.48-1.33 (m, 2H) | Ex. 4 (Method B) |
| 39 | 2-(4-((+/−)-3-(4-cyanophenoxy)cyclohexyl)phenethoxy)acetic acid | ¹H NMR (500 MHz, DMSO-d₆) δ 7.68 (d, J = 8.9 Hz, 2H), 7.17-7.04 (m, 6H), 4.63-4.47 (m, 1H), 3.95 (s, 1H), 3.77 (s, 2H), 3.61 (t, J = 6.9 Hz, 1H), 2.81-2.64 (m, 3H), 2.10 (br. s., 2H), 1.84 (d, J = 12.8 Hz, 1H), 1.72 (d, J = 11.9 Hz, 1H), 1.60-1.45 (m, 2H), 1.42-1.27 (m, 2H) | Ex. 4 (Method B) |
| 40 | (1S,2S)-2-(4-((±)-3-phenoxycyclohexyl)phenethyl)cyclopropanecarboxylic acid | ¹H NMR (500 MHz, DMSO-d₆) δ 7.33-7.25 (m, 2H), 7.16-7.06 (m, 4H), 6.99 (dd, J = 8.7, 1.0 Hz, 2H), 6.94-6.87 (m, 1H), 4.76 (br, s., 1H), 2.97-2.87 (m, 1H), 2.64-2.56 (m, 2H), 2.06-1.91 (m, 2H), 1.85-1.68 (m, 3H), 1.64-1.42 (m, 5H), 1.36-1.27 (m, 1H), 1.19 (ddd, J = 8.7, 6.5, 4.0 Hz, 1H), 0.94 (dt, J = 8.6, 4.1 Hz, 1H), 0.70 (ddd, J = 8.0, 6.3, 3.9 Hz, 1H). | Ex. 7 |
| 41 | (1R,2R)-2-(4-((±)-3-phenoxycyclohexyl)phenethyl)cyclopropanecarboxylic acid | ¹H NMR (500 MHz, DMSO-d₆) δ 7.28 (dd, J = 8.5, 7.4 Hz, 2H), 7.10 (d, J = 1.9 Hz, 4H), 6.99 (d, J = 7.7 Hz, 2H), 6.91 (s, 1H), 4.76 (br. s., 1H), 2.97-2.87 (m, 1H), 2.64-2.57 (m, 2H), 2.07-1.91 (m, 2H), 1.73 (s, 3H), 1.64-1.41 (m, 5H), 1.36-1.28 (m, 1H), 1.24-1.12 (m, 1H), 0.93 (s, 1H), 0.74-0.64 (m, 1H). | Ex. 10 |

| Ex. No. | Structure and Name | ¹H NMR | Method |
|---|---|---|---|
| 42 | 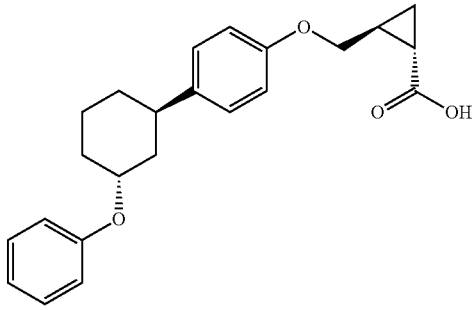<br>(1S,2S)-2-(4-((±)-3-phenoxycyclo-hexyl)phenoxy)methyl)cyclopropanecarboxylic acid | ¹H NMR (500 MHz, DMSO-d$_6$) δ 7.29 (t, J = 7.8 Hz, 2H), 7.12 (d, J = 8.5 Hz, 2H), 7.00 (d, J = 8.3 Hz, 2H), 6.92 (t, J = 7.3 Hz, 1H), 6.84 (d, J = 8.5 Hz, 2H), 4.77 (br. s., 1H), 3.94 (dd, J = 10.5, 6.3 Hz, 1H), 3.79 (dd, J = 10.5, 7.4 Hz, 1H), 2.95-2.86 (m, 1H), 2.06-1.92 (m, 2H), 1.84-1.65 (m, 4H), 1.63-1.52 (m, 3H), 1.46 (dd, J = 12.2, 2.9 Hz, 1H), 1.07 (dt, J = 8.7, 4.3 Hz, 1H), 0.99-0.90 (m, 1H). | Ex. 11 |
| 43 | 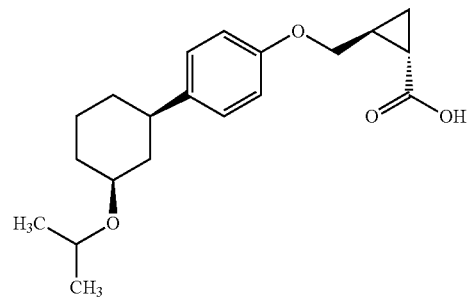<br>(1S,2S)-2-(4-((±)-3-isopropoxycyclo-hexyl)phenoxy)methyl)cyclopropanecarboxylic acid | ¹H NMR (500 MHz, DMSO-d$_6$) δ 7.13 (d, J = 8.3 Hz, 2H), 6.84 (d, J = 8.5 Hz, 2H), 3.95 (dd, J = 10.5, 6.3 Hz, 1H), 3.80 (dd, J = 10.2, 7.4 Hz, 1H), 3.72 (dt, J = 12.1, 6.1 Hz, 1H), 3.45-3.39 (m, 1H), 2.48 (d, J = 3.3 Hz, 1H), 2.04-1.89 (m, 2H), 1.82-1.74 (m, 1H), 1.73-1.64 (m, 2H), 1.59 (dt, J = 8.4, 4.3 Hz, 1H), 1.43-1.32 (m, 1H), 1.30-1.19 (m, 2H), 1.12 (d, J = 14.6 Hz, 1H), 1.07 (t, J = 6.6 Hz, 7H), 0.98-0.91 (m, 1H). | Ex. 3 |
| 44 | 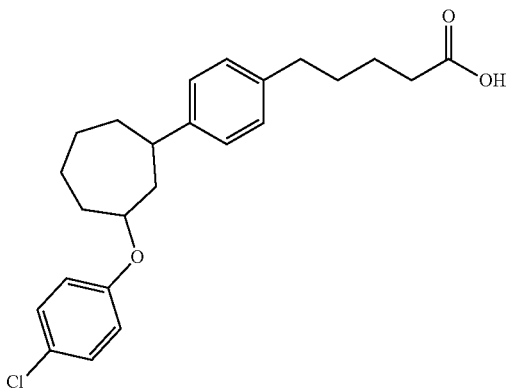<br>± 5-(4-(3-(4-chlorophenoxy)cycloheptyl)phenyl)pentanoic acid (diastereomer 1) | ¹H NMR (500 MHz, DMSO-d$_6$) δ 7.35-7.23 (m, 2H), 7.18-7.03 (m, 4H), 6.96-6.84 (m, 2H), 4.64-4.52 (m, 1H), 2.86-2.72 (m, 1H), 2.57-2.44 (m, 2H), 2.21 (t, J = 7.2 Hz, 2H), 2.11-2.01 (m, 2H), 1.97-1.89 (m, 1H), 1.85-1.72 (m, 3H), 1.72-1.62 (m, 3H), 1.61-1.44 (m, 5H) | Ex. 12 |

| Ex. No. | Structure and Name | ¹H NMR | Method |
|---|---|---|---|
| 45 | 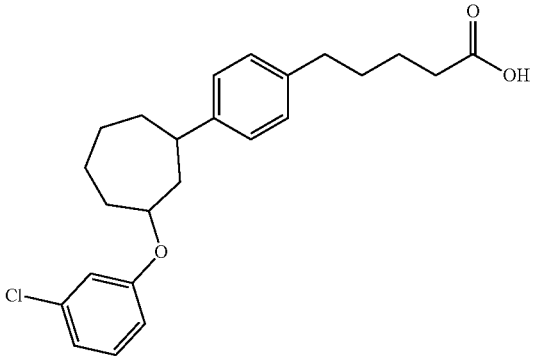<br>± 5-(4-(3-(3-chlorophenoxy)cycloheptyl)phenyl)pentanoic acid (diastereomer 1) | ¹H NMR (500 MHz, DMSO-d$_6$) δ 7.20 (t, J = 8.1 Hz, 1H), 7.08-6.98 (m, 4H), 6.91-6.84 (m, 2H), 6.83-6.77 (m, 1H), 4.61-4.53 (m, 1H), 2.76-2.67 (m, 1H), 2.48-2.40 (m, 2H), 2.14 (t, J = 7.0 Hz, 2H), 2.03-1.92 (m, 2H), 1.92-1.83 (m, 1H), 1.79-1.66 (m, 3H), 1.65-1.55 (m, 3H), 1.54-1.38 (m, 5H) | Ex. 12 |
| 46 | 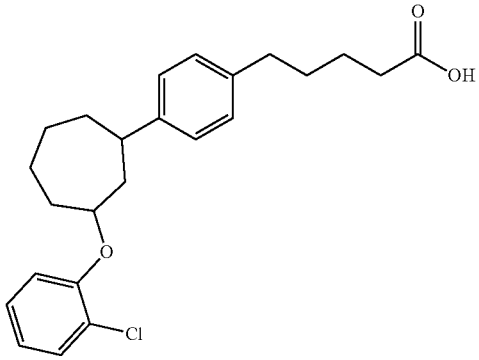<br>± 5-(4-(3-(2-chlorophenoxy)cycloheptyl)phenyl)pentanoic acid (diastereomer 1) | ¹H NMR (500 MHz, DMSO-d$_6$) δ 7.42-7.37 (m, 1H), 7.26 (ddd, J = 8.3, 7.4, 1.7 Hz, 1H), 7.17-7.03 (m, 5H), 6.95-6.87 (m, 1H), 4.70-4.62 (m, 1H), 2.82-2.74 (m, 1H), 2.56-2.48 (m, 2H), 2.21 (t, J = 7.2 Hz, 2H), 2.12-1.95 (m, 3H), 1.90-1.63 (m, 6H), 1.62-1.43 (m, 5H) | Ex. 12 |
| 47 | 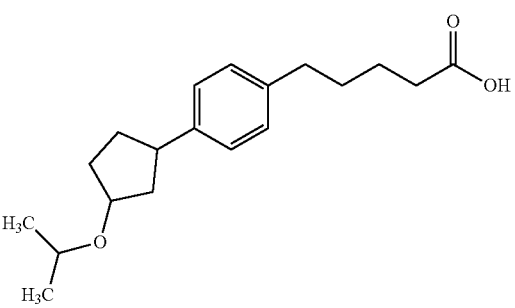<br>± 5-(4-(3-isopropoxycyclopentyl)phenyl)pentanoic acid (diastereomeric mixture) | ¹H NMR (500 MHz, DMSO-d$_6$) δ 7.19-7.13 (m, 2H), 7.10 (d, J = 7.7 Hz, 2H), 4.17-4.05 (m, 1H), 3.66-3.58 (m, 1H), 3.15 (ddd, J = 17.6, 10.0, 7.8 Hz, 1H), 2.99-2.89 (m, 1H), 2.57-2.54 (m, 1H), 2.31 (dt, J = 13.2, 6.9 Hz, 1H), 2.21 (t, J = 7.2 Hz, 2H), 2.10-2.02 (m, 1H), 2.00-1.89 (m, 1H), 1.86-1.77 (m, 1H), 1.74-1.44 (m, 6H), 1.12-1.06 (m, 6H) | Ex. 3 |

| Ex. No. | Structure and Name | ¹H NMR | Method |
|---|---|---|---|
| 48 | 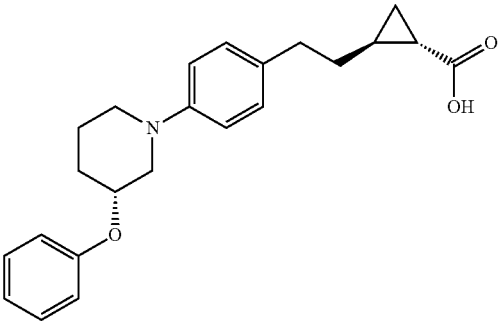<br>(1S,2S)-2-(4-((R)-3-phenoxypiperidin-1-yl)phenethyl)cyclopropanecarboxylic acid | ¹H NMR (500 MHz, CDCl$_3$) δ 7.42 (d, J = 6.3 Hz, 2H), 7.33-7.29 (m, 2H), 7.23 (d, J = 8.5 Hz, 2H), 7.04-7.01 (m, 2H), 6.98 (t, J = 7.4 Hz, 1H), 5.08 (br. s., 1H), 3.85 (dd, J = 11.6, 3.9 Hz, 1H), 3.61 (d, J = 12.1 Hz, 1H), 3.12-3.05 (m, 2H), 2.80-2.68 (m, 2H), 2.37 (d, J = 10.2 Hz, 2H), 2.10-2.03 (m, 1H), 1.78-1.64 (m, 2H), 1.51 (dd, J = 14.0, 7.4 Hz, 1H), 1.43-1.34 (m, 1H), 1.22 (ddt, J = 17.3, 8.5, 4.4 Hz, 2H), 0.75 (ddd, J = 7.8, 6.6, 4.0 Hz, 1H) | Ex. 22 |
| 49 | 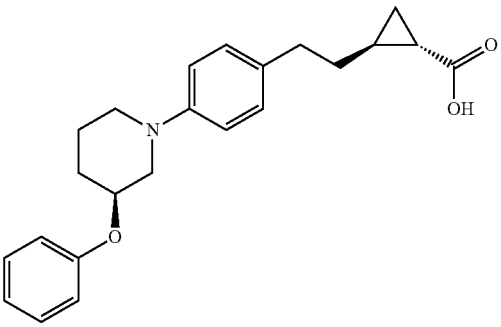<br>(1S,2S)-2-(4-((S)-3-phenoxypiperidin-1-yl)phenethyl)cyclopropanecarboxylic acid | ¹H NMR (500 MHz, CDCl$_3$) δ 7.49-7.43 (m, 2H), 7.35-7.27 (m, 4H), 7.06-6.96 (m, 3H), 5.03-4.93 (m, 1H), 3.90 (dd, J = 11.8, 3.9 Hz, 1H), 3.71 (d, J = 11.8 Hz, 1H), 3.31-3.19 (m, 2H), 2.86-2.70 (m, 2H), 2.42-2.33 (m, 1H), 2.30-2.13 (m, 2H), 1.85-1.70 (m, 2H), 1.52-1.43 (m, 1H), 1.40-1.33 (m, 1H), 1.24-1.15 (m, 2H), 0.80-0.70 (m, 1H) | Ex. 22 |
| 50 | 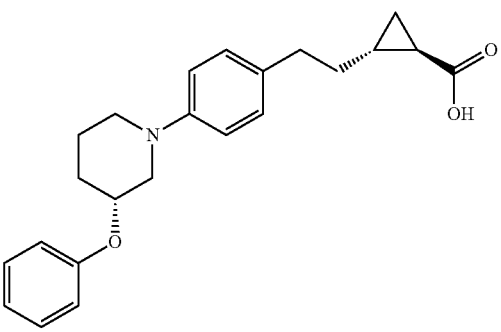<br>(1R,2R)-2-(4-((R)-3-phenoxypiperidin-1-yl)phenethyl)cyclopropanecarboxylic acid | ¹H NMR (400 MHz, CDCl$_3$) δ 7.49 (d, J = 8.6 Hz, 2H), 7.34-7.30 (m, 4H), 7.05-6.99 (m, 3H), 5.04-4.95 (m, 1H), 3.91 (dd, J = 11.6, 3.9 Hz, 1H), 3.74 (d, J = 12.1 Hz, 1H), 3.38-3.23 (m, 2H), 2.88-2.71 (m, 2H), 2.37 (d, J = 12.8 Hz, 1H), 2.32-2.14 (m, 2H), 1.89-1.72 (m, 2H), 1.47 (dd, J = 13.8, 7.8 Hz, 1H), 1.42-1.32 (m, 1H), 1.24-1.14 (m, 2H), 0.76 (ddd, J = 7.8, 6.4, 4.1 Hz, 1H) | Ex. 22 |
| 51 | 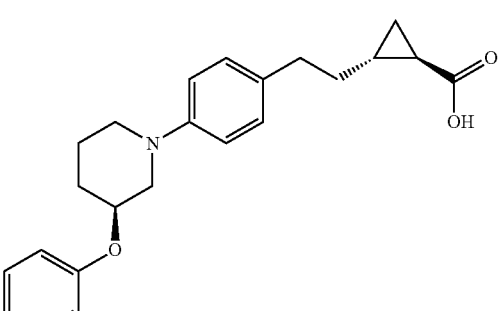<br>(1R,2R)-2-(4-((S)-3-phenoxypiperidin-1-yl)phenethyl)-cyclopropanecarboxylic acid | ¹H NMR (400 MHz, CDCl$_3$) δ 7.45 (d, J = 8.6 Hz, 2H), 7.35-7.28 (m, 4H), 7.04-6.98 (m, 3H), 5.01-4.92 (m, 1H), 3.92 (dd, J = 11.6, 3.9 Hz, 1H), 3.70 (d, J = 12.1 Hz, 1H), 3.31-3.18 (m, 2H), 2.87-2.69 (m, 2H), 2.41-2.32 (m, 1H), 2.31-2.11 (m, 2H), 1.84-1.69 (m, 2H), 1.53-1.41 (m, 1H), 1.41-1.32 (m, 1H), 1.24-1.12 (m, 2H), 0.79-0.71 (m, 1H) | Ex. 22 |

| Ex. No. | Structure and Name | ¹H NMR | Method |
|---|---|---|---|
| 52 | (1R,2R)-2-(4-((S)-3-(4-fluorophenoxy)piperidin-1-yl)phenethyl)cyclopropanecarboxylic acid | ¹H NMR (500 MHz, CD₃OD) δ 7.07 (d, J = 8.4 Hz, 2H), 6.97 (d, J = 1.9 Hz, 2H), 6.93 (d, J = 4.5 Hz, 2H), 6.88 (d, J = 8.4 Hz, 2H), 4.44-4.37 (m, 1H), 4.37-4.28 (m, 1H), 3.62-3.56 (m, 1H), 2.89 (s, 2H), 2.64 (d, J = 7.4 Hz, 2H), 2.14-2.07 (m, 1H), 1.99-1.91 (m, 1H), 1.81-1.71 (m, 1H), 1.57 (d, J = 8.4 Hz, 3H), 1.38-1.27 (m, 2H), 1.14-1.07 (m, 1H), 0.73-0.65 (m, 1H) | Ex. 22 |
| 53 | (1S,2S)-2-(4-((S)-3-phenylpiperidin-1-yl)phenethyl)cyclopropanecarboxylic acid | ¹H NMR (500 MHz, DMSO-d₆) δ 7.34 (d, J = 4.4 Hz, 4H), 7.28-7.23 (m, 1H), 7.20-7.04 (m, 4H), 3.71-3.60 (m, 3H), 3.01-2.91 (m, 2H), 2.62-2.57 (m, 2H), 1.98-1.75 (m, 3H), 1.73-1.65 (m, 1H), 1.57-1.49 (m, 2H), 1.34-1.28 (m, 1H), 1.22-1.15 (m, 1H), 0.96-0.91 (m, 1H), 0.75-0.68 (m, 1H) | Ex. 22 |
| 54 | (1S,2S)-2-(4-((R)-3-phenylpiperidin-1-yl)phenethyl)cyclopropanecarboxylic acid | ¹H NMR (500 MHz, DMSO-d₆) δ 7.34 (d, J = 4.4 Hz, 4H), 7.27-7.22 (m, 1H), 7.16-7.09 (m, 2H), 7.08-6.99 (m, 2H), 3.70-3.61 (m, 3H), 2.97-2.91 (m, 2H), 2.62-2.56 (m, 2H), 1.96-1.84 (m, 2H), 1.81-1.73 (m, 1H), 1.72-1.63 (m, 1H), 1.56-1.48 (m, 2H), 1.34-1.28 (m, 1H), 1.23-1.14 (m, 1H), 0.97-0.91 (m, 1H), 0.74-0.67 (m, 1H) | Ex. 22 |
| 55 | (1R,2R)-2-(4-((S)-3-phenylpiperidin-1-yl)phenethyl)cyclopropanecarboxylic acid | ¹H NMR (500 MHz, DMSO-d₆) δ 7.38-7.32 (m, 4H), 7.28-7.22 (m, 1H), 7.21-7.05 (m, 4H), 3.69-3.61 (m, 3H), 2.99 (br. s, 2H), 2.61 (t, J = 7.4 Hz, 2H), 1.98-1.79 (m, 3H), 1.76-1.66 (m, 1H), 1.54 (q, J = 7.2 Hz, 2H), 1.32 (dt, J = 8.0, 4.3 Hz, 1H), 1.23-1.15 (m, 1H), 0.94 (dt, J = 8.6, 4.1 Hz, 1H), 0.75-0.68 (m, 1H) | Ex. 22 |

| Ex. No. | Structure and Name | ¹H NMR | Method |
|---|---|---|---|
| 56 | 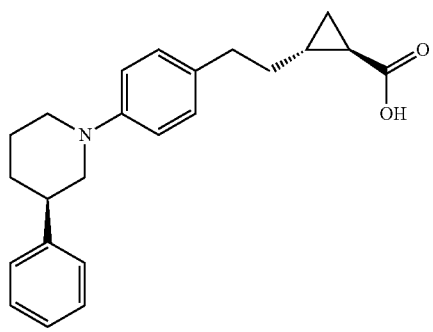<br>(1R,2R)-2-(4-((R)-3-phenylpiperidin-1-yl)phenethyl)cyclopropanecarboxylic acid | ¹H NMR (500 MHz, DMSO-$d_6$) δ 7.34 (d, J = 4.4 Hz, 4H), 7.27-7.23 (m, 1H), 7.19-7.09 (m, 4H), 3.69-3.60 (m, 3H), 3.02-2.93 (m, 2H), 2.63-2.59 (m, 2H), 1.98-1.76 (m, 3H), 1.75-1.65 (m, 1H), 1.54 (d, J = 7.7 Hz, 2H), 1.35-1.28 (m, 1H), 1.24-1.15 (m, 1H), 0.96-0.91 (m, 1H), 0.75-0.68 (m, 1H) | Ex. 22 |
| 57 | 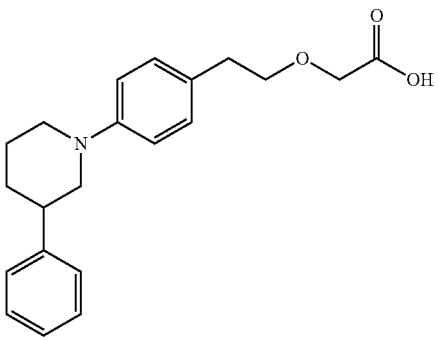<br>± 2-(4-(3-phenylpiperidin-1-yl)phenethoxy)acetic acid | ¹H NMR (400 MHz, $CD_2Cl_2$) δ 7.42 (d, J = 8.6 Hz, 2H), 7.32-7.24 (m, 4H), 7.22-7.15 (m, 3H), 4.02-3.92 (m, 2H), 3.67 (t, J = 6.3 Hz, 3H), 3.46-3.37 (m, 1H), 3.27-3.09 (m, 2H), 2.84 (t, J = 6.3 Hz, 2H), 2.32-2.17 (m, 1H), 2.12-2.02 (m, 2H), 1.80-1.65 (m, 1H), 1.24-1.11 (m, 1H) | Ex. 21 |
| 58 | 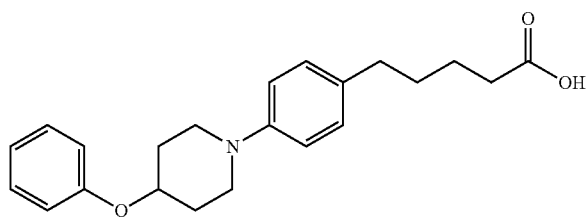<br>5-(4-(4-phenoxypiperidin-1-yl)phenyl)pentanoic acid | ¹H NMR (500 MHz, DMSO-$d_6$) δ 7.34-7.27 (m, 2H), 7.12 (d, J = 6.3 Hz, 2H), 7.08-6.97 (m, 4H), 6.94 (t, J = 7.4 Hz, 1H), 4.59 (br. s., 1H), 3.53-3.46 (m, 4H), 3.19-3.06 (m, 2H), 2.23 (t, J = 7.2 Hz, 2H), 2.09 (br. s., 2H), 1.81 (br. s., 2H), 1.61-1.46 (m, 4H) | Ex. 22 |
| 59 | 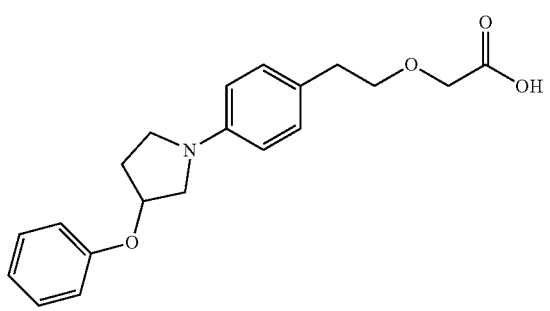<br>± 2-(4-(3-phenoxypyrrolidin-1-yl)phenethoxy)acetic acid | ¹H NMR (400 MHz, $CD_2Cl_2$) δ 7.43-7.28 (m, 6H), 7.10-7.03 (m, 1H), 6.99 (dd, J = 8.7, 0.9 Hz, 2H), 5.23 (br. s., 1H), 4.30 (dd, J = 12.4, 4.5 Hz, 1H), 4.11 (s, 2H), 4.00-3.91 (m, 1H), 3.80 (t, J = 6.7 Hz, 2H), 3.72 (t, J = 13.3 Hz, 2H), 2.96 (t, J = 6.4 Hz, 2H), 2.57-2.46 (m, 2H) | Ex. 21 |

| Ex. No. | Structure and Name | ¹H NMR | Method |
|---|---|---|---|
| 60 | (S)-5-(4-(3-phenoxypyrrolidin-1-yl)phenyl)pentanoic acid | ¹H NMR (500 MHz, DMSO-d₆) δ 7.30 (s, 2H), 6.98 (dd, J = 14.4, 8.7 Hz, 5H), 6.50 (d, J = 8.3 Hz, 2H), 5.18-5.12 (m, 1H), 3.68-3.61 (m, 1H), 3.33-3.20 (m, 3H), 2.46 (s, 2H), 2.37-2.27 (m, 1H), 2.19 (s, 3H), 1.56-1.44 (m, 4H) | Ex. 22 |
| 61 | (R)-5-(4-(3-phenoxypyrrolidin-1-yl)phenyl)pentanoic acid | ¹H NMR (500 MHz, DMSO-d₆) δ 7.34-7.28 (m, 2H), 7.02-6.92 (m, 5H), 6.53-6.47 (m, 2H), 5.18-5.12 (m, 1H), 3.69-3.61 (m, 1H), 3.39-3.35 (m, 3H), 2.48-2.43 (m, 2H), 2.37-2.27 (m, 1H), 2.25-2.12 (m, 3H), 1.58-1.42 (m, 4H) | Ex. 22 |
| 62 | (1R,2R)-2-(4-(4-phenoxyazepan-1-yl)phenethyl)cyclopropanecarboxylic acid | ¹H NMR (500 MHz, DMSO-d₆) δ 7.26 (t, J = 7.7 Hz, 2H), 6.99 (d, J = 8.4 Hz, 2H), 6.92-6.85 (m, 3H), 6.63 (d, J = 8.4 Hz, 2H), 4.49 (br. s., 1H), 3.57-3.47 (m, 4H), 2.54 (br. s., 2H), 2.15-2.07 (m, 1H), 1.95-1.85 (m, 2H), 1.84-1.68 (m, 3H), 1.55-1.45 (m, 2H), 1.35-1.27 (m, 1H), 1.22-1.14 (m, 1H), 0.93 (dt, J = 8.7, 4.1 Hz, 1H), 0.69 (t, J = 8.7 Hz, 1H) | Ex. 22 |
| 63 | 2-(4-(3-phenoxyazetidin-1-yl)phenethoxy)acetic acid | ¹H NMR (500 MHz, CD₃OD) δ 7.22-7.15 (m, 2H), 7.03-6.99 (m, 2H), 6.89-6.83 (m, 1H), 6.76-6.72 (m, 2H), 6.46-6.40 (m, 2H), 4.98 (tt, J = 6.1, 4.3 Hz, 1H), 4.22 (dd, J = 9.1, 6.1 Hz, 2H), 3.96-3.94 (m, 2H), 3.71 (dd, J = 8.9, 4.3 Hz, 2H), 3.57 (t, J = 7.2 Hz, 2H), 2.71 (t, J = 7.2 Hz, 2H) | Ex. 21 |

What is claimed is:

1. A compound of Formula (II):

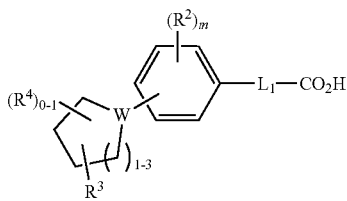

or a stereoisomer, a tautomer, a pharmaceutically acceptable salt, a polymorph, or a solvate thereof, wherein:

$L_1$ is independently selected from: $(CH_2)_{3-4}$, $(CH_2)_{2-3}OCH_2$,

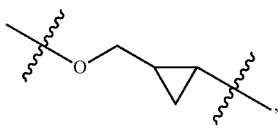 [SMILES: *OCC1CC1*]

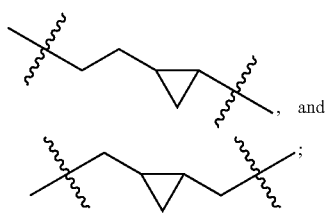

W is independently selected from: CH and N;

$R^2$, at each occurrence, is independently selected from: halogen, $C_{1-4}$ alkyl, and $C_{1-4}$ alkoxy;

$R^3$ is independently selected from: $C_{1-4}$ haloalkoxy, Bn, and $-(O)_{0-1}-R^5$;

$R^4$, at each occurrence, is independently selected from: halogen, and $C_{1-4}$ alkyl;

$R^5$ is independently selected from: phenyl, tetrahydropyranyl, oxadiazolyl, thiazolyl, pyridyl, and pyridazinyl; wherein each moiety is substituted with 0-2 $R^c$;

$R^c$, at each occurrence, is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $CO_2(C_{1-4}$ alkyl), and COPh; and m is independently 0, 1, or 2.

2. A compound according to claim 1, wherein the compound is of Formula (III)

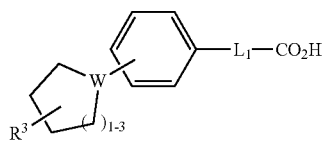

or a stereoisomer, a tautomer, a pharmaceutically acceptable salt, a polymorph, or a solvate thereof.

3. A compound according to claim 2 or a stereoisomer, a tautomer, a pharmaceutically acceptable salt, a polymorph, or a solvate thereof, wherein:

$L_1$ is independently selected from: $(CH_2)_{3-4}$, $(CH_2)_{2-3}OCH_2$,

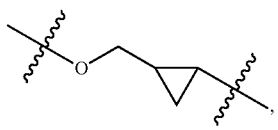

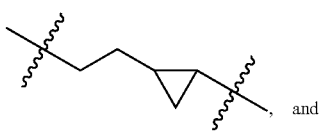

and

$R^3$ is independently selected from: Bn, and $-(O)_{0-1}-R^5$;

$R^5$ is independently selected from: phenyl and pyridyl; wherein each moiety is substituted with 0-2 $R^c$; and $R^c$, at each occurrence, is independently selected from: halogen, $C_{1-4}$ alkyl, $C_{1-4}$ alkoxy, $C_{1-4}$ haloalkyl, $C_{1-4}$ haloalkoxy, and $CO_2(C_{1-4}$ alkyl).

4. A compound selected from:

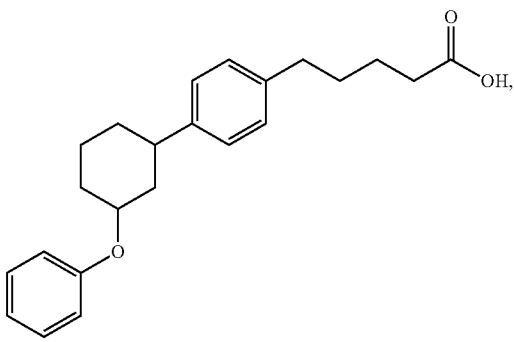

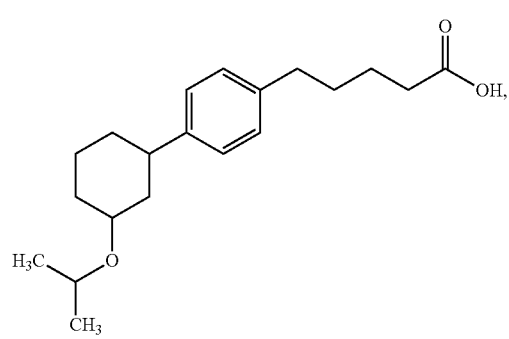

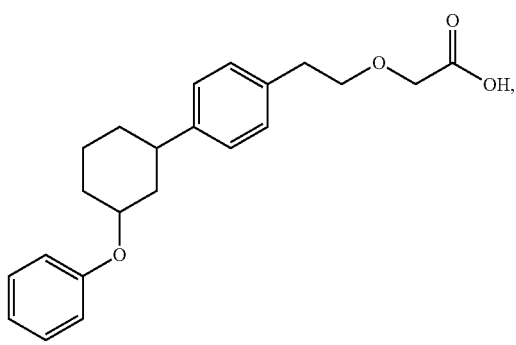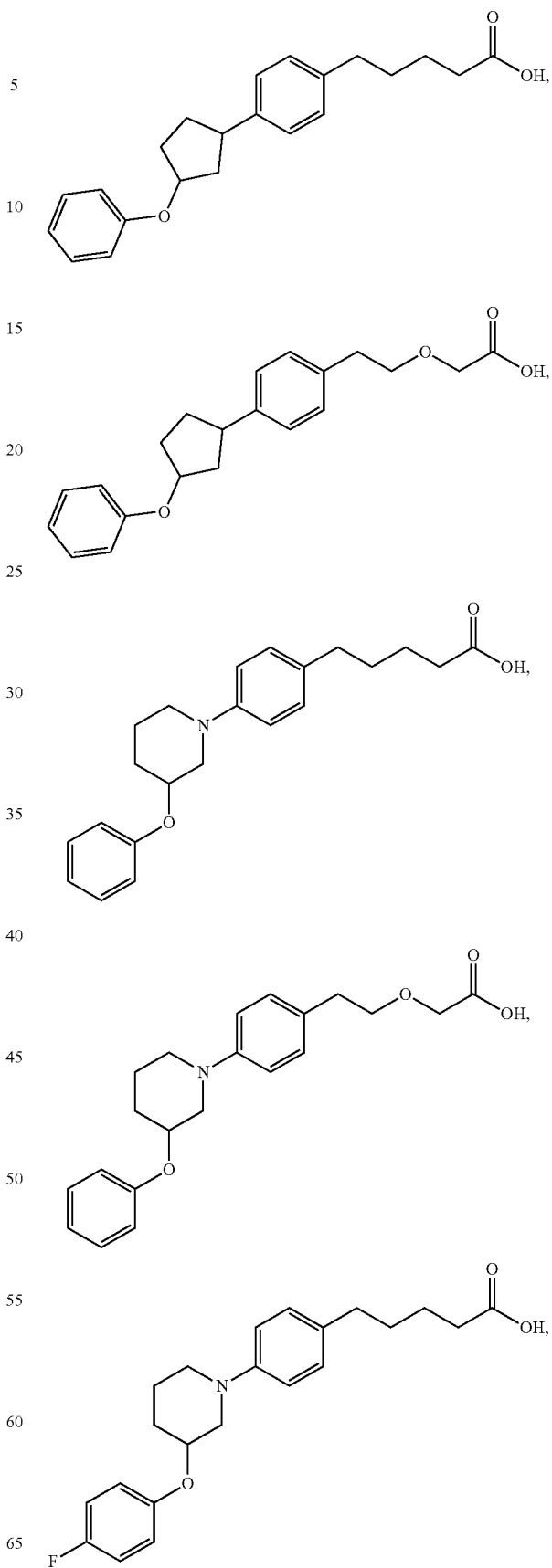

111
-continued
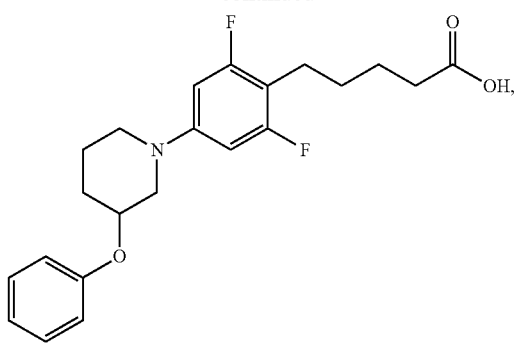
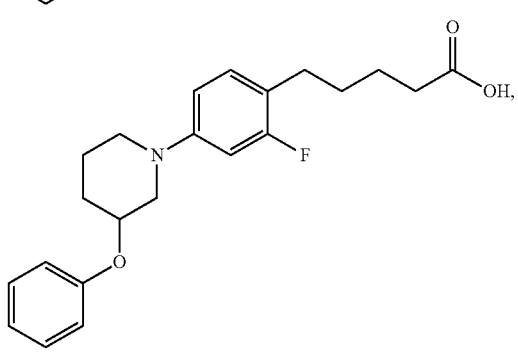
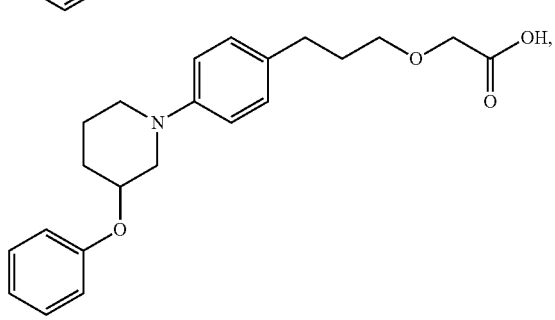
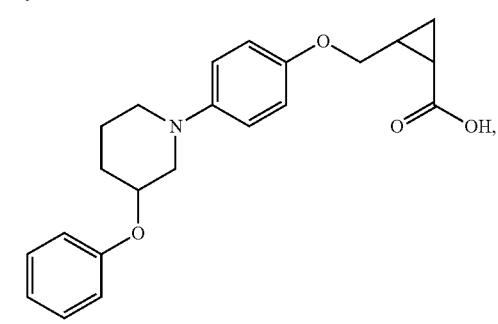
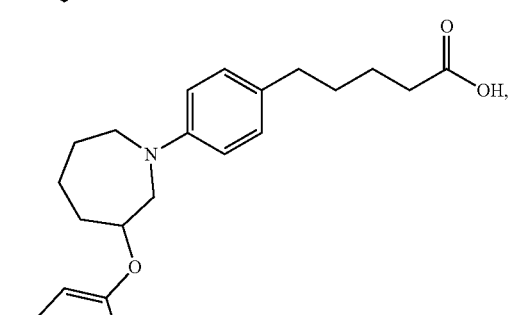
112
-continued
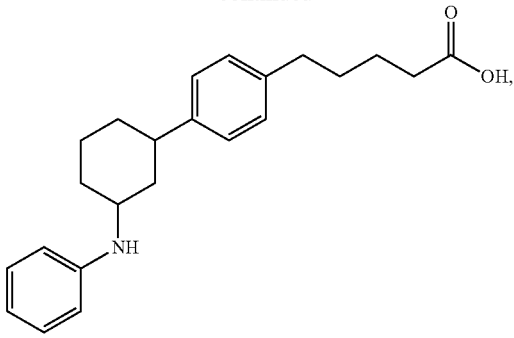
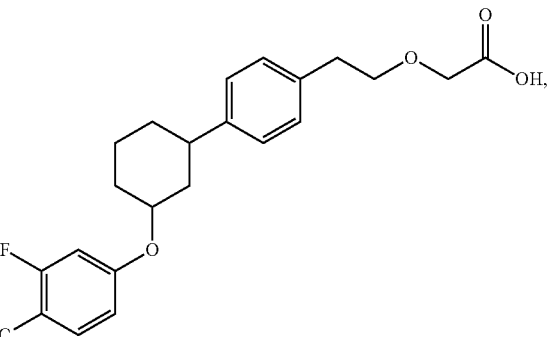
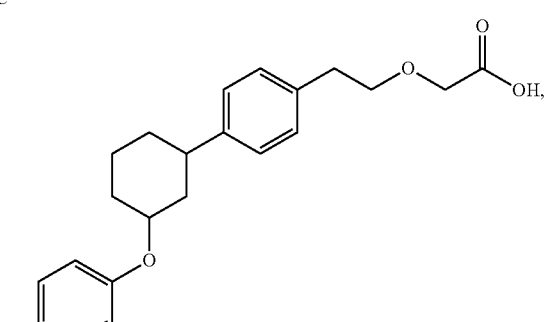
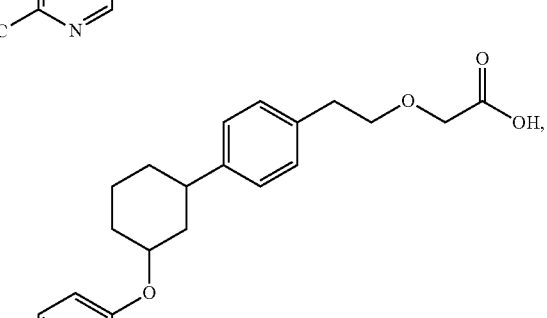
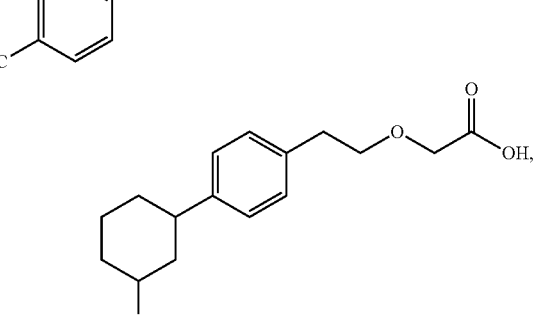

113
-continued
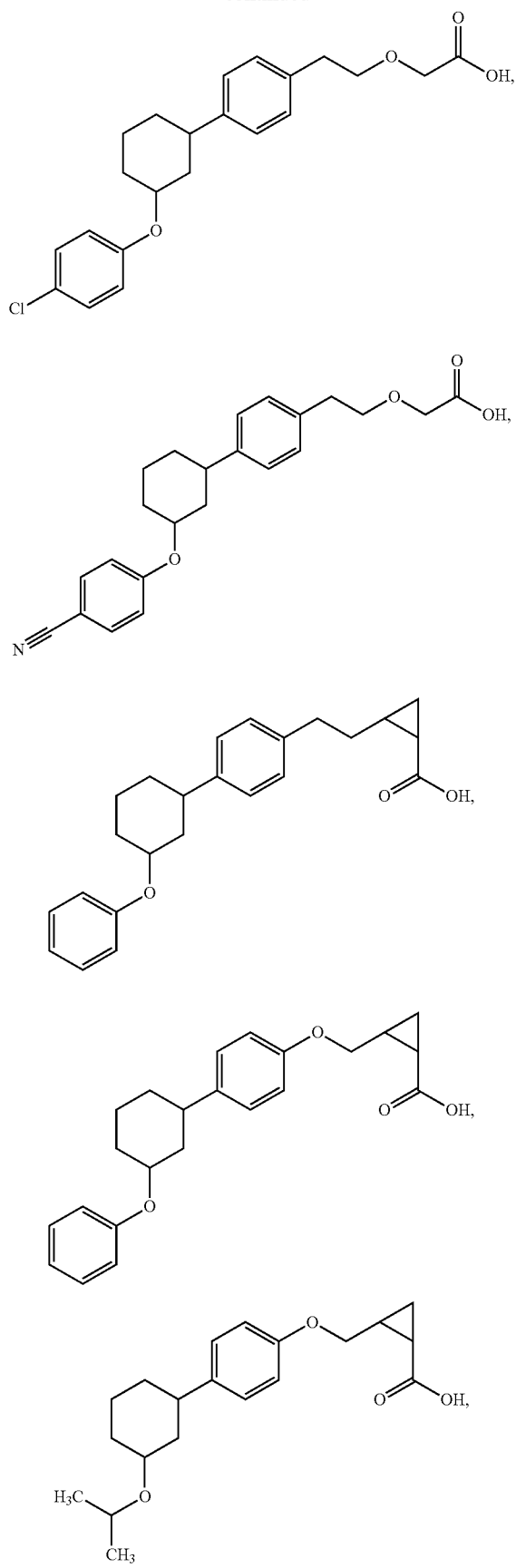
114
-continued
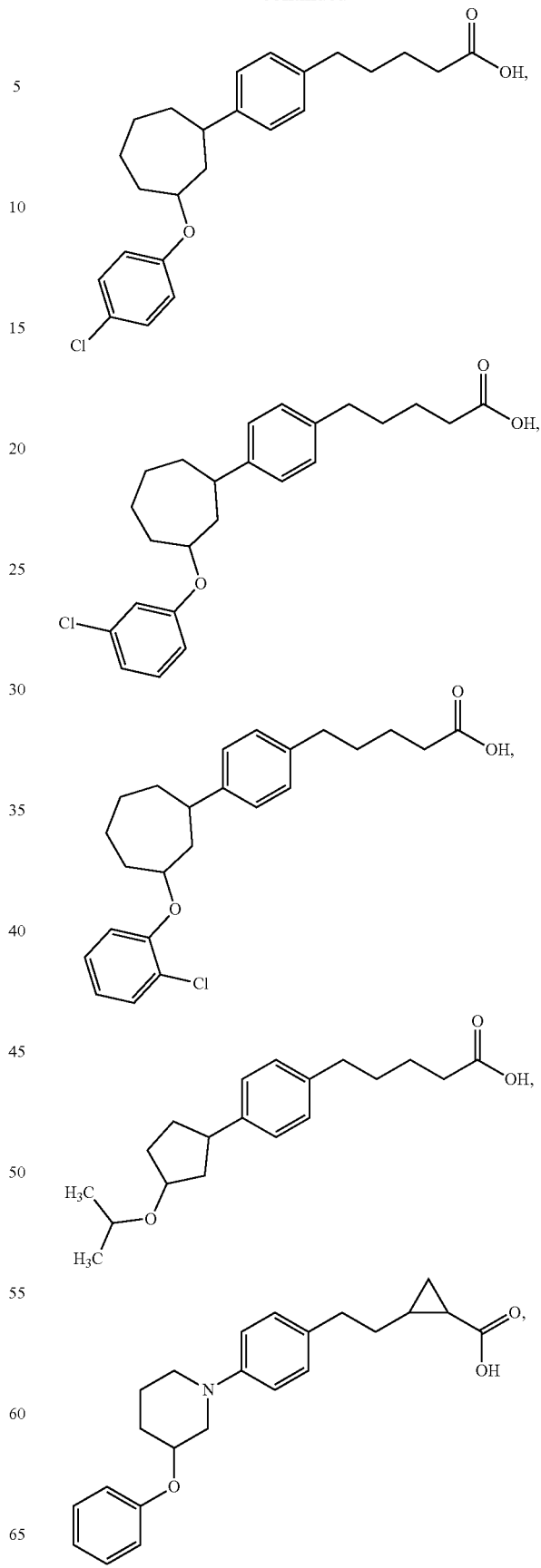

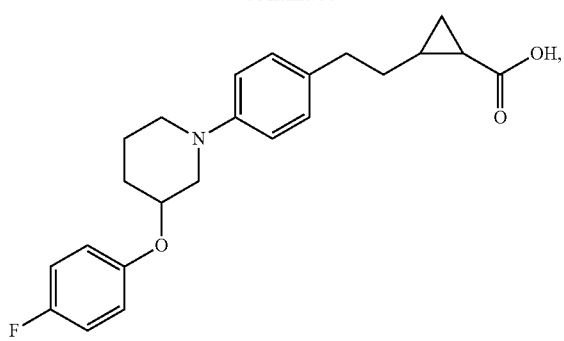
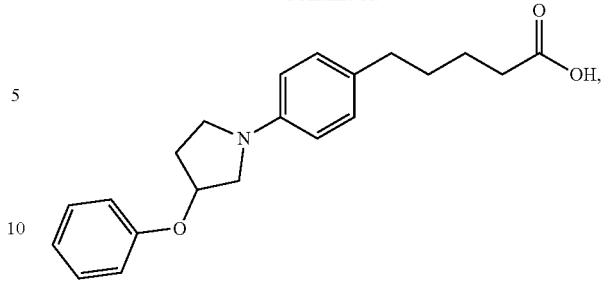

or a stereoisomer, or a pharmaceutically acceptable salt thereof.

5. A pharmaceutical composition, comprising a pharmaceutically acceptable carrier and a compound of claim 1, or a stereoisomer, a tautomer, or a pharmaceutically acceptable salt thereof.

6. The pharmaceutical composition according to claim 5, further comprising one or more other suitable therapeutic agents selected from: a dipeptidyl peptidase-IV inhibitor, a sodium-glucose transporter-2 inhibitor and a 11b-HSD-1 inhibitor.

7. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 1.

8. A pharmaceutical composition, comprising a pharmaceutically acceptable carrier and a compound of claim 2, or a stereoisomer, a tautomer, or a pharmaceutically acceptable salt thereof.

9. The pharmaceutical composition according to claim 8, further comprising one or more other suitable therapeutic agents selected from: a dipeptidyl peptidase-IV inhibitor, a sodium-glucose transporter-2 inhibitor and a 11b-HSD-1 inhibitor.

10. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 2.

11. A pharmaceutical composition, comprising a pharmaceutically acceptable carrier and a compound of claim 3, or a stereoisomer, a tautomer, or a pharmaceutically acceptable salt thereof.

12. The pharmaceutical composition according to claim 11, further comprising one or more other suitable therapeutic agents selected from: a dipeptidyl peptidase-IV inhibitor, a sodium-glucose transporter-2 inhibitor and a 11b-HSD-1 inhibitor.

13. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 3.

14. A pharmaceutical composition, comprising a pharmaceutically acceptable carrier and a compound of claim 4, or a stereoisomer, or a pharmaceutically acceptable salt thereof.

15. The pharmaceutical composition according to claim 14, further comprising one or more other suitable therapeutic agents selected from: a dipeptidyl peptidase-IV inhibitor, a sodium-glucose transporter-2 inhibitor and a 11b-HSD-1 inhibitor.

16. A method for the treatment of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), lipid disorders and liver diseases, NASH (Non-Alcoholic SteatoHepatitis), NAFLD (Non-Alcoholic Fatty Liver Disease) or liver cirrhosis, comprising administering to a patient in need of such treatment a therapeutically effective amount of at least a compound according to claim 4.

\* \* \* \* \*